(12) United States Patent
Kaplan et al.

(10) Patent No.: US 11,236,392 B2
(45) Date of Patent: Feb. 1, 2022

(54) CLINICAL PREDICTORS OF WEIGHT LOSS

(71) Applicants: Ethicon Endo-Surgery, Inc., Cincinnati, OH (US); The General Hospital Corporation, Boston, MA (US)

(72) Inventors: Lee M. Kaplan, Wellesley, MA (US); Ida Hatoum, Weymouth, MA (US); Jason L. Harris, Lebanon, OH (US)

(73) Assignees: Ethicon Endo-Surgery, Inc., Cincinnati, OH (US); The General Hospital Corporation General Hospital, Boston, MA (US)

(*) Notice: Subject to any disclaimer, the term of this patent is extended or adjusted under 35 U.S.C. 154(b) by 0 days.

(21) Appl. No.: 15/799,271

(22) Filed: Oct. 31, 2017

(65) Prior Publication Data

US 2018/0066315 A1 Mar. 8, 2018

Related U.S. Application Data

(62) Division of application No. 13/828,809, filed on Mar. 14, 2013, now abandoned.

(60) Provisional application No. 61/704,077, filed on Sep. 21, 2012, provisional application No. 61/704,434, filed on Sep. 21, 2012, provisional application No. 61/740,678, filed on Dec. 21, 2012.

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,582,908 B2 | 6/2003 | Fodor et al. | |
| 7,194,301 B2 | 3/2007 | Jenkins et al. | |
| 7,901,885 B2 | 3/2011 | Salonen et al. | |
| 8,036,912 B2 | 10/2011 | Jensen et al. | |
| 8,156,166 B2 | 4/2012 | LeClair et al. | |
| 9,250,172 B2 | 2/2016 | Harris et al. | |
| 2005/0220710 A1 | 10/2005 | Seeley | |
| 2006/0040293 A1 | 2/2006 | Salonen et al. | |
| 2006/0062859 A1 | 3/2006 | Blum et al. | |
| 2006/0252050 A1 | 11/2006 | Ordovas et al. | |
| 2007/0054278 A1 | 3/2007 | Cargill | |
| 2007/0059722 A1 | 3/2007 | Salonen et al. | |
| 2007/0072798 A1 | 3/2007 | Salonen et al. | |
| 2007/0244375 A1 | 10/2007 | Jenkins et al. | |
| 2008/0227663 A1 | 9/2008 | Tisone et al. | |
| 2009/0018031 A1 | 1/2009 | Trinklein et al. | |
| 2009/0024144 A1 | 1/2009 | Zeiner et al. | |
| 2010/0098809 A1 | 4/2010 | Bender et al. | |
| 2010/0105038 A1 | 4/2010 | Draper et al. | |
| 2010/0112570 A1 | 5/2010 | Aziz et al. | |
| 2010/0113580 A1 | 5/2010 | Aronne | |
| 2010/0136561 A1 | 6/2010 | Draper et al. | |
| 2010/0209350 A1 | 8/2010 | Pfuetzner et al. | |
| 2010/0210541 A1 | 8/2010 | Pfuetzner | |
| 2011/0008906 A1 | 1/2011 | Aziz et al. | |
| 2011/0111404 A1 | 5/2011 | Salonen et al. | |
| 2011/0111405 A1 | 5/2011 | Salonen et al. | |
| 2011/0123981 A1 | 5/2011 | Dina et al. | |
| 2011/0124121 A1 | 5/2011 | Dixon et al. | |
| 2011/0263490 A1 | 10/2011 | Kaplan et al. | |
| 2011/0270360 A1 | 11/2011 | Harris et al. | |
| 2011/0282683 A1 | 11/2011 | Jensen et al. | |
| 2012/0040342 A1 | 2/2012 | Gerhard et al. | |
| 2012/0059779 A1 | 3/2012 | Syed et al. | |
| 2012/0078656 A1 | 3/2012 | Wennberg | |
| 2012/0296675 A1 | 11/2012 | Silverman | |

(Continued)

FOREIGN PATENT DOCUMENTS

| | | |
|---|---|---|
| EP | 2192196 A1 | 6/2010 |
| WO | WO-9947706 A1 | 9/1999 |

(Continued)

OTHER PUBLICATIONS

Hatoum et al. American J Human Genetics. May 2, 2013, 92: 827-834 (Year: 2013).*
Gastroenterology. May 2010. 138.5 Suppl. 1: S71, abstract 495 (Year: 2010).*
Gomez-Ambrosi, Javier et al., "Gene expression profileof omental adipose tissue in human obesity," The FASEB Journal, doi: 10.1096/fj.03-0591fje, 25 pages (2003).
GenBank Accession No. NM_028320, 6 pages Jun. 29, 2012.
Hatoum, Ida J. et al., "Weight Loss after Gastric Bypass Is Associated with a Variant at 15q26.1," The American Journal of Human Genetics, vol. 92 (2013):827-834.

(Continued)

*Primary Examiner* — Carla J Myers

(74) *Attorney, Agent, or Firm* — Mintz Levin Cohn Ferris Glovsky and Popeo, P.C.

(57) ABSTRACT

Methods and compositions are generally provided for treating metabolic disorders, e.g., obesity. One aspect discloses methods and compositions for obtaining a biological sample from the subject, evaluating the sample for the presence or absence of a genetic indicator, wherein the genetic indicator is selected from a single nucleotide polymorphism and a level of gene expression, and performing a first metabolic procedure if the genetic indicator is present, or performing an alternative second metabolic procedure if the genetic indicator is absent. One aspect discloses methods and compositions for obtaining a sample including deoxyribonucleic acids (DNA) from the subject, evaluating the DNA for an absence or presence of one or more genetic indicators and performing a first metabolic procedure or an alternative second metabolic procedure based on the absence or presence of the genetic indicator(s). Other aspects are also disclosed.

9 Claims, 19 Drawing Sheets

Specification includes a Sequence Listing.

(56) References Cited

U.S. PATENT DOCUMENTS

| | | |
|---|---|---|
| 2014/0087999 A1 | 3/2014 | Kaplan et al. |
| 2015/0248613 A1 | 9/2015 | Harris et al. |
| 2017/0286610 A9 | 10/2017 | Harris et al. |

FOREIGN PATENT DOCUMENTS

| | | |
|---|---|---|
| WO | WO-0050639 A2 | 8/2000 |
| WO | WO-2009117415 A2 | 9/2009 |
| WO | WO-2010/024852 A1 | 3/2010 |
| WO | WO-2011058232 A1 | 5/2011 |
| WO | WO-2011090765 A1 | 7/2011 |
| WO | WO-2011144818 A1 | 11/2011 |
| WO | WO-2012/072685 A1 | 6/2012 |
| WO | WO-2012092049 A2 | 7/2012 |
| WO | WO-2012092056 A1 | 7/2012 |
| WO | WO-2012092057 A1 | 7/2012 |
| WO | WO-2013115756 A2 | 8/2013 |

OTHER PUBLICATIONS

Moschen, A.R. et al., "Effects of weight loss induced by bariatric surgery on hepatic adipocytokine expression," J. Hepatol., vol. 51.4 (2009)765-777.

Rankinen, Tuomo et al., "The Human Obesity Gene Map: The 2005 Update," Obesity, vol. 14.4 (2006):529-644.

International Search Report for Application No. PCT/US13/60901, 6 pages, dated Jan. 30, 2014.

Embl-Ebi: "Alignment < EMBOSS Water < EMBL-EBI," Mar. 18, 2016, XP055259494, Retrieved from the Internet: <URL:http://ebi.ac.uk/Tools/services/web/toolresults.ebi?jobID=emboss_water-I20160318-083653-0195-18053694-pg> [retrieved on Mar. 18, 2016].

Embl-Ebi: "Alignment < EMBOSS Water < EMBL-EBI," Mar. 18, 2016, XP055259503, Retrieved from the Internet: <URL:http://ebi.ac.uk/Tools/services/web/toolresults.ebi?jobID=emboss_water-I20160318-085242-0215-67356976-oy> [retrieved on Mar. 18, 2016].

Meyers, "Human STS SHGC-15668, sequence tagged site—Nucleotide—NCBI," Jun. 4, 1996, XP055259460, Retrieved from the Internet: <URL:http://www.ncbi.nlm.nih.gov/nuccore/G15123> [retrieved on Mar. 18, 2016].

Supplementary Partial European Search Report for European Application No. 13839109.9 dated Apr. 1, 2016 (11 pages).

European Office Action for Application No. EP 13839109.9, dated Mar. 23, 2017.

NCBI. National Center for Biotechnology Information. (Bethesda, MD, USA). "Reference SNP (refSNP) Cluster Report: rs17702901" Available via url: <https://www.ncbi.nlm.nih.gov/projects/SNP/snp_ref.cgi?rs=17702901>, printed on Apr. 28, 2017.

[No Author Listed] BOLD Overview. Surgical Review Corporation. Retrieved from <http://www.surgicalreview.org/bold/overview>, 1 pg. Date unknown, but believed to be no later than Feb. 1, 2012.

[No Author Listed] Find out if you're a candidate for bariatric surgery (with results). Surgeon/Seminar Finder. Realize. Ethcon Endo-Surgery. 2012, 6 pages. Retrieved from <http://www.realize.com/bariatric-surgery-eligibility>.

[No Author Listed] Find out if you're a candidate for bariatric surgery. Surgeon/Seminar Finder. Realize. Ethcon Endo-Surgery. 2012, 4 pages. Retrieved from <http://www.realize.com/bariatric-surgery-eligibility>.

[No Author Listed] Find weight loss surgeons and information seminars. Surgeon/Seminar Finder. Realize. Ethcon Endo-Surgery. 2012, 2 pages. Retrieved from.

[No Author Listed] Frequently Asked Questions. Surgeon/Seminar Finder. Realize. Ethicon Endo-Surgery. 2012, 10 pages. Retrieved from <http://realize.com/faqs.html>.

[No Author Listed] Insight for better healthcare. Overview of Marketscan database. Thomson Reuters. 2010, 2 pages. Retrieved from <https://web.archive.org/web/20110309003451/http:/marketscan.thomsonreuters.com/marketscanportal/>.

[No Author Listed] Obesity treatment guide: A reference for assessing and treating overweight and obese patients. Bariatric Times. Physician handout. 2011, 2 pages. Last accessed Sep. 19, 2012 from <http://bariatrictimes.com/about/>.

[No Author Listed] Patient Guide. Realize. Ethicon Endo-Surgery. 2010, 56 pages.

[No Author Listed] Seminar Results. Surgeon/Seminar Finder. Realize. Ethicon Endo-Surgery. 2012, 3 pages. Retrieved from <http://realize.com/seminar-finder-results?zipcode=&state=OH&filte>.

[No Author Listed] Surgeon/Seminar Finder Results. Surgeon/Seminar Finder. Realize. Ethicon Endo-Surgery. 2012, 4 pages. Retrieved from <http://realize.com/surgeons-seminars-results?zipcode=&state=OH&f>.

Aslan et al., Weight loss after Roux-en-Y gastric bypass in obese patients heterozygous for MC4R mutations. Obes Surg. Jul. 2011;21(7):930-4. doi: 10.1007/s11695-010-0295-8.

Averbukh et al., Depression score predicts weight loss following Roux-en-Y gastric bypass. Obes Surg. Dec. 2003;13(6):833-6.

Baltasar et al., Weight loss reporting. Obes Surg. Jun. 2008;18(6):761-2. doi: 10.1007/s11695-008-9450-x. Epub Apr. 12, 2008.

Branson et al., Binge eating as a major phenotype of melanocortin 4 receptor gene mutations. N Engl J Med. Mar. 20, 2003;348(12):1096-103.

Bray, GA, et al., Is it time to change the way we report and discuss weight loss? Obesity (Silver Spring). Apr. 2009;17(4):619-21. doi: 10.1038/oby.2008.597.

Bray, GA, Medications for weight reduction. Endocrinol Metab Clin North Am. Dec. 2008;37(4):923-42. doi: 10.1016/j.ecl.2008.08.004.

Bray, MS, Implications of gene-behavior interactions: prevention and intervention for obesity. Obesity (Silver Spring). Dec. 2008;16 Suppl 3:S72-8. doi: 10.1038/oby.2008.522.

Buchwald et al., Bariatric surgery: a systematic review and meta-analysis. JAMA. Oct. 13, 2004;292(14):1724-37.

Busetto et al., Outcome predictors in morbidly obese recipients of an adjustable gastric band. Obes Surg. Feb. 2002;12(1):83-92.

Cawley et al., The medical care costs of obesity: an instrumental variables approach. J Health Econ. Jan. 2012;31(1):219-30. doi: 10.1016/j.jhealeco.2011.10.003. Epub Oct. 20, 2011.

Chambers et al., Weight-independent changes in blood glucose homeostasis after gastric bypass or vertical sleeve gastrectomy in rats. Gastroenterology. Sep. 2011;141(3):950-8. doi: 10.1053/j.gastro.2011.05.050. Epub Jul. 12, 2011.

Chen et al., Ala55Val polymorphism on UCP2 gene predicts greater weight loss in morbidly obese patients undergoing gastric banding. Obes Surg. Jul. 2007;17(7):926-33.

Chobanian et al., The Seventh Report of the Joint National Committee on Prevention, Detection, Evaluation, and Treatment of High Blood Pressure: the JNC 7 report. JAMA. May 21, 2003;289(19):2560-72. Epub May 14, 2003.

Chu et al., Association of morbid obesity with FTO and INSIG2 allelic variants. Arch Surg. Mar. 2008;143(3):235-40; discussion 241. doi: 10.1001/archsurg.2007.77.

Corella et al., Obese subjects carrying the 11482G>A polymorphism at the perilipin locus are resistant to weight loss after dietary energy restriction. J Clin Endocrinol Metab. Sep. 2005;90(9):5121-6. Epub Jun. 28, 2005.

Cushman et al., Success and predictors of blood pressure control in diverse North American settings: the antihypertensive and lipid-lowering treatment to prevent heart attack trial (ALLHAT). J Clin Hypertens (Greenwich). Nov.-Dec. 2002;4(6):393-404.

De Luis et al., Effects of C358A missense polymorphism of the endocannabinoid degrading enzyme fatty acid amide hydrolase on weight loss and cardiovascular risk factors 1 year after biliopancreatic diversion surgery. Surg Obes Relat Dis. Sep.-Oct. 2010;6(5):516-20. doi: 10.1016/j.soard.2010.01.005. Epub Feb. 6, 2010.

De Luis et al., G1359A polymorphism of the cannabinoid receptor gene (CNR1) and clinical results of biliopancreatic diversion. Eur Rev Med Pharmacol Sci. Mar. 2010;14(3):197-201.

De Luis et al., Influence of -55CT polymorphism of UCP3 gene on surgical results of biliopancreatic diversion. Obes Surg. Jul. 2010;20(7):895-9. doi: 10.1007/s11695-008-9510-2. Epub May 17, 2008.

(56) References Cited

OTHER PUBLICATIONS

De Luis et al., Influence of ALA54THR polymorphism of fatty acid binding protein 2 on lifestyle modification response in obese subjects. Ann Nutr Metab. 2006;50(4):354-60. Epub Jun. 28, 2006.
De Luis et al., Influence of Ala54Thr polymorphism of fatty acid-binding protein 2 on weight loss and insulin levels secondary to two hypocaloric diets: a randomized clinical trial. Diabetes Res Clin Pract. Oct. 2008;82(1):113-8. doi: 10.1016/j.diabres.2008.07.005. Epub Aug. 12, 2008.
De Luis et al., Influence of Ala54Thr polymorphism of fatty acid-binding protein-2 on clinical results of biliopancreatic diversion. Nutrition. Apr. 2008;24(4):300-4. doi: 10.1016/j.nut.2007.12.009. Epub Feb. 15, 2008.
De Luis et al., Influence of G308A polymorphism of tumor necrosis factor alpha gene on surgical results of biliopancreatic diversion. Obes Surg. Feb. 2010;20(2):221-5. doi: 10.1007/s11695-008-9591-y. Epub Jun. 20, 2008.
De Luis et al., Influence of lys656asn polymorphism of leptin receptor gene on surgical results of biliopancreatic diversion. J Gastrointest Surg. May 2010;14(5):899-903. doi: 10.1007/s11605-010-1181-3. Epub Mar. 6, 2010.
Deitel et al., Recommendations for reporting weight loss. Obes Surg. Apr. 2003;13(2):159-60.
Deitel et al., Reporting weight loss 2007. Obes Surg. May 2007;17(5):565-8.
Deram et al., Effects of perilipin (PLIN) gene variation on metabolic syndrome risk and weight loss in obese children and adolescents. J Clin Endocrinol Metab. Dec. 2008;93(12):4933-40. doi: 10.1210/jc.2008-0947. Epub Sep. 23, 2008.
Deram et al., Genetic variants influencing effectiveness of weight loss strategies. Arq Bras Endocrinol Metabol. Mar. 2009;53(2):129-38.
Di Renzo et al., Body composition changes after laparoscopic adjustable gastric banding: what is the role of -174G>C interleukin-6 promoter gene polymorphism in the therapeutic strategy? Int J Obes (Lond). Mar. 2012;36(3):369-78. doi: 10.1038/ijo.2011.132. Epub Jul. 5, 2011.
Dixon et al., Minimal reporting requirements for weight loss: current methods not ideal. Obes Surg. Aug. 2005;15(7):1034-9.
Dixon et al., Pre-operative predictors of weight loss at 1-year after Lap-Band surgery. Obes Surg. Apr. 2001;11(2):200-7.
Drazen et al., Peripheral signals in the control of satiety and hunger. Curr Opin Clin Nutr Metab Care. Nov. 2003;6(6):621-9.
Gagneaux et al. Molecular Phylogenetics and Evolution. 2001. 18:2-13.
Garaulet et al., CLOCK gene is implicated in weight reduction in obese patients participating in a dietary programme based on the Mediterranean diet. Int J Obes (Lond). Mar. 2010;34(3):516-23. doi: 10.1038/ijo.2009.255. Epub Jan. 12, 2010.
Gardner et al., Comparison of the Atkins, Zone, Ornish, and LEARN diets for change in weight and related risk factors among overweight premenopausal women: the A To Z Weight Loss Study: a randomized trial. JAMA. Mar. 7, 2007;297(9):969-77.
Geloneze et al., PGC1a gene Gly482Ser polymorphism predicts improved metabolic, inflammatory and vascular outcomes following bariatric surgery. Int J Obes (Lond). Mar. 2012;36(3):363-8. doi: 10.1038/ijo.2011.176. Epub Sep. 6, 2011.
Gerhard et al., The influence of iron status and genetic polymorphisms in the HFE gene on the risk for postoperative complications after bariatric surgery: a prospective cohort study in 1,064 patients. Patient Saf Surg. Jan. 10, 2011;5(1):1. doi: 10.1186/1754-9493-5-1.
Goyenechea et al., The—11391 G/A polymorphism of the adiponectin gene promoter is associated with metabolic syndrome traits and the outcome of an energy-restricted diet in obese subjects. Horm Metab Res. Jan. 2009;41(1):55-61. doi: 10.1055/s-0028-1087204. Epub Oct. 23, 2008.
Greenawalt et al., A survey of the genetics of stomach, liver, and adipose gene expression from a morbidly obese cohort. Genome Res. Jul. 2011;21 (7): 1008-16. doi: 10.1101/gr.112821.110. Epub May 20, 2011.

Hainer et al., Role of hereditary factors in weight loss and its maintenance. Physiol Res. 2008;57 Suppl 1:S1-15. Epub Feb. 13, 2008.
Halushka et al. Natuer. Jul. 1999. 22: 239-247.
Hatoum et al., Capacity for physical activity predicts weight loss after Roux-en-Y gastric bypass. Obesity (Silver Spring). Jan. 2009;17(1):92-9. doi: 10.1038/oby.2008.507. Epub Nov. 6, 2008.
Hatoum et al., Heritability of the weight loss response to gastric bypass surgery. J Clin Endocrinol Metab. Oct. 2011;96(10):E1630-3. doi: 10.1210/jc.2011-1130. Epub Aug. 10, 2011.
Hatoum et al., Melanocortin-4 receptor signaling is required for weight loss after gastric bypass surgery. J Clin Endocrinol Metab. Jun. 2012;97(6):E1023-31. doi: 10.1210/jc.2011-3432. Epub Apr. 6, 2012.
Hattersley et al. The Lancet. 2005. 366:1315-1323.
Haupt et al., Impact of variation in the FTO gene on whole body fat distribution, ectopic fat, and weight loss. Obesity (Silver Spring). Aug. 2008;16(8):1969-72. doi: 10.1038/oby.2008.283. Epub May 29, 2008.
Haupt et al., Impact of variation near MC4R on whole-body fat distribution, liver fat, and weight loss. Obesity (Silver Spring). Oct. 2009;17(10):1942-5. doi: 10.1038/oby.2009.233. Epub Jul. 30, 2009.
Hirsch, A., Considering weight loss surgery? There's an app for that. Bucknell University. Sep. 10, 2012, 2 pages.
Hirschhorn et al. Genetics in Medicine. vol. 4, No. 2, pp. 45-61, Mar. 2002.
International Search Report and Written Opinion for Application No. PCT/US2013/60825 dated Dec. 13, 2013 (17 Pages).
Kalari et al. BMC Genomics. 2010. 11:357.
Kaplan, LM, Pharmacologic therapies for obesity. Gastroenterol Clin North Am. Mar. 2010;39(1):69-79. doi: 10.1016/j.gtc.2010.01.001.
Karamanakos et al., Weight loss, appetite suppression, and changes in fasting and postprandial ghrelin and peptide-YY levels after Roux-en-Y gastric bypass and sleeve gastrectomy: a prospective, double blind study. Ann Surg. Mar. 2008;247(3):401-7. doi: 10.1097/SLA.0b013e318156f012.
Karmali et al., Is it time to abandon excess weight loss in reporting surgical weight loss? Surg Obes Relat Dis. Jul.-Aug. 2009;5(4):503-6. doi: 10.1016/j.soard.2009.04.014. Epub May 6, 2009.
Kral et al., Melanocortin-4 receptor gene variants affect results of gastric banding. Digestive Disease Week 2004, 45th Annual Meeting. Gastroenterology 2004; 126 Suppl. 2 A-768. Abstract.
Lappalainen et al., The common variant in the FTO gene did not modify the effect of lifestyle changes on body weight: the Finnish Diabetes Prevention Study. Obesity (Silver Spring). Apr. 2009;17(4):832-6. doi: 10.1038/oby.2008.618. Epub Jan. 29, 2009.
Lee et al., Bariatric surgery: Asia-Pacific perspective. Obes Surg. Jun.-Jul. 2005;15(6):751-7.
Lee et al., Prediction of successful weight reduction after laparoscopic adjustable gastric banding. Hepatogastroenterology. Jul.-Aug. 2009;56(93):1222-6.
Li et al., MaCH: using sequence and genotype data to estimate haplotypes and unobserved genotypes. Genet Epidemiol. Dec. 2010;34(8):816-34. doi: 10.1002/gepi.20533.
Libra et al., Molecular determinants in the transport of a bile acid-derived diagnostic agent in tumoral and nontumoral cell lines of human liver. J Pharmacol Exp Ther. Nov. 2006;319(2):809-17. Epub Aug. 8, 2006.
Lindi et al., Association of the Pro12Ala polymorphism in the PPAR-gamma2 gene with 3-year incidence of type 2 diabetes and body weight change in the Finnish Diabetes Prevention Study. Diabetes. Aug. 2002;51(8):2581-6.
Liou et al., ESR1, FTO, and UCP2 genes interact with bariatric surgery affecting weight loss and glycemic control in severely obese patients. Obes Surg. Nov. 2011;21(11):1758-65. doi: 10.1007/s11695-011-0457-3.
Lucentini et al. Te Scientist (2004) vol. 18, p. 20.
Lutfi et al., Predictors of success after laparoscopic gastric bypass: a multivariate analysis of socioeconomic factors. Surg Endosc. Jun. 2006;20(6):864-7. Epub May 2, 2006.
Luyckx et al., Influence of the A-->G (-3826) uncoupling protein-1 gene (UCP1) variant on the dynamics of body weight before and

(56) References Cited

OTHER PUBLICATIONS after gastroplasty in morbidly obese subjects. Int J Obes Relat Metab Disord. Dec. 1998;22(12):1244-5.

Ma et al., Predictors of weight status following laparoscopic gastric bypass. Obes Surg. Sep. 2006;16(9):1227-31.

Masuo et al., Rebound weight gain as associated with high plasma norepinephrine levels that are mediated through polymorphisms in the beta2-adrenoceptor. Am J Hypertens. Nov. 18, 2005(11):1508-16.

Matsuo et al., PPARG genotype accounts for part of individual variation in body weight reduction in response to calorie restriction. Obesity (Silver Spring). Oct. 2009;17(10):1924-31. doi: 10.1038/oby.2009.199. Epub Jun. 18, 2009.

McAuley et al., Identification of sialyltransferase 8B as a generalized susceptibility gene for psychotic and mood disorders on chromosome 15q25-26. PLoS One. 2012;7(5):e38172. doi: 10.1371/journal.pone.0038172. Epub May 31, 2012.

McMinn et al., Neuroendocrine mechanisms regulating food intake and body weight. Obes Rev. May 2000;1(1):37-46.

Mirshahi et al., The MC4R(I251L) allele is associated with better metabolic status and more weight loss after gastric bypass surgery. J Clin Endocrinol Metab. Dec. 2011;96(12):E2088-96. doi: 10.1210/jc.2011-1549. Epub Oct. 5, 2011.

Montasser et al., Gene by smoking interaction in hypertension: identification of a major quantitative trait locus on chromosome 15q for systolic blood pressure in Mexican-Americans. J Hypertens. Mar. 2009;27(3):491-501.

Moreno-Aliaga et al., Does weight loss prognosis depend on genetic make-up? Obes Rev. May 2005;6(2):155-68.

Muller et al., 'Fat mass and obesity associated' gene (FTO): no significant association of variant rs9939609 with weight loss in a lifestyle intervention and lipid metabolism markers in German obese children and adolescents. BMC Med Genet. Sep. 17, 2008;9:85. doi: 10.1186/1471-2350-9-85.

YiXin et al., [The impact of obesity on oxygen desaturation in patients with sleep apnea/hypopnea syndrome]. Nihon Kokyuki Gakkai Zasshi. Sep. 2001;39(9):650-5. Japanese-language article. English abstract only.

NCBI. National Center for Biotechnology Information. (Bethesda, MD, USA). Probe Database for rs1108723, available via url: <ncbi.nlm.nih.gov/probe/>, printed on Feb. 3, 2016.

NCBI. National Center for Biotechnology Information. (Bethesda, MD, USA). Probe Database for rs2383289, available via url: <ncbi.nlm.nih.gov/probe/>, printed on Feb. 3, 2016.

NCBI. National Center for Biotechnology Information. (Bethesda, MD, USA). Probe Database for rs3734399, available via url: <ncbi.nlm.nih.gov/probe/>, printed on Feb. 3, 2016.

NCBI. National Center for Biotechnology Information. (Bethesda, MD, USA). Probe Database for rs4603757, available via url: <ncbi.nlm.nih.gov/probe/>, printed on Feb. 3, 2016.

NCBI. National Center for Biotechnology Information. (Bethesda, MD, USA). Probe Database for rs6737079, available via url: <ncbi.nlm.nih.gov/probe/>, printed on Feb. 3, 2016.

NCBI. National Center for Biotechnology Information. (Bethesda, MD, USA). Probe Database for rs6911751, available via url: <ncbi.nlm.nih.gov/probe/>, printed on Feb. 3, 2016.

NCBI. National Center for Biotechnology Information. (Bethesda, MD, USA). Probe Database for rs6925786, available via url: <ncbi.nlm.nih.gov/probe/>, printed on Feb. 3, 2016.

NCBI. National Center for Biotechnology Information. (Bethesda, MD, USA). Probe Database for rs9474779, available via url: <ncbi.nlm.nih.gov/probe/>, printed on Feb. 3, 2016.

Nicklas et al., Genetic variation in the peroxisome proliferator-activated receptor-gamma2 gene (Pro12Ala) affects metabolic responses to weight loss and subsequent weight regain. Diabetes. Sep. 2001;50(9):2172-6.

Ochner et al., Selective reduction in neural responses to high calorie foods following gastric Bypass surgery. Ann Surg. Mar. 2011;253(3):502-7. doi: 10.1097/SLA.0b013e318203a289.

Ogden et al., Prevalence of overweight and obesity in the United States, 1999-2004. JAMA. Apr. 5, 2006;295(13):1549-55.

Peterli et al., Improvement in glucose metabolism after bariatric surgery: comparison of laparoscopic Roux-en-Y gastric bypass and laparoscopic sleeve gastrectomy: a prospective randomized trial. Ann Surg. Aug. 2009;250(2):234-41. doi: 10.1097/SLA.0b013e3181ae32e3.

Peterli et al., Melanocortin-4 receptor gene and complications after gastric banding. Obes Surg. Feb. 2006;16(2):189-95.

Potoczna et al., G protein polymorphisms do not predict weight loss and improvement of hypertension in severely obese patients. J Gastrointest Surg. Nov. 2004;8(7):862-8; discussion 868.

Potoczna et al., Gene variants and binge eating as predictors of comorbidity and outcome of treatment in severe obesity. J Gastrointest Surg. Dec. 2004;8(8):971-81; discussion 981-2.

Price et al., Principal components analysis corrects for stratification in genome-wide association studies. Nat Genet. Aug. 2006;38(8):904-9. Epub Jul. 23, 2006.

Purcell et al., PLINK: a tool set for whole-genome association and population-based linkage analyses. Am J Hum Genet. Sep. 2007;81(3):559-75. Epub Jul. 25, 2007.

Rankinen et al., FTO genotype is associated with exercise training-induced changes in body composition. Obesity (Silver Spring). Feb. 2010;18(2):322-6. doi: 10.1038/oby.2009.205. Epub Jun. 18, 2009.

Reinehr et al., Aggravating effect of INSIG2 and FTO on overweight reduction in a one-year lifestyle intervention. Arch Dis Child. Dec. 2009;94(12):965-7. doi: 10.1136/adc.2008.147652. Epub Feb. 17, 2009.

Ryden et al., Weight Loss After Vertical Banded Gastroplasty Can Be Predicted: A Prospective Psychological Study. Obes Surg. Jun. 1996;6(3):237-243.

Sakane et al., Effects of Trp64Arg mutation in the beta 3-adrenergic receptor gene on weight loss, body fat distribution, glycemic control, and insulin resistance in obese type 2 diabetic patients. Diabetes Care. Dec. 1997;20(12):1887-90.

Santos et al., Allelic variants of melanocortin 3 receptor gene (MC3R) and weight loss in obesity: a randomised trial of hypo-energetic high- versus low-fat diets. PLoS One. 2011;6(6):e19934. doi: 10.1371/journal.pone.0019934. Epub Jun. 14, 2011.

Sarahan et al., Four out of eight genes in a mouse chromosome 7 congenic donor region are candidate obesity genes. Physiol Genomics. Sep. 22, 2011;43(18):1049-55. doi: 10.1152/physiolgenomics.00134.2010. Epub Jul. 5, 2011.

Sarzynski et al., Associations of markers in 11 obesity candidate genes with maximal weight loss and weight regain in the SOS bariatric surgery cases. Int J Obes (Lond). May 2011;35(5):676-83. doi: 10.1038/ijo.2010.166. Epub Aug. 24, 2010.

Schauer et al., Bariatric surgery versus intensive medical therapy in obese patients with diabetes. N Engl J Med. Apr. 26, 2012;366(17):1567-76. doi: 10.1056/NEJMoa1200225. Epub Mar. 26, 2012.

Sesti et al., Impact of common polymorphisms in candidate genes for insulin resistance and obesity on weight loss of morbidly obese subjects after laparoscopic adjustable gastric banding and hypocaloric diet. J Clin Endocrinol Metab. Sep. 2005;90(9):5064-9. Epub Jun. 28, 2005.

Sharma et al., Reporting weight loss: is simple better? Obesity (Silver Spring). Feb. 2010;18(2):219. doi: 10.1038/oby.2009.289.

Shin et al., Roux-en-Y gastric bypass surgery changes food reward in rats. Int J Obes (Lond). May 2011;35(5):642-51.doi: 10.1038/ijo.2010.174. Epub Aug. 31, 2010.

Sjostrom et al., Effects of bariatric surgery on mortality in Swedish obese subjects. N Engl J Med. Aug. 23, 2007;357(8):741-52.

Sorensen et al., Genetic polymorphisms and weight loss in obesity: a randomised trial of hypo-energetic high-versus low-fat diets. PLoS Clin Trials. Jun. 2006;1(2):e12, 14 pages. Epub Jun. 30, 2006.

Spalova et al., Neuromedin beta: P73T polymorphism in overweight and obese subjects. Physiol Res. 2008;57 Suppl 1 :S39-48. Epub Feb. 13, 2008.

Speliotes et al., Association analyses of 249,796 individuals reveal 18 new loci associated with body mass index. Nat Genet. Nov. 2010;42(11):937-48. doi: 10.1038/ng.686. Epub Oct. 10, 2010.

(56) References Cited

OTHER PUBLICATIONS

Still et al., High allelic burden of four obesity SNPs is associated with poorer weight loss outcomes following gastric bypass surgery. Obesity (Silver Spring). Aug. 2011;19(8):1676-83. doi: 10.1038/oby.2011.3. Epub Feb. 10, 2011.

Stone, J. May 2009. Illumina. "An Overview of Illumina's DNA Analysis Products—From Genotyping to CNV," 27 pages, available via url: <illumina.com/documents/seminars/preentations/2009_05_stone_jennifer.pdf>.

Stylopoulos et al., Roux-en-Y gastric bypass enhances energy expenditure and extends lifespan in diet-induced obese rats. Obesity (Silver Spring). Oct. 2009;17(10):1839-47. doi: 10.1038/oby.2009.207. Epub Jun. 25, 2009.

Suchanek et al., Actigenetic of ACE gene polymorphism in Czech obese sedentary females. Physiol Res. 2009;58 Suppl 1:S47-52.

Thornton et al., Real-time PCR (qPCR) primer design using free online software. Biochem Mol Biol Educ. Mar.-Apr. 2011;39(2):145-54.

Wang et al., ANAPC1 and SLCO3A1 are associated with nicotine dependence: meta-analysis of genome-wide association studies. Drug Alcohol Depend. Aug. 1, 2012; 124(3):325-32. doi: 10.1016/j.drugalcdep.2012.02.003. Epub Feb. 28, 2012.

Wing et al., Long-term effects of a lifestyle intervention on weight and cardiovascular risk factors in individuals with type 2 diabetes mellitus: four-year results of the Look AHEAD trial. Arch Intern Med. Sep. 27, 2010;170(17):1566-75. doi: 10.1001/archinternmed.2010.334.

Extended European Search Report for EP 13839109.9 dated Jul. 1, 2016 (20 pages).

Greenhill, "Obesity: Weight loss after Roux-en-Y gastric bypass is associated with SNPs in ghrelin receptor gene," Nature Reviews / Gastroenterology & Hepatology, vol. 9, No. 5, Apr. 10, 2012, pp. 243-243, XP055282402, US ISSN: 1759-5045, DOI: 10.1038/nrgastro.2012.65.

Matzko et al., "Association of Ghrelin Receptor Promoter Polymorphisms with Weight Loss Following Roux-en-Y Gastric Bypass Surgery," Obesity Surgery, The Journal of Metabolic Surgery and Allied Care, Spring Verlag, New York, vol. 22, No. 5, Mar. 13, 2012, pp. 783-790, XP035040016, ISSN: 1708-0428, DOI: 10.1007/S11695-012-0631-2.

\* cited by examiner

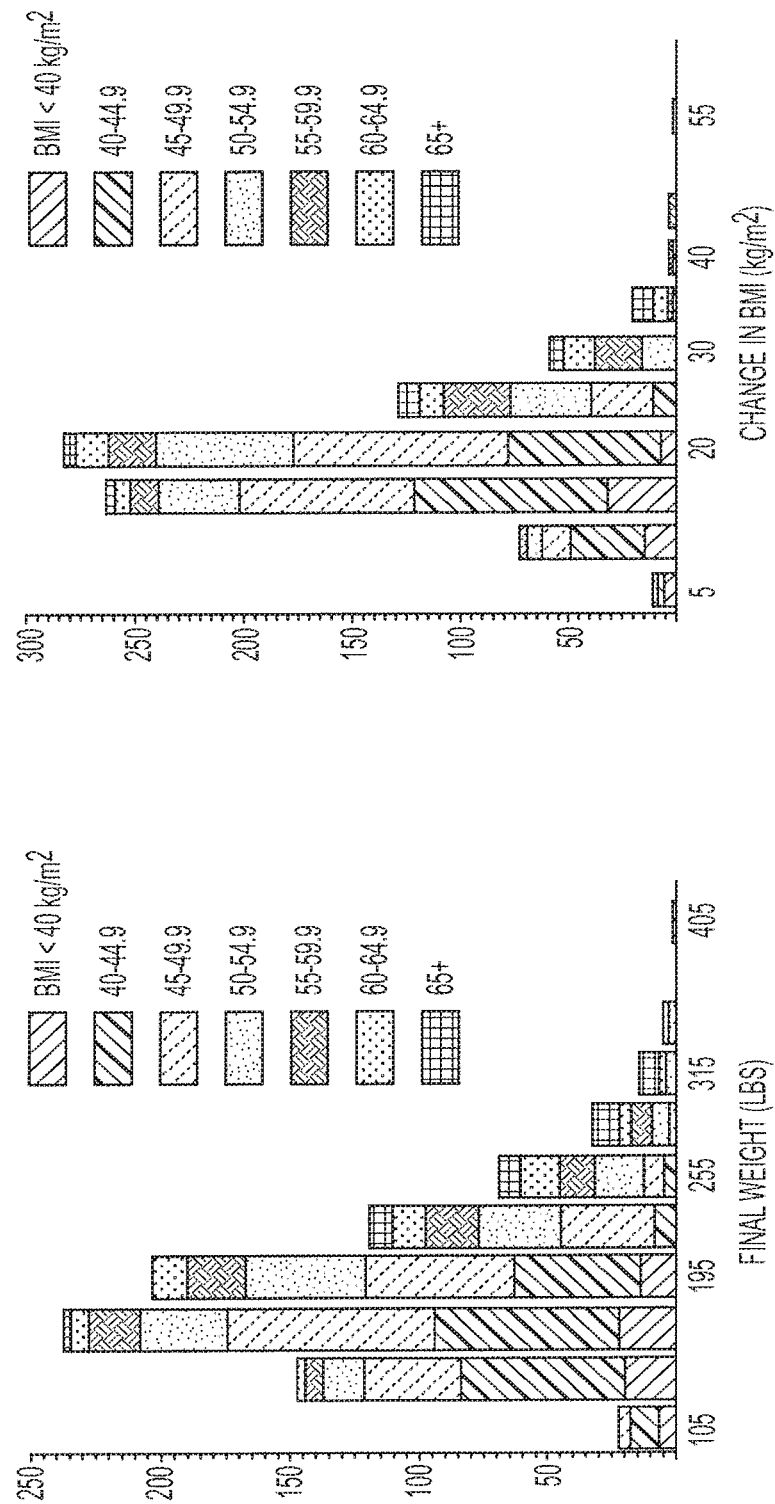

CLINICAL PREDICTORS OF WEIGHT LOSS

CROSS REFERENCE TO RELATED APPLICATIONS

The present invention is a divisional application and claims the priority of U.S. patent application Ser. No. 13/828,809, filed on Mar. 14, 2013, which claims the priority of U.S. Provisional Application Ser. No. 61/704,434, filed on Sep. 21, 2012, U.S. Provisional Application Ser. No. 61/704,077, filed Sep. 21, 2012, and U.S. Provisional Application Ser. No. 61/740,678, filed on Dec. 21, 2012, which are hereby incorporated by reference in their entirety. In the case of any inconsistency, the instant application supersedes the prior applications.

SEQUENCE LISTING

The instant application contains a Sequence Listing, which has been submitted in ASCII format via EFS-Web and is hereby incorporated by reference in its entirety. Said ASCII copy, created on Oct. 30, 2017 is named 047364_113D01US_Sequence_Listing.txt and is 1,318,912 bytes in size.

FIELD OF THE INVENTION

The present invention relates to genetic predictors for treatment of metabolic disorders and diseases, such as obesity.

BACKGROUND OF THE INVENTION

It is estimated that 66% of adults in the United States are overweight, including 32% who have obesity. The myriad metabolic, inflammatory, degenerative, cognitive, and neoplastic sequealae of obesity together cost more than $168 billion annually and account for nearly 10% of all healthcare expenditures in the United States.

Behavioral and pharmacotherapeutic treatments for severe obesity have been met with limited long-term success. In contrast, metabolic and bariatric operations such as Roux-en-Y gastric bypass (RYGB) lead to significant and sustained weight loss. Because of its excellent clinical outcomes, RYGB is currently the most commonly used surgical therapy for obesity. Metabolic and bariatric surgical procedures are increasingly being performed laparoscopically. Reduced postoperative recovery time, markedly decreased post operative pain and wound infection, and improved cosmetic outcome are well established benefits of laparoscopic surgery, derived mainly from the ability of laparoscopic surgeons to perform an operation utilizing smaller incisions of the body cavity wall.

Despite the various metabolic and bariatric surgical procedures each providing chances for weight loss and associated improvements in comorbid conditions, there is wide variability in outcomes (e.g., weight loss, improvements in diabetes and other comorbidities of obesity, adverse sequelae, etc.) among individual patients who receive such surgeries. Several clinical, demographic, psychological, and surgical predictors of weight loss have been reported, but these factors explain only a small fraction of the variation in weight loss after surgery. The identification of novel predictors of outcomes after metabolic and bariatric surgical procedures can both provide insight into the biological mechanisms of action of these procedures, as well as provide predictive markers that may be used to stratify those patients who may respond best to surgery or alternative treatments. Additionally, because numerous factors can affect a patient's outcomes following metabolic and bariatric surgery, and because some factors may be more relevant for some patients more than others depending on an individual's overall health and other biological characteristics, it can be difficult for medical professionals to consider and balance these factors to arrive at an accurate prediction as to how the surgery will affect a particular patient. It can be even more difficult, and likely impossible, for non-medical professionals, e.g., patients, to consider and balance such factors.

Accordingly, there remains a need for improved systems and methods for predicting metabolic and bariatric surgery outcomes and treatments that incorporate these systems and methods.

SUMMARY OF THE INVENTION

The present invention generally provides methods and compositions for treating a subject having a metabolic disorder, e.g., obesity and weight related disorders. In one embodiment, a method of treating a subject having a metabolic disorder can include the steps of (a) obtaining a biological sample from the subject; (b) evaluating the sample for the presence or absence of at least one genetic indicator, and (c) performing a first metabolic procedure on the subject, if the at least one genetic indicator is/are absent, or (d) if the at least one genetic indicator is/are present, performing a second metabolic procedure, wherein the first metabolic procedure is different from a second metabolic procedure. A genetic indicator can include a genetic variation, such as a single nucleotide polymorphism, or a level of gene expression within or without a reference range.

In one embodiment, a method of treating a weight-related disorder in a subject can include (a) obtaining a sample comprising nucleic acids from the subject; (b) evaluating the nucleic acids for an absence or presence of one or more genetic indicators; and (c) based on if the genetic indicator(s) is absent in (b), performing a first metabolic procedure, or if the genetic indicator(s) is present in (b), performing a second metabolic procedure wherein the second metabolic procedure is different from the first metabolic procedure. The first and second metabolic procedures can be surgical, such as bariatric surgery, or non-surgical. In some aspects, the biological sample includes nucleic acids and evaluating the sample includes evaluating the nucleic acids for the presence or absence of at least one genetic indicator. In an exemplary embodiment, the nucleic acids in the samples can be deoxyribonucleic acids (DNA) or ribonucleic acids (RNA). The nucleic acids can also be positive or negative for the genetic indicators. In some instances, the genetic indicators can be at least one single nucleotide polymorphism (SNP) selected from Table A (i.e., SEQ ID NOs 129-837 (SNPs identified as statistically significant for percent weight loss)), Table B (additional SNPs identified as statistically significant for percent weight loss) and/or Table C (SNPs identified as statistically significant for percent excess body weight loss). The absence or presence of the SNP can correlate with therapeutically effective weight loss of at least 20% weight change after a first metabolic procedure or a second metabolic procedure in the subject. In an exemplary embodiment, the absence or presence of the SNP can correlate with therapeutically effective weight loss of at least 20% weight change after a first metabolic procedure or a second metabolic procedure without a bariatric surgery in the subject.

In another embodiment, additional clinical measurements can be obtained from the subject. The additional clinical measurements can be obtained prior to evaluating the nucleic acids in the sample or prior to performing a first metabolic procedure or a second metabolic procedure without a bariatric surgery. In an exemplary embodiment, the additional clinical measurements can be obtained prior to evaluating the nucleic acids in the sample or prior to performing a first metabolic procedure or a second metabolic procedure without a bariatric surgery. The clinical measurement can include at least one of a pre-operative body mass index (BMI), anthropometric assessment, body composition, fat distribution, and energy expenditure assessment of the subject, a glucose tolerance or other marker of metabolic homeostasis, a bile acid profile, and a measurement of a biomarker obtained from a fluid, tissue, feces, or other sample obtained from the subject. In an exemplary embodiment, the clinical measurement is a pre-operative body mass index (BMI) of the subject. The clinical measurements can also include weight, gender, age, medical history, weight history, comorbid disease, physical activity, and/or status, BMI, ethnicity, prescription history and/or status, and types and outcomes of treatments previously tried (such as medications or other surgical and non-surgical treatments, etc). In another exemplary embodiment, the nucleic acids can be negative for the genetic indicators and the clinical measurement is a pre-operative BMI of the subject, where the BMI is greater than 25 kg/m$^2$.

In one embodiment, a method of treating a subject having a metabolic disorder can include the steps of (a) obtaining a biological sample from the subject; (b) evaluating expression of at least one gene in the sample, wherein the gene is differentially expressed after bariatric surgery or whose expression correlates with weight loss after a metabolic procedure; and (c) comparing the expression level of the gene(s) evaluated in (b) to a reference range, if expression of the gene(s) is outside the reference range, performing a first metabolic procedure on the subject, or if expression of the gene is inside the reference range, performing a second metabolic procedure on the subject. The first and second metabolic procedures can be surgical, such as bariatric surgery, or non-surgical.

In one embodiment, the gene(s) can be selected from SEQ ID NOs 1-128. The gene(s) can correlate with therapeutically significant weight loss associated with a metabolic procedure, such as bariatric surgery; improvement, alleviation or amelioration of one or more co-morbid conditions; absence of an adverse metabolic effect; and/or lack of therapeutically significant weight loss, lask of improvement, alleviation or amelioration of one or more co-morbid conditions, or an adverse metabolic event associated with bariatric surgery; or increased risk of obesity, or obesity-related co-morbid conditions in the subject. In one embodiment, expression of the gene can correlate with therapeutically significant weight loss after a metabolic procedure, such as bariatric surgery.

In some instances, the reference range of gene expression can be determined from multiple patients having undergone a metabolic procedure, such as bariatric surgery. The reference range of gene expression can be an average of gene expression from multiple patients. The reference range of gene expression can be about ±30%, ±25%, ±20%, ±15%, ±10%, or ±5% of an average of gene expression from multiple patients. These may be a group of patients that have experienced therapeutically significant weight loss associated with a metabolic procedure, such as bariatric surgery; improvement, alleviation and/or amelioration of one or more co-morbid conditions, or the absence of an adverse metabolic event. Alternatively, the group of patients may have experienced lack of therapeutically significant weight loss, lack of improvement, alleviation and/or amelioration of one or more co-morbid conditions, or an adverse metabolic event associated with a metabolic procedure, such as bariatric surgery, or an increased risk of obesity or obesity-related co-morbid conditions.

In one embodiment, the first and second metabolic procedures can be the same or different procedures. The first metabolic procedure can be a surgical procedure, such as bariatric surgery, including, but not limited to, gastric bypass, Roux-en-Y gastric bypass (RYGB), biliopancreatic diversion, partial gastrectomy procedures such as vertical sleeve gastrectomy, adjustable gastric banding, duodenal switch, duodenojejunal bypass, vertical banded gastroplasty, intragastric balloon therapy, greater curvature plication, gastric placation (including anterior and anteroposterior plication) and other forms of gastric volume reduction, Magenstrasse and Mill, ileal transposition or interposition, small bowel transposition, biliary diversion, procedures involving anastomotic connections of the gastrointestinal tract, gastric balloon implantation and other gastric or intestinal device implantation, gastric, duodenal or intestinal endoluminal barrier implantation, gastric electrical stimulation, small bowel electrical stimulation, vagal electrical stimulation, and vagal electrical inhibition. Alternatively, the first metabolic procedure can be a non-surgical procedure, such as, but not limited to, administering pharmacological and nutritional therapies, such as hormone and neuropeptide therapy, receptor agonists and antagonists, etc.; providing an alternative medical device based therapy, such as, but not limited to, gastric balloon implantation and other gastric or intestinal device implantation, gastric, duodenal or intestinal endoluminal barrier implantation, etc.; and/or the activation of brown adipose tissue.

As mentioned above, the second metabolic procedure can be the same as or different from the first metabolic procedure. In one embodiment, the first metabolic procedure can be different from the second metabolic procedure. For example, the first metabolic procedure can be a surgical procedure, such as bariatric surgery, and the second metabolic procedure can be non-surgical. In another example, the first metabolic procedure can be a surgical procedure, and the second metabolic procedure can be a different surgical procedure. In one embodiment, the first metabolic procedure can be a non-surgical procedure and the second metabolic procedure can be a surgical procedure.

In another embodiment, a clinical measurement can be obtained from the subject. The clinical measurement can be obtained prior to or after obtaining a biological sample from the subject, prior to or after comparing the expression level of the gene(s), or prior to performing a first metabolic procedure or second metabolic procedure. The clinical measurement can include at least one of a pre-operative body mass index (BMI), a glucose tolerance, bile acid profile, and body composition/fat distribution of the subject. In an exemplary embodiment, the clinical measurement is a pre-operative body mass index (BMI) of the subject. The clinical measurement can also include weight, gender, age, medical history and/or status, ethnicity, medical, prescription history and/or status, and types of treatments previously tried (such as medications or other surgical and non-surgical treatments, etc.). In another exemplary embodiment, the nucleic acids can be negative for the genetic indicators and the clinical measurement is a pre-operative BMI of the subject, where the BMI is greater than 23 kg/m$^2$.

In one aspect, diagnostic kits are disclosed for assessing the presence of a single nucleotide polymorphism (SNP) shown in Table A (SEQ ID NOs. 129-837), Table B, and/or Table C in a sample. The kit can include, but is not limited to, a pair of primers that specifically hybridize to regions proximal to the SNP selected from Table A (SEQ ID NOs. 129-837), Table B, and/or Table C and reagents for polymerase chain reaction (PCR). The kit can also include reagents for preparation, isolation and/or purification of nucleic acids from a sample. The kit can also be used in a method having the steps of (a) obtaining a sample comprising nucleic acids, such as deoxyribonucleic acids (DNA), from the subject; (b) evaluating the nucleic acids for an absence or presence of one or more genetic indicators; and if the genetic indicator(s) is absent in (b), performing a first metabolic procedure, such as a bariatric surgery, or if the genetic indicator(s) is present in (b), performing a second metabolic procedure, wherein the second metabolic procedure is different from the first metabolic procedure. In an exemplary embodiment, the second metabolic procedure can exclude bariatric surgery.

In another aspect, a method of treating obesity or a weight-related disorder in a subject is disclosed. The method can include (a) obtaining a sample comprising nucleic acids from the subject; (b) evaluating the nucleic acids for an absence or presence of one or more genetic indicators; (c) predicting an outcome of performing a first metabolic procedure based on the absence or presence of the genetic indicator(s); and (d) performing the first metabolic procedure or performing an alternative second metabolic procedure based on the predicted outcome. For example, the method can include (a) obtaining a sample comprising nucleic acids from the subject; (b) evaluating the nucleic acids for an absence or presence of one or more genetic indicators; (c) predicting an outcome of performing a first metabolic procedure, such as a bariatric surgery, based on the absence or presence of the genetic indicator(s); and (d) performing the first metabolic procedure or performing an alternative second metabolic procedure. In an exemplary embodiment, the alternative second metabolic procedure can exclude bariatric surgery.

In one embodiment, the nucleic acids in the samples can be deoxyribonucleic acids (DNA) or ribonucleic acids (RNA). The nucleic acids can also be positive or negative for the genetic indicators. In some instances, the genetic indicators can be at least one single nucleotide polymorphism (SNP) selected from Table A (SEQ ID NOs 129-837), Table B, and/or Table C that can be absence or presence in the nucleic acids.

In another embodiment, the outcome predicted from performing the metabolic procedure can be a therapeutically effective weight loss and/or the outcome can be an amelioration of or reduction of at least one weight-related co-morbid condition. In some embodiments when the outcome is a therapeutically effective weight loss, the weight loss can be at least 20% weight change. The outcome can also be a therapeutically effective weight loss when the genetic indicator(s) is absent. The outcome can further be a therapeutically effective weight loss and the metabolic procedure can be performed in the absence of the genetic indicator(s). In some embodiments, the outcome predicted from performing the metabolic procedure can be lack of therapeutically significant weight loss or an adverse metabolic event associated with bariatric surgery, increased risk of obesity, or obesity-related co-morbid conditions in the subject. lack of therapeutically significant weight loss, lask of improvement, alleviation or amelioration of one or more co-morbid conditions, or an adverse metabolic event associated with bariatric surgery; or increased risk of obesity, or obesity-related co-morbid conditions in the subject.

In yet another embodiment, the outcome predicted from performing the metabolic procedure can be an amelioration of or reduction of at least one weight-related co-morbid condition. The co-morbid condition can be at least one of hypertension, dyslipidemia, triglyceride levels, diabetes, gastroesophageal reflux, fatty liver disease, steatohepatitis, heart or vascular disease, heart failure, cardiovascular risk, sleep apnea, Barrett's esophagus, asthma, osteoarthritis, compression fractures, gallstones, lymphedema, urinary incontinence, stroke, cognitive dysfunction, pseudotumor cerebri, inflammatory diseases, autoimmune diseases, gout, polycystic ovarian syndrome, infertility, depression, anxiety and/or panic disorders, cognitive or other neurological disorders, cancer risk and mortality (cancers including adenocarcinoma of pancreas, esophagus, gallbladder, pancreas, colon, rectum, breast, prostate; cervical carcinoma, endometrial carcinoma, ovarian carcinoma, renal cell carcinoma, non-Hodgkins lymphoma), weight regain, excess weight loss, nutritional deficiency, constipation, diarrhea, marginal ulceration, dumping syndrome, reactive hypoglycemia, beta cell hyperfunction, gastrointestinal stenosis, liver disorders, nausea/vomiting and/or other metabolic syndromes.

In yet another aspect, predicting the outcome can include inputting the subject's data into a metabolic procedure outcome prediction system. The metabolic procedure outcome prediction system can be an interactive interface for modeling metabolic procedure outcomes, such as bariatric surgery outcomes. Examples of patient data that can be used for predicting outcomes can include the evaluation of the absence or presence of the genetic indicator(s), and at least one clinical measurement including a pre-operative body mass index (BMI), a glucose tolerance, bile acid profile, and body composition/fat distribution of the subject, or another measurement of gene expression in a cell or tissue, measurement of a peptide, protein, metabolite or other compound in blood or in a cell or in a tissue.

In another aspect, a method of treating a metabolic disorder in a subject is disclosed. The method can include measuring expression of the gene(s) in a sample from the subject; comparing the expression level of the gene(s) to a reference range of expression of the gene, wherein the reference range is determined from multiple patients having undergone a bariatric surgery; and administering to the subject a composition that modulates expression of the gene(s) to mimic the expression after bariatric surgery, thereby treating the metabolic disorder. The method can result in a therapeutically significant weight loss. The method can also result in a therapeutically significant weight loss that is at least a 20% body weight change or an amelioration of or reduction of at least one weight-related co-morbid condition, where the co-morbid condition can be hypertension, dyslipidemia, triglyceride levels, diabetes, gastroesophageal reflux, fatty liver disease, steatohepatitis, heart or vascular disease, heart failure, cardiovascular risk, sleep apnea, Barrett's esophagus, asthma, osteoarthritis, compression fractures, gallstones, lymphedema, urinary incontinence, stroke, cognitive dysfunction, pseudotumor cerebri, inflammatory diseases, autoimmune diseases, gout, polycystic ovarian syndrome, infertility, depression, anxiety and/or panic disorders, cognitive or other neurological disorders, cancer risk and mortality (cancers including adenocarcinoma of pancreas, esophagus, gallbladder, pancreas, colon, rectum, breast, prostate; cervical carcinoma, endometrial carcinoma, ovarian carcinoma, renal cell carcinoma, non-Hodgkins lymphoma), weight regain, excess weight loss, nutritional deficiency, constipation, diarrhea, marginal ulceration, dumping syndrome, reactive hypoglycemia, beta cell hyperfunction, gastrointestinal stenosis, liver disorders, nausea/vomiting and/or other metabolic syndromes.

In yet another aspect, kits are disclosed for assessing expression of at least one gene associated with response to a metabolic procedure in a sample. In yet another aspect, kits are disclosed for assessing the sequence of a gene or other chromosomal DNA. The kit can include, but is not limited to, a pair of primers that specifically hybridize to an expression product of the gene(s) selected from SEQ ID NOs 1-128. The kit can also include reagents for preparation, isolation and/or purification of nucleic acids and/or expression products from a sample.

BRIEF DESCRIPTION OF THE DRAWINGS

The invention will be more fully understood from the following detailed description taken in conjunction with the accompanying drawings, in which:

FIG. 5 is a bar graph showing final weights obtained at 1 year postoperative of the 848 patients after 1 year postoperative;

FIG. 6 is a bar graph showing the change in body mass index (BMI) of the 848 patients after 1 year postoperative with patients in lower BMI groups having significantly less change in BMI;

DETAILED DESCRIPTION OF THE INVENTION

Figure 1:
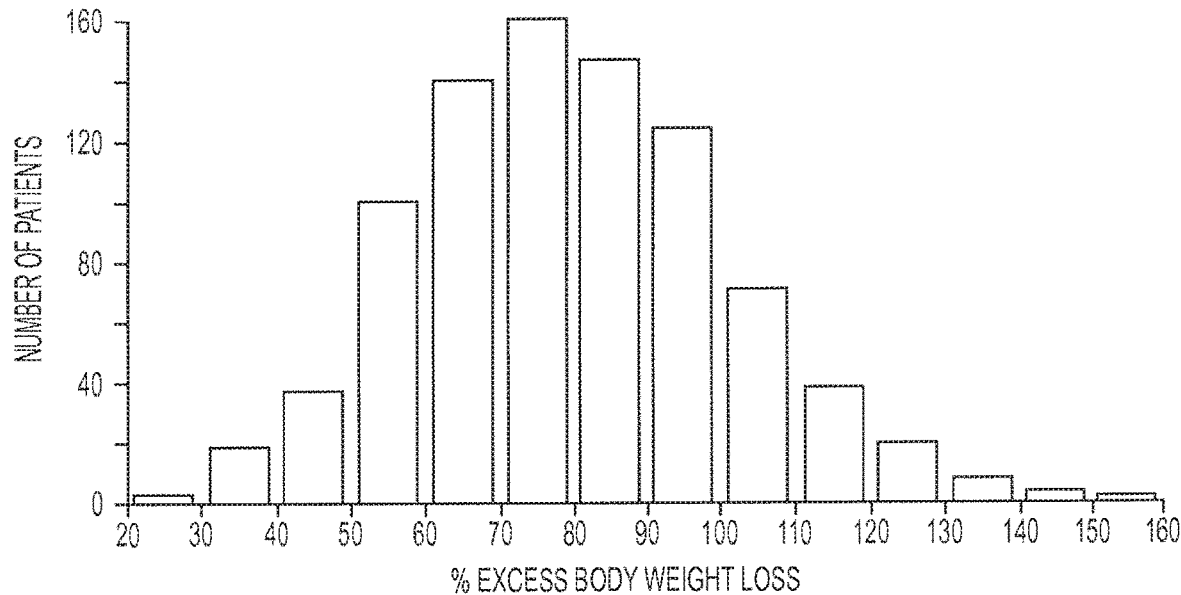
FIG. 1 is a bar graph showing the excess body weight loss (EBWL) at postoperative weight nadir (achieved after at least 10 months of surgery without coexisting debilitating illness or use of weight lowering medications) after Roux-en-Y gastric bypass (RYGB) in 848 patients with severe obesity.

Certain exemplary embodiments will now be described to provide an overall understanding of the principles of the structure, function, manufacture, and use of the therapeutics and methods disclosed herein. One or more examples of these embodiments are illustrated in the accompanying drawings. Those skilled in the art will understand that the therapeutics and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

SEQ ID NOs 1-128 in the present application correspond to SEQ ID NOs 1-128 of U.S. Provisional Application Ser. No. 61/740,678, and SEQ ID Nos: 129-837 correspond to the sequences from Table A of U.S. Provisional Application Ser. No. 61/704,434 (which is identical to Table A of the present application).

Metabolic Disorders (Obesity and Other Weight-Related Disorders)

Methods and kits are provided to evaluate genetic indicators, such as by identifying genetic indicators, and/or measuring and assessing gene expression for treatment of obesity and/or weight-related disorders. It has been discovered that genetic indicators, such as single nucleotide polymorphisms, can be indicators for weight loss potential after metabolic surgery, such as bariatric surgery. Given the correlation between weight loss and improvements in comorbidities associated with excess weight, these genetic predictors can be indicators or predictors of improvements in comorbid conditions after bariatric surgery. It has also been discovered that certain genes demonstrate differential gene expression after a metabolic procedure, such as bariatric surgery. It has been further discovered that a correlation exists between the weight loss and other improvements in comorbidities and gene expression of certain genes. Therefore, modulating certain gene expression can be therapeutic to improve comorbid conditions after bariatric surgery. Further, the gene expression can serve a surrogate marker for whether a surgical procedure (e.g., bariatric surgery) is likely to lead to a successful outcome, or an alternative procedure is better suited for a certain patient or patient population. Therefore, the invention disclosed is generally directed to therapeutic methods and compositions for treating metabolic disorders, such as obesity and/or other weight-related disorders, in a subject by (1) evaluating genetic indicators, such as by evaluating the subject's deoxyribonucleic acids (DNA) for a presence or absence of one or more genetic indicators, and/or evaluating gene expression in the subject for an overexpression or an underexpression of one or more specific genes associated with metabolic disorders.

Weight loss can be characterized using a number of different metrics, including the absolute number of pounds or body mass index (BMI) points lost, weight or BMI achieved after weight loss, the percent of baseline weight or BMI lost (% weight change (WC)), and percent excess body weight lost (% EBWL).

The phrase "weight-related disorder" as used herein, refers to disorders, diseases, and conditions that are caused or characterized by abnormal energy use or consumption leading to excessive weight gain or loss, altered responses to ingested or endogenous nutrients, energy sources, hormones or other signaling molecules within the body or altered metabolism of carbohydrates, lipids, proteins, nucleic acids or a combination thereof. A weight-related disorder can be associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 or other neurotransmitters in the brain, spinal cord, peripheral or enteric nervous systems) or the like. Some non-limiting examples of weight-related disorders can be obesity, diabetes, including type II diabetes, insulin-deficiency, insulin-resistance, insulin-resistance related disorders, glucose intolerance, syndrome X, inflammatory and immune disorders, dyslipidemia, metabolic syndrome, non-alcoholic fatty liver, abnormal lipid metabolism, obstructive sleep apnea, asthma, autoimmune and inflammatory disorders, cancer, cognitive and neurodegenerative disorders, hypertension, high cholesterol, anxiety, congestive heart failure, ischemic heart disease, GERD, atherogenic dyslipidemia, hyperlipidemic conditions such as atherosclerosis, hypercholesterolemia, and other coronary artery diseases in mammals, and other disorders of metabolism.

As used herein, the term "obesity" or "obese" typically refers to a non-Asian individual having a body mass index (BMI) of $\geq 30$ kg/m$^2$ or $\geq 27$ kg/m$^2$ in Asian individuals and "overweight" typically refers to a non-Asian individual having a body mass index (BMI) of $\geq 25$ kg/m$^2$ or $\geq 23$ kg/m$^2$ in Asian individuals. BMI is a measure expressing the relationship (or ratio) of weight-to-height based on a mathematical formula in which a person's body weight in kilograms is divided by the square of his or her height in meters (i.e., wt/(ht)$^2$). Individuals having BMI of $\geq 25$ kg/m$^2$ in non-Asians or $\geq 23$ kg/m$^2$ in Asians have a substantially increased risk of at least one weight-related co-morbid condition or having a metabolic disorder or syndrome. As used herein, the terms "co-morbidity" or "co-morbid condition" typically refers to, but is not limited to, hypertension, dyslipidemia, triglyceride levels, diabetes, gastroesophageal reflux, fatty liver disease, steatohepatitis, heart or vascular disease, heart failure, cardiovascular risk, sleep apnea, Barrett's esophagus, asthma, osteoarthritis, compression fractures, gallstones, lymphedema, urinary incontinence, stroke, cognitive dysfunction, pseudotumor cerebri, inflammatory diseases, autoimmune diseases, gout, polycystic ovarian syndrome, infertility, depression, anxiety and/or panic disorders, cognitive or other neurological disorders, cancer risk and mortality (cancers including adenocarcinoma of pancreas, esophagus, gallbladder, pancreas, colon, rectum, breast, prostate; cervical carcinoma, endometrial carcinoma, ovarian carcinoma, renal cell carcinoma, non-Hodgkins lymphoma), weight regain, excess weight loss, nutritional deficiency, constipation, diarrhea, marginal ulceration, dumping syndrome, reactive hypoglycemia, beta cell hyperfunction, gastrointestinal stenosis, liver disorders, nausea/vomiting and/or other metabolic syndromes. As the name suggests, "metabolic disorder or syndrome" is tied to the body's metabolism, and more likely to conditions that influence metabolism, such as insulin resistance. Metabolic disorder or syndrome can also be characterized by excess body fat, atherogenic dyslipidemia, elevated blood pressure and insulin resistance, among others.

Other weight-related disorders can include conditions that occur or cluster together, and/or increase the risk for heart disease, stroke, diabetes, and obesity. Having just one of these conditions such as increased blood pressure, elevated insulin levels, excess body fat around the waist or abnormal cholesterol levels can increase the risk of the above mentioned diseases. In combination, the risk for coronary heart disease, stroke, insulin-resistance syndrome, and diabetes is even greater.

The increasing prevalence of obesity in the population has led to a parallel rise in metabolic procedures, like bariatric surgery, as a treatment for obesity and related comorbid conditions. As used herein, the term "metabolic procedures" can include surgical and nonsurgical procedures. Surgical procedures can achieve a sustained weight reduction of up to 70% of excess body weight in the majority of patients, and are often more effective than nonsurgical approaches. Non-limiting examples of surgical procedures can include bariatric surgery. As used herein, "bariatric surgery" generally refers and can include procedures often referred to as metabolic surgery or therapy, as well as a variety of procedures performed in a subject that leads to a physiologic improvement in energy balance, nutrient utilization, or metabolic disorders. These procedures often, but not always, result in weight loss. Bariatric surgery refers to a surgical procedure to alter gastrointestinal structure or function so as to affect body weight, body composition, or energy balance regulation or otherwise alter metabolic function. Some non-limiting examples of bariatric surgery can be any form of gastric bypass, Roux-en-Y gastric bypass (RYGB), biliopancreatic diversion, partial gastrectomy procedures such as vertical sleeve gastrectomy, adjustable gastric banding, duodenal switch, duodenojejunal bypass, vertical banded gastroplasty, intragastric balloon therapy, greater curvature plication, gastric plication (including anterior and anteroposterior plication) and other forms of gastric volume reduction, Magenstrasse and Mill, ileal transposition or interposition, small bowel transposition, biliary diversion, procedures involving anastomotic connections of the gastrointestinal tract (e.g., jejunoileostomy, etc.), gastric electrical stimulation, small bowel electrical stimulation, vagal electrical stimulation, vagal electrical inhibition, and variations of the procedures above as well as other methods known by those skilled in the art. Metabolic procedures can also include non-surgical procedures including, by way of non-limiting examples, administering pharmacological and nutritional therapies, such as hormone and neuropeptide therapy, receptor agonists and antagonists, etc.; providing an alternative medical device based therapy, such as, but not limited to, gastric balloon implantation and other gastric or intestinal device implantation, gastric, duodenal or intestinal endoluminal barrier implantation, etc.; and/or the activation of brown adipose tissue. Each of the surgical and non-surgical procedures may be performed alone or in addition to other treatments.

It has been discovered that subjects with certain diagnostic markers respond to therapeutic interventions, such as gastric bypass surgery. Therefore, in an exemplary embodiment, a method of treating a metabolic disorder, such as obesity, in a subject can include obtaining a sample with DNA from the subject, evaluating the DNA for the presence or absence of one or more genetic indicators and performing a first metabolic procedure, such as bariatric surgery or a second metabolic procedure, excluding bariatric surgery, depending on the absence or presence of one or more genetic indicators.

It has also been discovered that expression of certain genes is associated with a better response to therapeutic interventions, such as gastric bypass surgery. Therefore, in an exemplary embodiment, a method of treating a metabolic disorder in a subject can include obtaining a sample from the subject, evaluating the sample for expression of at least one gene (wherein the gene is shown to be differentially expressed after bariatric surgery or wherein expression of the gene correlates with weight loss after a metabolic procedure), and performing a first metabolic procedure or a second metabolic procedure excluding a bariatric surgery depending on the expression of gene(s).

Differentially Expressed Genes and Genetic Indicators

Identification of specific genetic indicators, such as SNPs associated with weight loss after RYGB, or expression patterns, such as expression of genes associated with weight loss after RYGB, may both enhance the understanding of the mechanisms of weight loss as well as help identify those patients for whom bariatric surgery procedures are most effective.

As used herein, "polymorphism" refers to a variation in the sequence of a gene in the genome amongst a population, such as allelic variations and other variations that arise or are observed. "Genetic polymorphisms" refers to the variant forms of DNA sequences that can arise as a result of nucleotide alteration or substitution, deletion, insertion, rearrangement or duplication, for example. Thus, a polymorphism refers to the occurrence of two or more genetically determined alternative sequences or alleles in a population. These polymorphisms can occur in coding and non-coding portions of the genome, and can be manifested or detected as differences in nucleic acid sequences, gene expression, and/or other differences in mRNA structure and function, including, for example transcription, processing, translation, transport, protein processing, trafficking, DNA synthesis, expressed proteins, other gene products or products of biochemical pathways or in post-translational modifications and any other differences manifested among members of a population. A "single nucleotide polymorphism" or "SNP" refers to a polymorphism that arises as the result of a single base change, such as an insertion, deletion or change in a base.

A polymorphic marker or site is the locus at which divergence occurs. Such a site may be as small as one base pair (an SNP). Polymorphic markers include, but are not limited to, restriction fragment length polymorphisms, copy number variations, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu.

Polymorphic forms also are manifested as different mendelian alleles for a gene. The genomes of all organisms undergo spontaneous mutation in the course of their continuing evolution, generating variant forms of progenitor genetic sequences. A variant form may confer differences in proteins, protein modifications, RNA expression, RNA modification, DNA and RNA methylation, regulatory factors that alter gene expression and DNA replication, and any other manifestation of alterations in genomic nucleic acid or organelle nucleic acids.

As used herein, an "isolated" nucleic acid molecule, such as a nucleic acid molecule containing a SNP genetic indicator or an expression product of a gene or other transcript (e.g., messenger RNA, microRNA or other non-coding RNA), can be substantially free of other cellular material, or culture medium when produced by recombinant techniques, or chemical precursors or other chemicals when chemically synthesized. A nucleic acid molecule can be fused to other coding or regulatory sequences and still be considered "isolated." Nucleic acid molecules present in non-human transgenic animals, which do not naturally occur in the animal, are also considered "isolated." For example, recombinant DNA molecules contained in a vector are considered "isolated." Further examples of "isolated" DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

A nucleic acid molecule can include one or more SNPs with flanking nucleotide sequences on either side of the SNPs. A flanking sequence can include nucleotide residues that are naturally associated with the SNP site and/or heterologous nucleotide sequences. Preferably the flanking sequence can be up to about 500, 300, 100, 60, 50, 30, 25, 20, 15, 10, 8, or 4 nucleotides (or any other length in between) on either side of a SNP.

As used herein, an "isolated protein," once expressed, can be isolated by lysing cells and applying standard protein isolation techniques to the lysates or the pellets. Monitoring the purification process can be accomplished by using Western blot techniques or radioimmunoassay or other standard immunoassay techniques.

As used herein, an "amplified polynucleotide" can include a nucleic acid molecule containing one or more SNPs or a gene that can be replicated by at least two fold through any nucleic acid amplification method performed in vitro. In one embodiment, an amplified polynucleotide is the result of at least a ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified DNA template, but the precise amount of amplification needed for an assay depends on the sensitivity of the subsequent detection method used.

A subject or patient may be homozygous or heterozygous for an allele at each SNP position. A SNP can, in some instances, be referred to as a "cSNP" to denote that the nucleotide sequence containing the SNP is an amino acid coding sequence. While SNPs can be bi-, tri-, or tetra-allelic, the vast majority of the SNPs are bi-allelic, and are thus often referred to as "bi-allelic markers," or "di-allelic markers."

As used herein, references to "SNPs" and SNP genotypes include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases. An "allele" is an alternative form or variation in a DNA sequence. Many SNPs have only two alleles: minor and major alleles. SNPs are routinely used in SNP-based genetic linkage analysis to map a disease to a particular locus, the position of a gene (or SNP) on a chromosome.

Methods and kits are provided to identify genetic indicators and/or evaluate and assess expression of genes associated with response to a metabolic procedure, such as bariatric surgery, for treatment of metabolic disorders. It has been discovered that genetic indicators, such as single nucleotide polymorphisms, and gene expression, such as genes associated with response to a metabolic procedure, can indicate weight loss potential after the metabolic procedure, such as bariatric surgery. By obtaining a sample from a subject and extracting nucleic acids from or analyzing gene expression in the sample, response to the metabolic procedure, e.g. weight loss potential after the bariatric surgery, can be predicted and/or assessed.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human. In an exemplary embodiment, the subject is a patient.

The term "sample" is intended to include tissues, cells, fluids and biological samples isolated from a subject, as well as tissues, cells and fluids present within a subject. The sample can be a tissue sample, such as from an organ, or fluid, ascites, and any other sample that is used by those familiar with the art. The sample can be derived from any source which contains proteins or expression products and/or nucleic acids, DNA (e.g., chromosomal nucleic acids) or RNA, such as a blood sample, body excrements such as semen, saliva, stool, urine, amniotic fluid and so forth, sample of cerebrospinal fluid, or tissue sample from skin, muscle, buccal or conjunctival mucosa, placenta, gastrointestinal tract or other organs. A sample of proteins and/or nucleic acid from fetal cells or tissue can be obtained by appropriate methods, such as by amniocentesis or chorionic villus sampling (direct or cultured). In one aspect, the sample can be a biopsy sample or a small number of cells or a tissue sample removed for processing. Common examples of biopsy methods can include, but are not limited to, oral swab, brush cytology, core needle biopsy, surgical biopsy, punch biopsy, shave biopsy, incisional/excisional biopsy and curettage biopsy.

In some embodiments, the sample of cells or tissue sample can be obtained from the subject by biopsy or surgical resection. A sample of cells, tissue, or fluid can be removed by needle aspiration biopsy. For this, a fine needle attached to a syringe is inserted through the skin and into the organ or tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue can be removed from the region of interest. CT imaging, ultrasound, or endoscopy can be used to guide this type of biopsy.

Once a sample of cells or sample of tissue is removed from the subject, it may be processed for the isolation of RNA or protein using techniques well known in the art and disclosed in standard molecular biology reference books. A sample of tissue may also be stored in RNAlater (Ambion; Austin, Tex.) or flash frozen and stored at −80° C. for later use. The tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

Direct assessment for the presence of the genetic identifiers or for gene expression can be performed on a sample without processing to isolate nucleic acids or gene expression products. Alternatively, a sample can be processed to enhance access to gene expression products, nucleic acids, or copies of nucleic acids (e.g., amplification of nucleic acids), and the processed sample can then be used to assess for the presence of the genetic identifiers or for gene expression. For example, in one embodiment, cDNA is prepared from a sample comprising mRNA, for use in the methods. The mRNA can be isolated from the sample and converted into cDNA. Alternatively or in addition, if desired, an amplification method can be used to amplify nucleic acids for use as the test sample in the assessment for the presence or absence of a genetic identifier(s) or for gene expression. The nucleic acids can be isolated from the samples or can be processed and analyzed within the sample.

Nucleic acids, including RNA, DNA, or cDNA, proteins or other expression products can be analyzed for the genetic indicator(s) or measured to determine gene expression from a sample. The presence of genetic indicator(s) or gene expression can be evaluated in nucleic acids or proteins in vitro, in situ, as well as in vivo. For example, in vitro techniques for detection of genetic indicator(s) in mRNA or for measuring expression can include assays such as ELISA assay and Western blot analysis, immunocytochemical assays, assessment of mRNA in PCR, q-PCR, northern hybridizations and in situ hybridizations, assessment of cDNA in Southern hybridizations, PCR, quantitative PCR (qPCR), and introduction of labeled nucleic acids for incorporation into the nucleic acids, for example, the radiolabeled nucleic acids whose presence and location in a subject can be detected by standard imaging techniques.

Another embodiment for identifying genetic indicators in RNA or DNA or for measuring gene expression can include the use of a labeled nucleic acid probe capable of hybridizing to a mRNA or cDNA. A wide variety of conventional techniques are available, including mass spectrometry, chromatographic separations, 2-D gel separations, microarrays, binding assays (e.g., immunoassays), competitive inhibition assays, one- and two-dimensional gels and sandwiched ELISA. Typical methodologies for RNA detection include RNA extraction from a cell or tissue sample, followed by hybridization of a labeled probe, (e.g., a complementary polynucleotide) specific for the target RNA to the extracted RNA, and detection of the probe (e.g., Northern blotting), direct sequencing, gel electrophoresis, column chromatography, and quantitative PCR.

Primers based on a nucleotide sequence specific for one or more of the genetic indicators or genes can be used to analyze the presence or absence in or to measure expression of the corresponding gene(s) or genetic indicator(s). In some embodiments, a primer pair can be designed by utilizing primer design software, such as GenScript, Primer3, PRIDE and Primer Express. Commercial primers are also available for purchase corresponding to multiple locations throughout the gene. The primers can be at least 5, 6, 7, 8, 9, 10, 11, 12, 13, 14, 15, 20, 25, 30, 35, or 40 basepairs in length. In an exemplary embodiment, the primers can be at least 10 basepairs in length. The primers can also hybridize to a region of nucleic acids (mRNA, cDNA or genomic DNA) proximal or in the vicinity of the genetic indicator or the gene.

The primer can be similar (sufficiently similar or identical to hybridize to the sequence) or complementary (sufficiently similar or identical to hybridize to the complement sequence) to a nucleic acid sequence upstream or downstream from the genetic indicator. The primer can hybridize to a sequence that is at least 50, 60, 70, 80, 90, 100, 110, 120, 130, 140, 150, 160, 170, 180, 190, 200, 250, 300, 350, 400, 450, 500, 550, 600, 650, 700, 750, 850, 900, 950, 1000 basepairs or more or any number of basepairs in between from the genetic indicator. In one embodiment, the primers can specifically hybridize to a region proximal to one or more genetic indicators (such as a single nucleotide polymorphism (SNP) as shown in Table A (SEQ ID NOs 129-837), Table B, or Table C). In an exemplary embodiment, the primers can be complementary to a nucleic acid sequence of at least 10 bases found at least 200 basepairs or more from the genetic indicator.

The primer can be similar (sufficiently similar or identical to hybridize to the sequence) or complementary (sufficiently similar or identical to hybridize to the complement sequence) to a nucleic acid sequence of the gene. In one embodiment, the primers can be specific for at least one of SEQ ID NOs 1-128. See Table 10 for correspondence of SEQ ID NO to gene name/description and accession number.

Diagnostic kits and/or devices are also included. The diagnostic kit and/or device can include, but is not limited to, sample collection materials (storage solutions and collection apparatus such as swab, biopsy needle, blood/body fluid needle, brush, etc), protein, DNA or RNA extraction and isolation materials (solutions and enzymes for performing such procedures); nucleic acid amplification materials (solutions, enzymes and primers specific for the genetic indicator(s) or primers for performing such procedures); and sequencing materials (solutions, enzymes and gene specific primers for performing such procedures). The diagnostic kit and/or device can include any of the above and exclude any materials from the above. In an exemplary embodiment, the diagnostic kit and/or device can include DNA polymerase chain reaction amplification solutions and/or enzymes and at least one set of primers specific for a genetic indicator. In another exemplary embodiment, the diagnostic kit and/or device can include DNA polymerase chain reaction amplification solutions and/or enzymes and at least one set of gene specific primers.

In one aspect, a method of treating obesity or weight-related disorders includes evaluating DNA for the absence or presence of one or more genetic indicators, such as SNPs. The DNA can be positive or negative for one or more indicators. A DNA sample from a subject can be evaluated for the presence or absence of the genetic indicator(s). In some instances, the DNA can be negative for the indicator(s) and the pre-operative BMI can be greater than 20 kg/m$^2$.

Also, the presence or absence of the genetic indicator(s) can correlate with therapeutically effective weight loss associated with bariatric surgery; improvement, alleviation or amelioration of one or more co-morbid conditions; and/or lack of therapeutically effective weight loss associated with bariatric surgery, increased risk of obesity or obesity-related co-morbid conditions in the subject.

In one embodiment, the presence or absence of the genetic indicator(s) can correlate with therapeutically effective weight loss after bariatric surgery in the subject. Therapeutically effective weight loss can be characterized by loss of at least 20%, 25%, 30%, 35%, 40%, 45%, 50%, 60%, 65%, 70%, 75%, 80%, 85% or more of excess body weight. Therapeutically effective weight loss can also be characterized as at least 10%, 15%, 20%, 25%, 30%, 35%, 40%, 45%, 50%, 60%, 65%, 70%, 75%, or more weight change. Alternatively or in addition to, therapeutically effective weight loss can be characterized by change of at least 20%, 25%, 30%, 35%, 40%, 45%, 50%, 60%, 65%, 70%, 75%, 80%, 85% or more of body mass index. Excess body weight, weight change, and/or body mass index measurements can be determined by taking the measurement of the subject prior to treatment or preoperatively and compare the measurement to another measurement taken at a time point after treatment or surgery. The time point for taking the measurement can be 1, 3, 6, 9, 12, 18, 24, 36, 48, 72, 84, 96, 108, 120 months post treatment or postoperative or any number of months in between. In an exemplary embodiment, the therapeutically effective weight loss is at least 20% weight change after bariatric surgery or alternative treatment in the subject.

Also, the presence or absence of one or more genetic indicator(s) can correlate with improvement, alleviation or amelioration of one or more co-morbid conditions in the subject. The presence or absence of the genetic indicator(s) can correlate with, for example, reduced hypertension, reduced dyslipidemia, improvement or alleviation of diabetes, reduced acid reflux, alleviation of fatty liver or steatohepatitis, reduced risk of heart disease, alleviation of depression, alleviation of sleep apnea, alleviation of asthmatic symptoms, alleviation of arthritis, reduced risk of compression fractures, reduced occurrence of gallstones, lymphoedema, alleviation of urinary incontinence, reduced risk of stroke, reduced risk of cancer and/or reduced risk of other metabolic syndromes.

Alternatively, the presence or absence of one or more genetic indicator(s) can correlate with lack of therapeutically effective weight loss associated with bariatric surgery or increased risk of obesity, or obesity-related co-morbid conditions in the subject. The presence or absence of the genetic indicator(s) can correlate with, for example, lack of weight loss after bariatric surgery, increased hypertension, risk of dyslipidemia, development of diabetes, acid reflux, fatty liver disease or steatohepatitis, heart disease, depression, sleep apnea, asthmatic symptoms, arthritis, compression fractures, gallstones, lymphoedema, urinary incontinence, stroke, cancer and/or risk of other metabolic syndromes.

The genetic indicators can be single nucleotide polymorphisms that occur in coding and non-coding portions of the genome, and can be manifested or detected as differences in nucleic acid sequences (DNA), gene expression products (RNA and proteins), including, for example transcripts (mRNA, miRNA, and others), proteins, other gene products or products of biochemical pathways or in post-translational modifications and any other differences manifested among members of a population. In one embodiment, one or more genetic indicators are absent from the subject's nucleic acid sample, such as DNA, where at least one genetic indicator is a single nucleotide polymorphism (SNP) shown in Table A (SEQ ID NOs 129-837), Table B, and/or Table C. In another embodiment, one or more genetic indicators are present in the subject's nucleic acid sample, such as DNA, where at least one genetic indicator is a single nucleotide polymorphism (SNP) shown in Table A (i.e, SEQ ID NOs 129-837 (SNPs identified as statistically significant for percent weight loss)), Table B (additional SNPs identified as statistically significant for percent weight loss) or Table C (SNPs identified as statistically significant for percent excess body weight loss). Each SNP sequence is associated with a unique accession number (e.g., rs number) that is available in the Single Nucleotide Polymophism Database hosted by the National Center for Biotechnology Information (NCBI) to identify the genetic variation and sequence information. In yet another embodiment, one or more genetic indicators are absent from the subject's nucleic acid sample, such as DNA, and one or more different genetic indicators are present in the subject's DNA sample, where at least one genetic indicator is a single nucleotide polymorphism (SNP) shown in Table A (SEQ ID NOs 129-837), Table B, or Table C.

For example, the genetic indicator(s) can be at least one single nucleotide polymorphism (SNP) shown in Table A (SEQ ID NOs 129-837), Table B, or Table C. Selected genetic indicators, such as the SNPs shown in Table A (SEQ ID NOs 129-837), Table B, or Table C, can be positive or negative indicators for successful obesity or weight-related disorder treatment. In one embodiment, the genetic indicator can be one or more SNPs shown in Table A (SEQ ID NOs 129-837), Table B, or Table C, such as SEQ ID NO 129-SEQ ID NO 138, SEQ ID NO 129-SEQ ID NO 148, SEQ ID NO 129-SEQ ID NO 158, SEQ ID NO 129-SEQ ID NO 168, SEQ ID NO 129-SEQ ID NO 178, SEQ ID NO 129-SEQ ID NO 188, SEQ ID NO 129-SEQ ID NO 198, SEQ ID NO 129-SEQ ID NO 208, SEQ ID NO 129-SEQ ID NO 218, SEQ ID NO 129-SEQ ID NO 228, SEQ ID NO 129-SEQ ID NO 328, SEQ ID NO 129-SEQ ID NO 428, SEQ ID NO 129-SEQ ID NO 528, SEQ ID NO 129-SEQ ID NO 628, SEQ ID NO 129-SEQ ID NO 728, SEQ ID NO 129-SEQ ID NO 828, SEQ ID NO 129-837, SEQ ID NO 129-SEQ ID NO 928, SEQ ID NO 129-SEQ ID NO 1028, SEQ ID NO 129-SEQ ID NO 1128, SEQ ID NO 129-SEQ ID NO 2128, SEQ ID NO 129-SEQ ID NO 3128, SEQ ID NO 129-SEQ ID NO 4128, SEQ ID NO 129-SEQ ID NO 5128, etc. In another embodiment, the genetic indicator can be one or more SNPs shown in Table A (SEQ ID NOs 129-837), Table B, or Table C, as identified by the unique SNP identifier (e.g. rs number). In another embodiment, the genetic indicator can be one or more SNPs located on chromosome 6, chromosome 11, and/or chromosome 15. In yet another embodiment, the genetic indicators are one or more SNPs selected from rs7158359, rs7129556, rs10899387, rs934760, rs1104959, rs17702901, rs588217 and rs9357419. In an exemplary embodiment, at least one genetic indicator can be located on chromosome 15. In another exemplary embodiment, the at least one genetic indicator can be located within a cluster or cloud of SNPs within a region of a chromosome that may be in linkage disequilibrium with one another. The genetic indicator(s) can include one or more SNPs within the cloud and/or all the SNPs within the cloud. The genetic indicator(s) can also include one or more SNPs in linkage disequilibrium. In yet another exemplary embodiment, at least one genetic indicator is rs17702901. At least one genetic indicator can be rs17702901 and the DNA can be negative for rs17702901. In another embodiment, the DNA is negative for the rs17702901 and the pre-operative BMI of the subject can be greater than 25 kg/m².

In one aspect, a method of treating metabolic or weight-related disorders includes evaluating expression of one or more genes associated with response to a metabolic procedure. The gene can also be shown to be differentially expressed in patients before or after bariatric surgery. The expression level of the gene(s) can be compared to a reference range of expression of the gene and if expression of the gene(s) is outside the reference range, a first metabolic procedure can be performed, or if expression of the gene is inside the reference range, an alternative second metabolic procedure can be performed. For example, the expression level of the gene(s) can be compared to a reference range of expression of the gene and if expression of the gene(s) is outside the reference range, a first metabolic procedure can be performed, or if expression of the gene is inside the reference range, an alternative second metabolic procedure without a bariatric surgery can be performed. In some instances, the reference range of gene expression can be determined from multiple patients having undergone a metabolic procedure, such as bariatric surgery. The reference range of gene expression can be an average of gene expression from multiple patients. The reference range of gene expression can be about ±30%, ±25%, ±20%, ±15%, ±10%, or ±5% of an average of gene expression from multiple patients. The multiple patients may be a group of patients that have experienced therapeutically significant weight loss associated with a metabolic procedure, such as bariatric surgery; improvement, alleviation and/or amelioration of one or more co-morbid conditions. Alternatively, the group of patients may have experienced lack of therapeutically significant weight loss or an adverse metabolic event associated with a metabolic procedure, such as bariatric surgery, increased risk of obesity or obesity-related co-morbid conditions.

The gene can be at least one of SEQ ID NOs 1-128, also shown in Table 10. The gene can correlate with therapeutically significant weight loss associated with a metabolic procedure, such as bariatric surgery; improvement, alleviation or amelioration of one or more co-morbid conditions; and/or lack of therapeutically significant weight loss or an adverse metabolic event associated with bariatric surgery, increased risk of obesity or obesity-related co-morbid conditions in the subject. In one embodiment, gene expression can correlate with therapeutically significant weight loss after a metabolic procedure, such as bariatric surgery. Therapeutically significant weight loss can be characterized by loss of at least 20%, 25%, 30%, 35%, 40%, 45%, 50%, 60%, 65%, 70%, 75%, 80%, 85% or more of excess body weight. Therapeutically significant weight loss can also be characterized as at least 10%, 15%, 20%, 25%, 30%, 35%, 40%, 45%, 50%, 60%, 65%, 70%, 75%, or more weight change. Alternatively or in addition to, therapeutically significant weight loss can be characterized by change of at least 20%, 25%, 30%, 35%, 40%, 45%, 50%, 60%, 65%, 70%, 75%, 80%, 85% or more of body mass index.

Also, gene expression can correlate with improvement, alleviation or amelioration of one or more co-morbid conditions in the subject. Gene expression can correlate with, for example, reduced hypertension, reduced dyslipidemia, improvement or alleviation of diabetes, reduced acid reflux, alleviation of fatty liver or steatohepatitis, reduced risk of heart disease, alleviation of depression, alleviation of sleep apnea, alleviation of asthmatic symptoms, alleviation of arthritis, reduced risk of compression fractures, reduced occurrence of gallstones, lymphedema, alleviation of urinary incontinence, reduced risk of stroke, reduced risk of cancer and/or reduced risk of other metabolic syndromes.

Alternatively, gene expression can correlate with lack of therapeutically significant weight loss or an adverse metabolic event associated with bariatric surgery or increased risk of obesity, or obesity-related co-morbid conditions in the subject. Gene expression can correlate with, for example, lack of weight loss after bariatric surgery, increased hypertension, risk of dyslipidemia, development of diabetes, acid reflux, fatty liver disease or steatohepatitis, heart disease, depression, sleep apnea, asthmatic symptoms, arthritis, compression fractures, gallstones, lymphedema, urinary incontinence, stroke, cancer and/or risk of other metabolic syndromes.

Gene expression can be measured prior to any metabolic procedure or preoperative procedure. Gene expression can be also measured and compared to one or more measurements taken at different time points, such as after a metabolic procedure or post-surgery. Gene expression can be measured at 1, 3, 6, 9, 12, 18, 24, 36, 48, 72, 84, 96, 108, 120 months post metabolic procedure or postoperative or any number of months in between. In an exemplary embodiment, gene expression is measured prior to a metabolic procedure.

Modulating Gene Expression

Methods and compositions for modulating expression of at least one gene associated with response to a metabolic procedure in a target tissue to treat a subject having a metabolic disorder are also disclosed. Methods and pharmaceutical compositions to modulate gene expression can include delivering regulatory proteins, ligands, agonists and antagonists of expression of the gene to a target tissue. Gene therapy can be used to modulate gene expression and can also be accomplished by methods known to those skilled in the art. For example, one approach is to use an inducible promoter to drive expression of the gene delivered. In return, the in vivo steady state level of the gene can be increased, through augmented expression of the gene.

The terms "modulate" or "modulating" are used herein to refer to an increase or decrease or change in expression of at least one target protein or gene.

In one aspect, methods and composition are disclosed to modulate gene expression by providing a full-length, a portion or fragment of, or variant of the gene or its encoded protein and expressing the full-length, a portion or fragment of, or variant of the gene or its encoded protein in the target tissue. The term "full-length" refers to the entire open reading frame, capable of expressing a full-length encoded protein.

A "portion" or "fragment" of the gene or encoded protein refers to any sequence that has fewer nucleic acids or amino acids than the entire sequence of the gene or its encoded protein. Sizes of nucleic acid fragments can be 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or greater of the full-length gene. Sizes of peptide fragments can be about 500 amino acids, about 400 amino acids, about 300 amino acids, about 200 amino acids, about 100 amino acids, about 80 amino acids, about 60 amino acids, about 40 amino acids, about 20 amino acids, about 10 amino acids or any fragment in between of the full-length protein.

"Variant" as the term is used herein, can be a polynucleotide or polypeptide that differs from a reference nucleic acid or protein (i.e., SEQ ID NOs 1-128), but may retain essential properties (i.e., biological activity or conserved domains). A typical variant of a polynucleotide differs in nucleotide sequence from another, reference polynucleotide. Changes in the nucleotide sequence of the variant may or may not alter the amino acid sequence of a polypeptide encoded by the gene or sequence including or affected by the reference polynucleotide. Nucleotide changes may result in amino acid substitutions, additions, deletions, fusions and truncations in the polypeptide encoded by the reference sequence, as discussed below. Generally, differences are limited so that the sequences of the reference polypeptide and the variant are closely similar overall and, in many regions, identical. Variant polynucleotides can include polynucleotides having at least 70% identity, at least 80% identity, at least 90% identity, at least 95% identity, at least 96% identity, at least 97% identity, at least 98% identity or at least 99% identity to the reference nucleotide sequence of the gene.

Variant polypeptides can include any polypeptide having an amino acid residue sequence substantially identical to a sequence specifically shown herein in which one or more residues have been conservatively substituted with a functionally similar residue, and which displays the ability to mimic essential properties of the reference protein. Variant polypeptides can include polypeptides having at least 70% homology, at least 80% homology, at least 90% homology, at least 95% homology, at least 96% homology, at least 97% homology, at least 98% homology or at least 99% homology to the reference protein sequence.

In another embodiment, the compositions can include vectors to modulate expression of the gene. In an exemplary embodiment, the vector can include a full-length, a portion or fragment of, or variant of at least one of the nucleic acid sequences found in SEQ ID NOs 1-128. The vector can also be a viral vector, such as adenoviral vectors, adeno-associated viral vectors, retroviral vectors (including lentiviral vectors), alphaviral vectors (e.g., Sindbis vectors), and herpes virus vectors. The vector can also include an inducible promoter. The inducible promoter can be inducible through response to a regulator, such as cellular conditions, inducer molecules or stimuli. Regulatable promoters include inducible promoters, which are usually "off," but which may be induced to turn "on," and "repressible" promoters, which are usually "on," but may be turned off. Many different regulators are known to effect control over the activity of regulatable promoters, including temperature, hormones, growth factors, cytokines, heavy metals, and regulatory proteins. In one embodiment, the promoter can be inducible through exposure to an energy source. In another embodiment, the promoter can be inducible through exposure to light.

The compositions include a therapeutic agent that may be administered in a variety of forms. These include, for example, liquid, semi-solid and solid dosage forms, such as liquid solutions (e.g., injectable and infusible solutions), dispersions or suspensions, tablets, pills, powders, liposomes and suppositories. An exemplary form will depend on the intended mode of delivery and therapeutic application. Typical therapeutic agents are in the form of injectable or infusible solutions, such as therapeutic agents similar to those used for passive immunization of humans. Another mode of delivery is parenteral (e.g., intravenous, subcutaneous, intraperitoneal, intramuscular). In one embodiment, the therapeutic agent is delivered by intravenous infusion or injection. In another embodiment, the therapeutic agent is delivered by intramuscular or subcutaneous injection. In another embodiment, the therapeutic agent is delivered perorally. In yet another embodiment, the therapeutic agent is delivered to a specific location using stereotactic delivery. In an exemplary embodiment, the therapeutic agent is formulated for delivery to the target tissue selected from the group consisting of a brain, a spinal cord, a sympathetic nervous system, a parasympathetic nervous system, an enteric nervous system, a gastrointestinal tract and a pancreas.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the vector in the required amount in an appropriate solvent with one or a combination of ingredients enumerated above, as required, followed by filter sterilization.

The composition can be administered by a variety of methods known in the art. As will be appreciated by the skilled artisan, the route and/or mode of administration will vary depending upon the desired results. In certain embodiments, the therapeutic agent may be prepared with a carrier that will protect the agent against rapid release, such as a controlled release formulation, including implants, transdermal patches, and microencapsulated delivery systems. The carrier may also target delivery to at least one of a brain, a spinal cord, a sympathetic nervous system, a parasympathetic nervous system, an enteric nervous system, a gastrointestinal tract and a pancreas.

Carriers can be made of biodegradable, biocompatible polymers, such as ethylene vinyl acetate, polyanhydrides, polyglycolic acid, collagen, polyorthoesters, and polylactic acid. Many methods for the preparation of such formulations are generally known to those skilled in the art. See, e.g., *Sustained and Controlled Release Drug Delivery Systems*, J. R. Robinson, ed., Marcel Dekker, Inc., New York, 1978. The compositions may include a "therapeutically effective amount" to modulate expression of the gene(s). A "therapeutically effective amount" refers to an amount effective, at dosages and for periods of time necessary, to achieve the desired therapeutic result, such as gene expression modulation. The therapeutically effective amount may vary according to factors such as the disease state, age, sex, and weight of the individual, and the ability of the treatment to elicit a desired response in the individual. A therapeutically effective amount is also one in which any toxic or detrimental effects of the treatment are outweighed by the therapeutically beneficial effects.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Bariatric Surgery and Alternative Metabolic Procedures

After analyzing for the presence or absence of genetic indicators or measuring expression of the gene(s), a determination of whether to perform a first metabolic procedure or a second metabolic procedure, which is different than the first metabolic procedure, can be made. For example, after analyzing for the presence or absence of genetic indicators or measuring expression of the gene(s), a determination of whether to perform a first metabolic procedure, such as a bariatric surgery, or a second metabolic procedure excluding bariatric surgery can be made.

Bariatric surgery includes procedures often referred to as metabolic surgery or therapy, as well as a variety of procedures performed in a subject that leads to a physiologic improvement in energy balance, nutrient utilization, or metabolic disorders. Surgical procedures to treat severe obesity or obesity-related conditions have included various forms of bariatric surgery, such as but not limited to, gastric bypass, Roux-en-Y gastric bypass (RYGB), biliopancreatic diversion, partial gastrectomy procedures such as vertical sleeve gastrectomy, adjustable gastric banding, duodenal switch, duodenojejunal bypass, vertical banded gastroplasty, intragastric balloon therapy, greater curvature plication, gastric plication (including anterior and anteroposterior plication) and other forms of gastric volume reduction, Magenstrasse and Mill, ileal transposition or interposition, small bowel transposition, biliary diversion, procedures involving anastomotic connections of the gastrointestinal tract (e.g., jejunoileostomy, etc.), gastric balloon implantation and other gastric or intestinal device implantation, gastric, duodenal or intestinal endoluminal barrier implantation, gastric electrical stimulation, small bowel electrical stimulation, vagal electrical stimulation, vagal electrical inhibition, and variations of the procedures above as well as other methods known by those skilled in the art. Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. Non-surgical procedures can include, but are not limited to, pharmacological and nutritional therapies, such as hormone and neuropeptide therapy, receptor agonists and antagonists, etc.; procedures including a device, such as gastric balloon implantation and other gastric or intestinal device implantation, gastric, duodenal or intestinal endoluminal barrier implantation, etc.; and/or the activation of brown adipose tissue. In one embodiment, the first metabolic procedure is a bariatric surgery. In one embodiment, the first metabolic procedure is a non-surgical procedure. In another embodiment, the second metabolic procedure is a non-surgical procedure. In another embodiment, the second metabolic procedure is a procedure different from the first metabolic procedure.

Different metabolic procedures, like bariatric surgery, can also produce similar end results, such as weight loss or amelioration of co-morbid conditions, by acting through similar mechanisms. Studies done by Chambers et al. in *Gastroenterology* 2011; 141(3):950-958, which is incorporated herein by reference in its entirety, have shown similar effects of vertical sleeve gastrectomy and gastric bypass on weight loss, food intake, insulin sensitivity, glucose tolerance, insulin secretion, endogenous glucose production, and glucagon-like peptide-1 secretion. In addition, studies performed by Peterli et al. in *Ann Surg* 2009; 250(2):234-41, which is incorporated herein by reference in its entirety, have reproduced similar studies in humans showing that vertical sleeve gastrectomies and RYGB have similar effects on glucose production, and glucagon-like peptide-1 secretion. In particular, gastric bypass, biliopancreatic diversion, sleeve gastrectomy and endoluminal sleeve have shown similar effects on weight loss, food intake, insulin sensitivity, glucose tolerance, insulin secretion, and endogenous glucose production. Moreover, bariatric surgical procedures have also shown similar effects on the gastrointestinal endocrine system. Levels of ghrelin, glucagon-like peptide-1, peptide YY, amylin and gastric inhibitory polypeptide have shown similar changes in post-prandial secretion levels in individuals who have undergone gastric bypass, biliopancreatic diversion, sleeve gastrectomy, ileal interposition or duodenal endoluminal sleeve.

Some non-surgical examples of alternative metabolic procedures to bariatric surgery can include, but are not limited to, administering pharmacological and nutritional therapies, such as hormone and neuropeptide therapy, receptor agonists and antagonists, etc.; providing an alternative medical device based therapy, such as, but not limited to, gastric balloon implantation and other gastric or intestinal device implantation, gastric, duodenal or intestinal endoluminal barrier implantation, etc.; and/or the activation of brown adipose tissue. (See US Pat. Pub. No. 2011/0263490 entitled "Diagnostic Methods And Combination Therapies Involving MC4R" filed Dec. 29.2010, which is hereby incorporated by reference in its entirety.) The treatments can be temporary. By temporarily performing the treatments, assessment of the efficacy of the treatment can be made. Moreover, as the treatment can be temporary, and possibly reversible, evaluating the efficacy of the treatment can influence whether additional treatments need to be performed or if the treatment alone is sufficient to attain the desired weight loss and other clinical results.

Hormone and neuropeptide therapy can also be used to regulate or suppress appetite, increase body energy expenditure, and/or decrease fat mass accumulation (McMinn, J. E., Baskin, D. G. & Schwartz, M. W., Obes. Rev. 2000; 1:37-46; Drazen, D. L. & Woods, S. C., Curr. Opin. Clin. Nutr. Metab. Care 2003; 6:621-629).

Activation of brown adipose tissue (BAT) can further lead to mobilization of fat stores within brown adipocytes to increase fat metabolism. The controlled activation of BAT can be optimized, leading to weight loss by reducing the stores of triglycerides in white adipose tissue (WAT).

BAT activation can occur either directly or transcutaneously. Either can stimulate the sympathetic nervous system to physiologically activate BAT. Whether BAT is activated directly and/or transcutaneously, target areas for BAT stimulation can include areas in the vicinity of BAT depots, e.g., the nape of the neck, over the scapula, alongside the spinal cord, and around the kidneys. Any BAT depot can be selected for activation. In the course of treating a patient, BAT nerves can be stimulated at any one or more BAT depots and can be stimulated simultaneously, e.g., two or more BAT depots being concurrently stimulated, or stimulated sequentially, e.g., different BAT depots being stimulated at different times. Simultaneous stimulation of BAT can help encourage more and/or faster energy expenditure. Sequential stimulation of BAT can help prevent the "burning out" of target nerves and can help stimulate the creation of new BAT cells. Sequential nerve stimulation can include stimulating the same BAT depot more than once, with at least one other BAT depot being activated before activating a previously activated BAT depot.

Generally, direct activation of BAT can include implanting a device below the skin surface proximate to a BAT depot, e.g., within a BAT depot, and activating the device to deliver an electrical signal to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art.

The electrical signal, whether transcutaneously or directly delivered to BAT, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. A transcutaneous device can be used to transcutaneously activate BAT through a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. In an exemplary embodiment, the transcutaneous device can include an electrical stimulation patch configured to be applied to an external skin surface and to deliver an electrical signal to tissue below the skin surface, e.g., to underlying BAT.

Stimulation of BAT using an electrical signal is described in further detail in US Pat. Pub. No. 2011/0270360 entitled "Methods And Devices For Activating Brown Adipose Tissue Using Electrical Energy" filed Dec. 29, 2010, and stimulation of BAT using other exemplary modes of stimulation are described in further detail in PCT Pat. App. No. PCT/US11/66399 entitled "Methods And Devices For Activating Brown Adipose Tissue With Targeted Substance Delivery" filed Dec. 21, 2011, PCT Pat. App. No. PCT/US11/66358 entitled "Brown Adipocyte Modification" filed Dec. 21, 2011, PCT Pat. App. No. PCT/US11/66409 entitled "Methods And Devices For Activating Brown Adipose Tissue With Light" filed Dec. 21, 2011, and PCT Pat. App. No. PCT/US11/66415 entitled "Methods And Devices For Activating Brown Adipose Tissue With Cooling" filed Dec. 21, 2011.

The electrical signal, whether transcutaneously or directly delivered, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. A transcutaneous device can be used to transcutaneously activate BAT through a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. In an exemplary embodiment, the transcutaneous device can include an electrical stimulation patch configured to be applied to an external skin surface and to deliver an electrical signal to tissue below the skin surface, e.g., to underlying BAT.

Procedure Outcome Indicators

Indicators that predict outcomes after a metabolic procedure can also be measured and used in the methods disclosed herein. Such indicators can include genetic indicators and/or clinical measurements obtained from the patient. Examples of genetic indicators are described in more detail in U.S. Prov. Pat. App. No. 61/704,434 entitled "Clinical Predictors of Weight Loss" filed on Sep. 21, 2012, which is incorporated herein by reference in its entirety. Examples of clinical measurements can include, but are not limited to, pre-operative BMI, a glucose tolerance, bile acid profile, and body composition/fat distribution of the subject. Pre-operative BMI can be greater than 23 kg/m$^2$ in non-Asians or greater than 21 kg/m$^2$ in Asians. Individuals at a lower than "overweight" BMI may also be at risk of at least one weight-related comorbidity and therefore be applicable subjects to be treated or assessed by methods of this invention (e.g., Caucasians having a BMI of greater than 23 and Asians, a BMI of greater than 21). In some embodiments, pre-operative BMI can be greater than 25 kg/m$^2$ in non-Asians or greater than 23 kg/m$^2$ in Asians.

Additional non-limiting examples of indicators include, but are not limited to height, weight, gender, age, medical history and/or status, ethnicity, medical prescription history and/or status, types of previously received medical treatments for obesity (e.g., medications, BAT stimulation, gastric banding, gastric bypass, sleeve gastrectomy, etc), types of medical treatments previously received for health issues other than obesity (e.g., medications, surgical treatments, and non-surgical treatments), insurance information, diet information for the patient, and psychological history of the patient.

Predicting Bariatric Surgery Outcomes

Various systems and methods are provided for predicting metabolic therapy, e.g., metabolic and bariatric surgery, outcomes, i.e., a composite predictive model. The systems and methods can also provide predictions for non-surgical metabolic and bariatric treatments. In general, a user, e.g., a patient, a medical professional involved with treating a patient, a medical student, a hospital administrator, a health insurance administrator, etc., can receive predictive outcomes of multiple metabolic therapies that could be performed on a patient. The collection of therapies for the treatment of obesity and metabolic disease (e.g., diet and exercise, pharmaceutical therapy, medically supervised therapy), metabolic surgery (open, laparoscopic, natural orifice, etc.), bariatric surgery (open, laparoscopic, natural orifice, etc.) are collectively defined herein as metabolic therapies. In one embodiment, a user can electronically access a metabolic therapy outcome prediction system, e.g., using one or more web pages. The system can provide predictive outcomes of one or more different metabolic therapies, such as bariatric surgeries, for the patient based on data gathered from the user and on historical data regarding outcomes of the different bariatric surgeries. The system can additionally provide predictive outcomes for not having any treatment and/or a comparison of the predictive outcomes of the one or more different bariatric surgeries to the predictive outcomes for not having any treatment or for having non-surgical treatment. Generally, the predictive outcomes provided by the system can include a potential clinical metabolic outcome of each of the different bariatric surgeries, e.g., a predicted amount of weight loss, a predicted amount of body mass index (BMI) reduction, an improvement in a health condition associated with a metabolic disease, an associated risk of complications from the treatment, and/or an associated cost of the surgery and post-operative care. The predictive outcomes can be based on a plurality of patient-specific characteristics, e.g., age, weight, height, BMI, ethnicity, medical prescription history and/or status, genetic data (e.g., a genetic indicator), gene expression profiles (expression of one or more genes, expression over a time period and/or in different tissues), types of previously received medical treatments for obesity (e.g., gastric banding, gastric bypass, sleeve gastrectomy, etc), medical history and/or status, gender, etc. The predictive outcomes can also be based on historic results of the different types of bariatric surgeries on other patients. The predictive outcomes can thus be based at least in part on data specific to the patient and not just on historical data, e.g., data gathered by the user from previous personal experience, friends or colleagues, journal articles, internet research, clinical data, etc. The outputs can thus be personalized to the patient. The system can help the user be more informed about which of the bariatric surgeries would be most effective if performed on the patient, help specifically compare and contrast the different bariatric surgeries, and help the user decide which of the different bariatric surgeries, if any, to pursue for the patient. The system can therefore help maximize effectiveness of treatment for the patient by allowing a most effective option to be identified and pursued by the patient and/or by medical practitioner(s) treating the patient. The system can also help inform the user about bariatric surgery options that they might not have been aware of at all, e.g., new procedures, and/or deepen understanding of bariatric surgery procedures previously known to the user. The system can be configured to allow the user to save the predictive outcomes, which can then be accessed at a later date/time by the user and/or one or more other users, e.g., the user's surgeon, the user's endocrinologist, the user's primary care physician, or other healthcare providers, etc., to which the user grants access to the saved data.

Methods and systems for providing predictive outcomes are described in more detail in U.S. Prov. Pat. App. No. 61/704,077 entitled "Systems and Methods for Predicting Bariatric Surgery Outcomes" filed on Sep. 21, 2012, which is incorporated herein by reference in its entirety.

Output results can be reported in multiple ways, either individually or simultaneously via the system. In one embodiment, output results can be reported in parameters such as, but are not limited to, target weight loss in pounds or kilograms, target weight, percent excess body weight loss, percent weight change, percent change in BMI. In another embodiment, output results can be reported as continuous or at various cutoff points ranging from 1-100%. An example of various cutoff may include achieving at least or at most 50% excess weight loss. Another example of various cutoff may include achieving at least or at most 70% excess weight loss. In yet another embodiment, the output results can be reported as results obtained at various timepoints post metabolic procedure such as bariatric surgery or alternative metabolic procedure without bariatric surgery. Timepoints can include 1, 3, 6, 9, 12, 18, 24, 36, 48, 72, 84, 96, 108, 120 months post treatment or any number of months in between. In another embodiment, the output results can be reported as nadir weight. "Nadir weight" as used herein is defined as the lowest weight achieved at least 10 months after surgery without coexisting debilitating illness, with or without use of weight lowering medications.

The input parameters can be analyzed via the interface in a model algorithm. The algorithm can apply univariate analyses, multivariable regression analyses, advanced regression analyses, and other data mining techniques on multiple data sets to build, train and prospectively model predicted results after metabolic procedure such as bariatric surgery or alternative metabolic procedure without bariatric surgery.

The interface can also be used to output varying levels of confidence of the prediction on the results after metabolic procedure such as bariatric surgery or alternative metabolic procedure without bariatric surgery. Such examples can include the predicted result based on variable changes in weight, e.g., 20% chance of 40 lb change in weight, 40% chance of 20 lb change in weight, etc. The output can further include predictions based on complications associated with a metabolic procedure such as bariatric surgery or an alternative metabolic procedure without bariatric surgery.

The output results can be collected and used by patients, primary care providers, and/or other referring physicians or other healthcare providers. The information can be provided in the patient's home, during a health care provider seminar, during a physician's office visit, and/or prior to treatment. Moreover, the interface can be accessed through various routes. In one embodiment, the interface can be accessed via the internet to record and model the patient information. In another embodiment, the interface can be accessed via a mobile device or "app," software application designed specifically for mobile or handheld devices. In yet another embodiment, the interface can be accessed via application software that can be installed on a computer or other device.

In addition to providing predictive outcomes, the system can optionally provide educational information regarding each of the different bariatric surgeries and/or other types of information related to bariatric surgery such as estimated patient monetary cost (based on one or more factors such as the patient's insurance carrier, similar procedures performed in the patient's geographic location, etc.), estimated insurance reimbursement (based on one or more factors such as the patient's insurance carrier, similar procedures performed in the patient's geographic location, etc.), estimated length of post-surgery hospital stay (based on one or more factors such as similar procedures performed in the patient's geographic location, the patient's age, the patient's other health conditions or disorders, etc.). The system can therefore help the user be more fully informed about the various risks and benefits of the various bariatric surgeries before deciding which of the bariatric surgeries to pursue, if any. Applying similar modeling techniques, personalized predictions can be provided for use of one or more of the preceding educational and/or other information.

One skilled in the art will appreciate further features and advantages of the invention based on the above-described embodiments. Accordingly, the invention is not to be limited by what has been particularly shown and described in the examples or figures, except as indicated by the appended claims. All publications and references cited herein are expressly incorporated herein by reference in their entirety.

EXAMPLES

Example 1: Genetic Analysis Materials and Methods

Study Population: To identify genetic factors contributing to weight loss after RYGB, an exploratory genome-wide association study of individuals of European descent undergoing RYGB was performed. The study was approved by and performed in accordance with the guidelines of the Human Studies Committee at the Massachusetts General Hospital. From February 2000 until April 2007, consent was obtained from 1018 (97%) of MGH Weight Center patients undergoing RYGB to collect and extract DNA from tissue samples removed at the time of surgery. Intraoperative liver, subcutaneous fat, omental fat, and stomach tissues were collected in RNAlater (Amnion/Applied Biosystems) and stored at −80° C. Operations were either open (41%) or laparoscopic (59%) RYGB. For the open procedure, the stomach was partitioned but not divided, and for the laparoscopic procedure the pouch was partitioned and divided from the remaining stomach. Otherwise, the techniques were the same, with an approximately 30 ml pouch, a 100-120 cm Roux (alimentary) limb fashioned in a retrocolic, retrogastric configuration, and a pancreaticobiliary limb extending approximately 75 cm beyond the ligament of Treitz.

Demographic and clinical information was extracted from review of the electronic medical records. Weight nadir was defined as the lowest weight achieved at least 10 months after surgery. Chart-derived nadir weight was validated through telephone interviews in a subset of patients (n=306); there was a 97% correlation between these two sources. Percent weight loss (% WL) at weight nadir was calculated by subtracting the patient's weight at nadir from his or her presurgical weight, and then dividing by the patient's presurgical weight.

The following materials and methods apply to Examples 2 through 8:

Surgical procedures: For the open procedure, the stomach was partitioned but not divided, and for laparoscopic procedure the pouch was partitioned and divided from the remaining stomach. Otherwise, the techniques were the same, with an ~30 ml pouch and a 100-120 cm Roux limb fashioned in a retrocolic, retrogastric configuration, and the pancreaticobiliary limb extending ~75 cm from the ligament of Treitz.

DNA analysis: Genomic DNA was extracted from collected liver samples, and genotyping was performed using the Illumina HumanHap 650Y BeadChip array (Illumina Inc., San Diego, Calif.). Race was genetically determined by principal component analysis using EIGENSTRAT; there was 97% concordance with self-reported race. Patients were excluded if they were on weight-lowering medications after surgery (1.7%), had cancer or other severe illness (including severe postoperative complications or reoperations; 2.4%), their DNA was not available (4.7%), or their postoperative body mass index (BMI) at least 10 months after RYGB could not be determined (7.9%). Using identity-by-descent methods (PLINK software), we identified 13 first-degree relative pairs, defined as pairs of individuals who share approximately 50% of their genetic variation, six second-degree relative pairs (~25% of genetic variation shared) and four third-degree relative pairs (~12.5% of genetic variation shared). An additional eight patients who were genetically related to established first-degree pairs were excluded, leading to a final sample of 848 (83.3%). Then the samples were matched on genetically identified race, randomly paired 794 unrelated individuals from the cohort, and compared for the similarity in their weight loss outcomes after surgery. Also identified were 20 cohabitating individuals by review of the medical records of all patients who had undergone RYGB at this center. No cohabitating individuals were genetically related.

Endpoint and covariate assessment: Demographic and clinical information was extracted from the medical record. A patient's weight nadir was identified, defined as the lowest weight achieved at least 10 months after surgery without coexisting debilitating illness or use of weight lowering medications. The percent excess body weight lost (EBWL) at weight nadir was calculated by subtracting the patient's nadir BMI from his or her preoperative BMI and dividing this difference by the difference between the patient's initial BMI and the upper normal BMI of 25 kg/m$^2$. Chart-derived weights were validated via telephone interviews in a subset of patients (n=306); there was a 97% concordance between these two sources.

Statistical analyses: The average difference in outcome was calculated by pair, and analyses based on these mean differences were based on one entry per pair. Wilcoxon rank sum tests were used to test differences in mean response between groups. Linear mixed effects models were constructed to determine the intraclass correlation coefficients (ICC) by type of relationship. All nongenetic analyses were performed using SAS statistical software (SAS Institute, Cary, N.C.).

The following materials and methods apply to Example 9:

Genotyping and Data Cleaning of Study Population: Samples were shipped to the Rosetta Inpharmatics Gene Expression Laboratory (Seattle, Wash.) where genomic DNA was extracted from liver samples. Nine hundred fifty samples were successfully genotyped using the Illumina HumanHap 650Y BeadChip array (Illumina Corp, San Diego, Calif.). Data were converted to PLINK format (Hatoum, I. J., Stein, H. K., Merrifield, B. F. & Kaplan, L. M., Capacity For Physical Activity Predicts Weight Loss After Roux-En-Y Gastric Bypass, *Obesity* (Silver Spring) 17, 92-99 (2009)), and all genetic analyses were performed using this software. Using identity-by-descent (IBD) coefficients for all pairs of individuals, 36 related individuals were identified, defined as an IBD coefficient >0.125. One person per family was included for analysis, based on completeness of phenotypic and genetic information. In addition, one person was removed from the analysis because >10% of the person's genetic information was missing. Of the remaining 933 individuals, 806 self-identified as European. To address population structure not captured through self-identification, EIGENSTRAT (Hatoum, I. J. et al. Heritability Of The Weight Loss Response To Gastric Bypass Surgery, *J Clin Endocrinol Metab* 96, E1630-3 (2011)) was used to calculate principal components of ancestry, and identified 25 outlying samples (greater than six standard deviations) for a sample of 781 patients. Of these 781 samples, 693 had a weight nadir value, were not on weight-lowering medications after surgery, did not have cancer or other severe illness, and were thus included in the final data set. Imputation of 1,674,205 additional SNPs was performed using MACH software. (Ochner, C. N. et al. Selective Reduction In Neural Responses To High Calorie Foods Following Gastric Bypass Surgery, *Ann. Surg.* 253, 502-507 (2011).) A SNP was excluded from analyses if it was missing in >10% of the samples, if it had less than 1% minor allele frequency, or if it was not in Hardy-Weinberg equilibrium, resulting in a SNP set of 1,943,373 SNPs. A genomic control inflation factor of 1.01 was observed, indicating minimal inflation of test statistics due to population stratification (FIG. 1).

Gene Expression Profiling: Total RNA was extracted from liver, subcutaneous fat, and omental fat tissues. Liver, subcutaneous fat and omental fat RNA was amplified and converted to fluorescently labeled cRNA that was hybridized to custom 44K DNA oligonucleotide microarrays from Agilent Technologies (Santa Clara, Calif., USA). A detailed description of the normalization and data cleaning methods has been described previously. (Shin, A. C., Zheng, H., Pistell, P. J. & Berthoud, H.-R., Roux-En-Y Gastric Bypass Surgery Changes Food Reward In Rats, *Int J Obes* (Lond) 35, 642-651 (2011).) 707, 870, and 916 samples were profiled from liver, subcutaneous fat, and omental fat, respectively.

Replication Cohort: From May 2007 until October 2009, we obtained consent from 369 Caucasian MGH Weight Center patients undergoing RYGB to collect and extract DNA from tissue samples removed at the time of surgery. Intraoperative liver tissue samples were collected in RNAlater (Amnion/Applied Biosystems) and stored at −80°. Operations were as described for the GWAS cohort. Clinical traits were extracted from the electronic medical records, as described for the GWAS cohort.

Genotyping and Data Cleaning of Replication Cohort: Samples were shipped to the Eli and Edythe Broad Institute (Cambridge, Mass.) where genomic DNA was extracted from liver samples. Three hundred sixty-nine samples were successfully genotyped using Sequenom MassARRAY (Sequenom Inc., San Diego, Calif.). Of these, 327 had a recorded weight nadir value, were not on weight-lowering medications after surgery, did not have cancer or other severe illness, and were thus included in the final data set.

Endpoint and Covariate Assessment: Demographic and clinical information was extracted from review of electronic medical records. Weight nadir was defined as the lowest weight achieved at least 10 months after surgery. Chart-derived nadir weight was validated through telephone interviews in a subset of patients (n=306); there was a 97% correlation between these two sources. Percent weight loss (% WL) at weight nadir was calculated by subtracting the patient's weight at nadir from his or her presurgical weight, and then dividing by the patient's presurgical weight. Percent excess body weight loss (% EBWL) was calculated by subtracting the patient's current weight from the patient's presurgical weight, and dividing this difference by the difference between the patient's presurgical weight and the patient's ideal or target weight.

Animal Studies: All experiments in mice were performed in compliance with and were approved by the Institutional Animal Care and Use Committee of the Massachusetts General Hospital. We have developed a mouse model of RYGB that closely mimics the procedure in humans. At 12 weeks of age, male, diet-induced obese C57BL/6 mice on a high fat diet from weaning (Jackson Laboratories, Bar Harbor, Me.) were randomized to RYGB, sham operation with post-operative ad libitum food intake, or sham operation with food restriction to match the weights of the RYGB mice weekly. In the RYGB procedure, the stomach was divided into a gastric pouch and distal stomach using a vascular clip (Ethicon Endo-Surgery, Inc., Cincinnati, Ohio). For each of the Roux (alimentary) and biliopancreatic limbs, the length of the intestine was 6 cm, approximating the 12-15% instestinal bypass used in the human operation. The alimentary limb was then secured to the gastric fundus by a gastrojejunal anastamosis. Sham operations consisted of a laparotomy and repair. Mice were maintained on a high-fat diet (D12492 diet; Research Diets, New Brunswick, N.J.) except during the 7-14 days after surgery, when all mice were maintained on a postoperative protocol that progressed from water only to liquid diet to solid diet. Animals were individually housed in a 12-hour light, 12-hour dark cycle under controlled temperature and humidity conditions.

Animals were euthanized by carbon dioxide inhalation followed by cervical dislocation at 10 weeks after surgery. All tissues were harvested immediately, flash frozen and stored at −80° C. until further processing. For gene expression studies, total RNA was extracted using SuperScript® III First-Strand Synthesis System for RT-PCR kit (Invitrogen, Carlsbad Calif.), according to the manufacturer's instructions. One µg of total RNA was used as template for cDNA synthesis using TaqMan® Gene Expression Master Mix kit (Applied Biosciences, Carlsbad Calif.), according to the manufacturer's instructions. Relative expression level was determined by qPCR using pre-optimized, gene-specific primer probe sets purchased from Applied Biosciences for AQP11 (Mm00613023_m1; Cat #4331182), SLCO3A1 (Mm00452449_m1; Cat #4331182), CLNS1A (Mm00445821_m1; Cat #4331182) and ST8SIA2 (Mm01311039_m1; Cat #4331182) and a CFX96™ Real-Time PCR Detection System (BioRad, Hercules, Calif.). All expression level data was presented relative to actin.

Tissue Samples: Intraoperative liver, subcutaneous fat, omental fat, and stomach tissues were collected in RNAlater (Amnion/Applied Biosystems) and stored at −80° C. Operations were either open (41%) or laparoscopic (59%) RYGB. For the open procedure, the stomach was partitioned but not divided, and for the laparoscopic procedure the pouch was partitioned and divided from the remaining stomach. Otherwise, the techniques were the same, with an approximately 30 ml pouch, a 100-120 cm Roux limb fashioned in a retrocolic, retrogastric configuration, and a pancreaticobiliary limb extending approximately 75 cm beyond the ligament of Treitz.

Gene Expression Profiling: Total RNA was extracted from liver, subcutaneous fat, and omental fat tissues. Liver, subcutaneous fat and omental fat RNA was amplified and converted to fluorescently labeled cRNA that was hybridized to custom 44K DNA oligonucleotide microarrays from Agilent Technologies (Santa Clara, Calif.). A detailed description of the normalization and data cleaning methods has been described previously. Successful profiling of 707, 870, and 916 samples from liver, subcutaneous fat, and omental fat, respectively, was performed.

Example 2: Genetic Analysis

Preoperatively, patients in this cohort had an average BMI of 50.2±8.6 kg/m2, an average age of 44.7±11.3 yr, and were 74.8% female and 86% Caucasian. These characteristics were similar among the different groups studied (see Table 1).

TABLE 1

Patient demographics at baseline by type of relationship.

| | Degree Of Relatedness | | |
| --- | --- | --- | --- |
| Characteristic | Not Related | First Degree | Cohabitating |
| N | 794 | 26 | 20 |
| AGE (YEARS) | 44.9 | 41.1 | 44.4 |
| SEX (% FEMALE) | 74.6 | 76.0 | 65.0 |
| RACE (%) | | | |
| EUROPEAN | 87.8 | 84.6 | 90.0 |
| HISPANIC | 7.8 | 7.7 | 10.0 |
| BLACK | 4.4 | 7.7 | 0 |

After RYGB, patients lost an average of 119.2±41.7 pounds at weight nadir, corresponding to an EBWL of 79.7±21.8%; the population pattern of percent excess weight loss follows the wide and normal distribution observed previously (FIG. 1).

Figure 2:
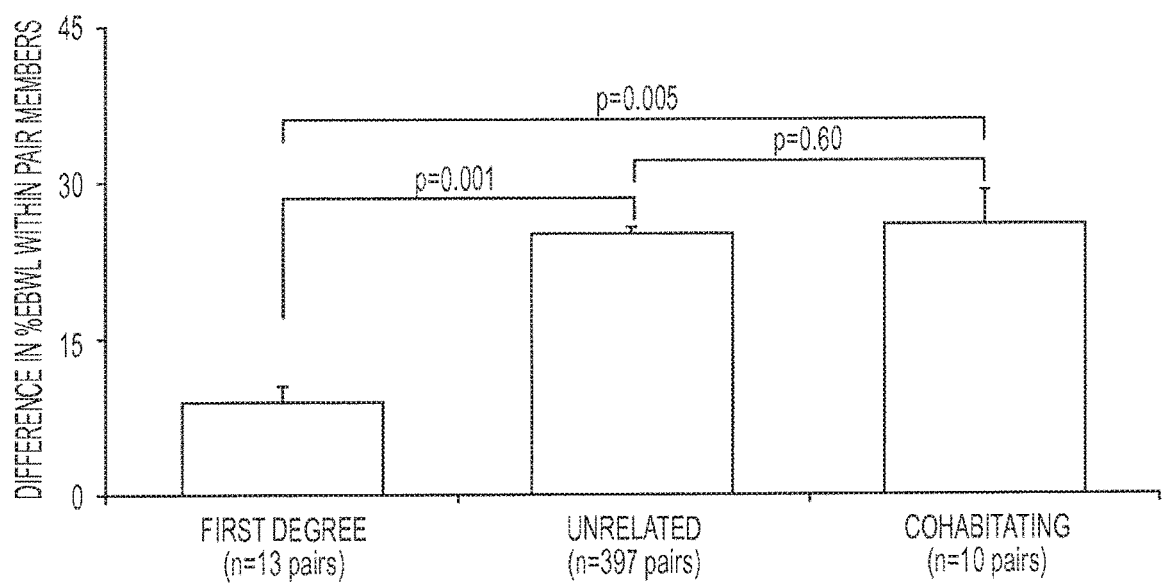
FIG. 2 is a bar graph showing the mean difference in percent EBWL within patient pairs, according to type of relationship.

To determine whether there is a genetic component to the variation in weight loss after surgery, weight loss after RYGB within pairs of genetically related was compared to genetically unrelated individuals. Unrelated individuals demonstrated far less similar weight loss after surgery than first-degree relatives (FIG. 2), with an average difference in EBWL of 25.4% in unrelated individuals and 9.9% in first-degree relatives (P=0.001). Because the observed similarity in weight loss could result primarily from shared environmental influences, weight loss within pairs of individuals who were living together but who are genetically unrelated was compared. Pairs of these environmentally related controls had a shared response similar to completely unrelated individuals (mean 26.1% difference in EBWL; P=0.60), a response that was substantially different from that of first-degree relatives (P=0.005). The small number of second- and third-degree relative pairs in this cohort precludes statistical analysis of these groups.

The ICC represents the portion of total variation in outcome explained by the pair relationship. Using mixed-effects models adjusted for age, sex, year of surgery, and preoperative BMI, the ICC were 70.4% for first-degree relatives (P=0.02), 14.3% for environmentally related controls (P=0.67), and 0.9% for randomly paired individuals (P=0.48). Because preoperative BMI is strongly associated with postoperative percent EBWL, we additionally matched the unrelated controls based on 5-kg/m2-wide BMI groups to mimic the distribution of differences in preoperative BMI between first-degree relatives. After this adjustment, first degree relative pairs still demonstrated significantly less difference in weight loss compared with the unrelated controls (difference in EBWL for unrelated pairs 22.3±17.9%; P=0.01 vs. first-degree relatives). Thus, first-degree relatives have weight loss outcomes after surgery that closely and significantly resemble each other, a characteristic not shared by environmentally related (cohabitating) controls or randomly paired individuals. Similar results were seen when men and women were examined separately (data not shown).

Example 3: Reporting Methods Materials and Methods

Study Population: Participants were recruited from the population of patients undergoing RYGB at a single academic center that is part of a larger 13-hospital network in the Boston metropolitan area. From February 2000 until April 2007, we obtained consent from 1018 (97%) of the patients undergoing RYGB at this center. Operations included both open and laparoscopic RYGB performed by one of two surgeons using the same operative techniques; the surgical methods have been described previously. This study was approved by the institutional review board of the Massachusetts General Hospital.

Endpoint and Covariate Assessment: Demographic and clinical information was extracted from the medical record. We identified a patient's weight nadir, defined as the lowest weight achieved at least 10 months after surgery without coexisting debilitating illness or use of weight-lowering medications. One-year weight was defined as the weight closest to 12 months from surgery, within the range of 10-14 months after surgery. Post-operative weights were available for 848 patients (83.3%). Chart-derived nadir weights were validated by telephone interviews in a subset of patients (n=306); there was a 94% concordance between these two sources. Diabetes diagnosis was extracted from patient charts and defined as the documentation of diabetes, a fasting glucose measurement ≥126 mg/dL, or the use of diabetes medication (insulin or metformin).

Weight loss was characterized at one year and at weight nadir using seven different metrics (Table 2). Residuals were calculated by regressing postoperative BMI (the dependent variable) on preoperative BMI (the independent variable) and outputting the residuals from this model. Because residuals derived from regressing postoperative BMI on preoperative BMI represent, by definition, postoperative BMI independent of preoperative BMI, these residuals were used as the benchmark of independence from preoperative BMI. Weight loss characterized by number of pounds lost was calculated by subtracting the patient's final weight from his or her baseline weight. As BMI is a function of weight and height, and height is almost always stable over the course of a weight loss study, BMI and pounds lost are closely similar methods for measuring weight loss. Percent weight change was calculated by dividing the absolute pounds lost by the patient's initial weight, and is statistically interchangeable with percent BMI change. Percent EBWL was calculated by dividing the difference between initial BMI and final BMI by the difference between initial BMI and a "normal" BMI. A BMI of 25 kg/m$^2$ is commonly used to represent the target, or upper limit of a "normal" BMI, but other standards, including race-specific BMI standards or other "ideal weights" according to the Metropolitan Life Insurance Company (MLIC) life tables, may also be used to represent "normal." In this study, % EBWL was calculated as described above, using a reference BMI of 25 kg/m$^2$.

Statistical Analyses: Patients were divided into seven preoperative BMI (pBMI) groups (35-39.9, 40-44.9, 45-49.9, 50-54.9, 55-59.9, 60-64.9, 65+). Means for each weight loss metric were calculated for each pBMI group, and linear trends across the groups were assessed using a test for trend of the median value within each group. Correlations between pBMI and each continuous metric were assessed using Spearman correlations, and r$^2$ measures were derived from linear regressions. All analyses were performed using SAS statistical software (SAS Institute, Cary, N.C.).

Example 4: Reporting Methods of Weight Loss

At baseline, participants had an average BMI of 50.0 (SD±8.3) kg/m$^2$, an average age of 44.7 (±11.5) years, 74.3% were female and 26.2% had diabetes. One year after RYGB, patients lost an average of 17.1 kg/m$^2$, 34.2% of baseline weight, and 71.7% of excess body weight (Table 2). By weight nadir, which on average occurred 28.5 months after surgery, patients lost an average of 19.4 kg/m$^2$, 38.7% of baseline weight, and 81.2% of excess body weight (Table 3).

TABLE 2

Different Parameterizations of Weight Loss.

| Metric | Abbreviation | Formula |
|---|---|---|
| Residuals |  | e = Observed Final BMI − Predicted Final BMI<br>Predicted BMI from the equation:<br>Final BMI = Initial BMI |
| Weight lost (in pounds or kg) | Δ pounds, Δ kg | Initial Weight(lbs or kgs) − Final Weight(lbs or kgs) |
| Weight achieved (in pounds or kg) |  | Final Weight (lbs or kgs) |
| BMI units lost | Δ BMI | Initial BMI − Final BMI |
| BMI achieved |  | Final BMI |
| Percent excess body weight lost | % EBWL | $\frac{\text{Initial BMI} - \text{Final BMI}}{\text{Initial BMI} - \text{Ideal BMI}} * 100$ |
| Percent weight change | % WC | $\frac{\text{Initial Weight} - \text{Final Weight}}{\text{Initial Weight}} * 100$ |

TABLE 3

Weight loss parameterizations by preoperative BMI group.

| | Baseline BMI (kg/m$^2$) Group | | | | | | | |
|---|---|---|---|---|---|---|---|---|
| | Overall | 35-39.9 | 40-44.9 | 45-49.9 | 50-54.9 | 55-59.9 | 60-64.9 | ≥65 | p for trend |
| N | 846 | 61 | 206 | 228 | 157 | 94 | 58 | 42 | N/A |
| Preoperative BMI (kg/m$^2$) | 50.0 | 38.3 | 42.9 | 47.5 | 52.3 | 57.2 | 62.4 | 72.8 | N/A |
| Residuals at 1 year | 0 | 0.9 | −0.2 | 0 | −0.3 | −0.2 | 0.4 | 0.8 | 0.66 |
| Residuals at weight nadir | 0 | 0.8 | −0.4 | 0.2 | 0.1 | −0.6 | 0.7 | 0.1 | 0.85 |
| Pounds lost at 1 year | 106.2 | 74.8 | 90.4 | 99.6 | 114.0 | 123.7 | 129.6 | 161.3 | 3.4e−53 |
| Pounds lost at weight nadir | 120.3 | 80.4 | 101.0 | 110.9 | 128.0 | 147.1 | 151.0 | 193.1 | 6.5e−84 |
| Weight (pounds) at 1 year | 204.4 | 165.2 | 172.9 | 193.1 | 215.0 | 231.4 | 249.9 | 310.4 | 2.9e−90 |
| Weight (pounds) at weight nadir | 188.5 | 155.6 | 162.4 | 180.2 | 200.0 | 208.8 | 227.9 | 266.9 | 3.6e−80 |
| BMI units lost at 1 year | 17.1 | 12.0 | 14.7 | 16.2 | 18.2 | 19.9 | 21.2 | 24.8 | 5.8e−59 |
| BMI units lost at weight nadir | 19.4 | 13.0 | 16.5 | 18.1 | 20.5 | 23.6 | 24.7 | 30.3 | 7.1e−94 |
| BMI achieved at 1 year | 32.9 | 26.4 | 28.1 | 31.2 | 34.1 | 37.3 | 41.3 | 48.6 | 2.8e−140 |
| BMI achieved at weight nadir | 30.5 | 25.3 | 26.3 | 29.4 | 31.8 | 33.6 | 37.7 | 42.4 | 4.9e−110 |
| % EBWL at 1 year | 71.7 | 89.3 | 82.7 | 72.2 | 66.8 | 61.9 | 56.6 | 51.1 | 1.0e−40 |
| % EBWL at weight nadir | 81.2 | 98.2 | 92.6 | 80.7 | 75.1 | 73.5 | 66.2 | 63.3 | 6.9e−38 |
| % WC at 1 year | 34.2 | 31.2 | 34.4 | 34.1 | 34.8 | 34.9 | 33.9 | 33.6 | 0.42 |
| % WC at weight nadir | 38.7 | 33.4 | 38.4 | 38.2 | 39.2 | 41.3 | 39.6 | 41.5 | 0.0002 |

Figure 4:
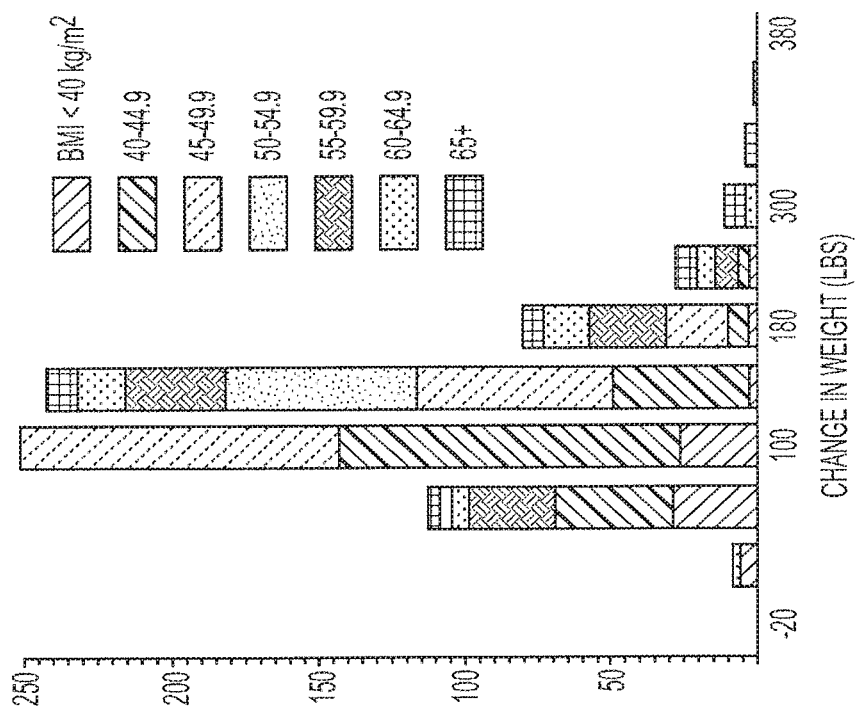
FIG. 4 is a bar graph showing absolute change in weight of the 848 patients after 1 year postoperative with patients in lower BMI groups losing significantly less weight.
Figure 3:
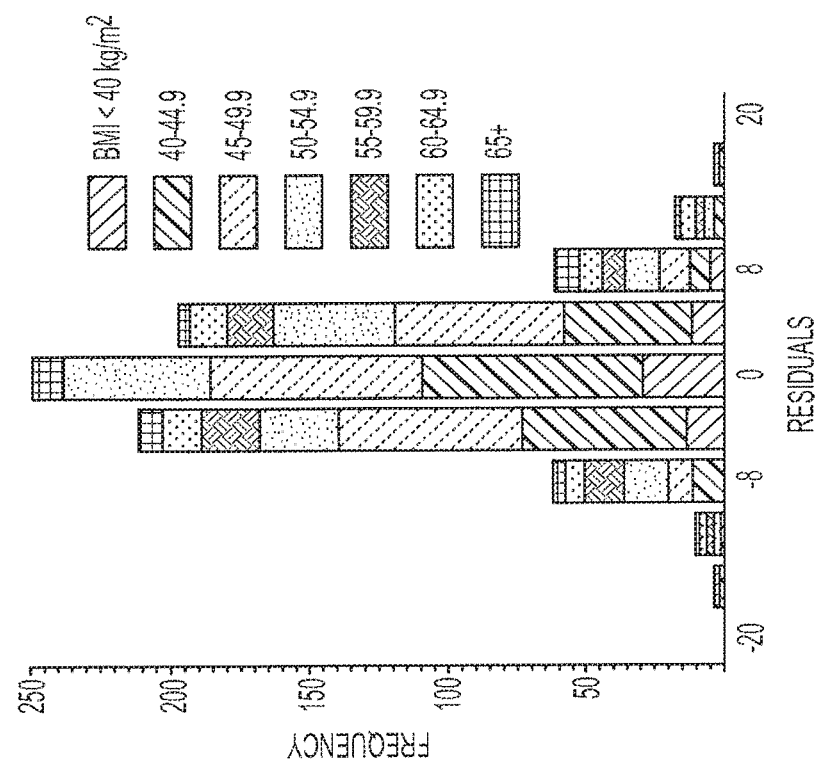
FIG. 3 is a bar graph showing no difference on the residuals (deviations of the regressing postoperative BMI on preoperative BMI from the sample mean) from the cohort of 848 patients.
Figures 7, 8:
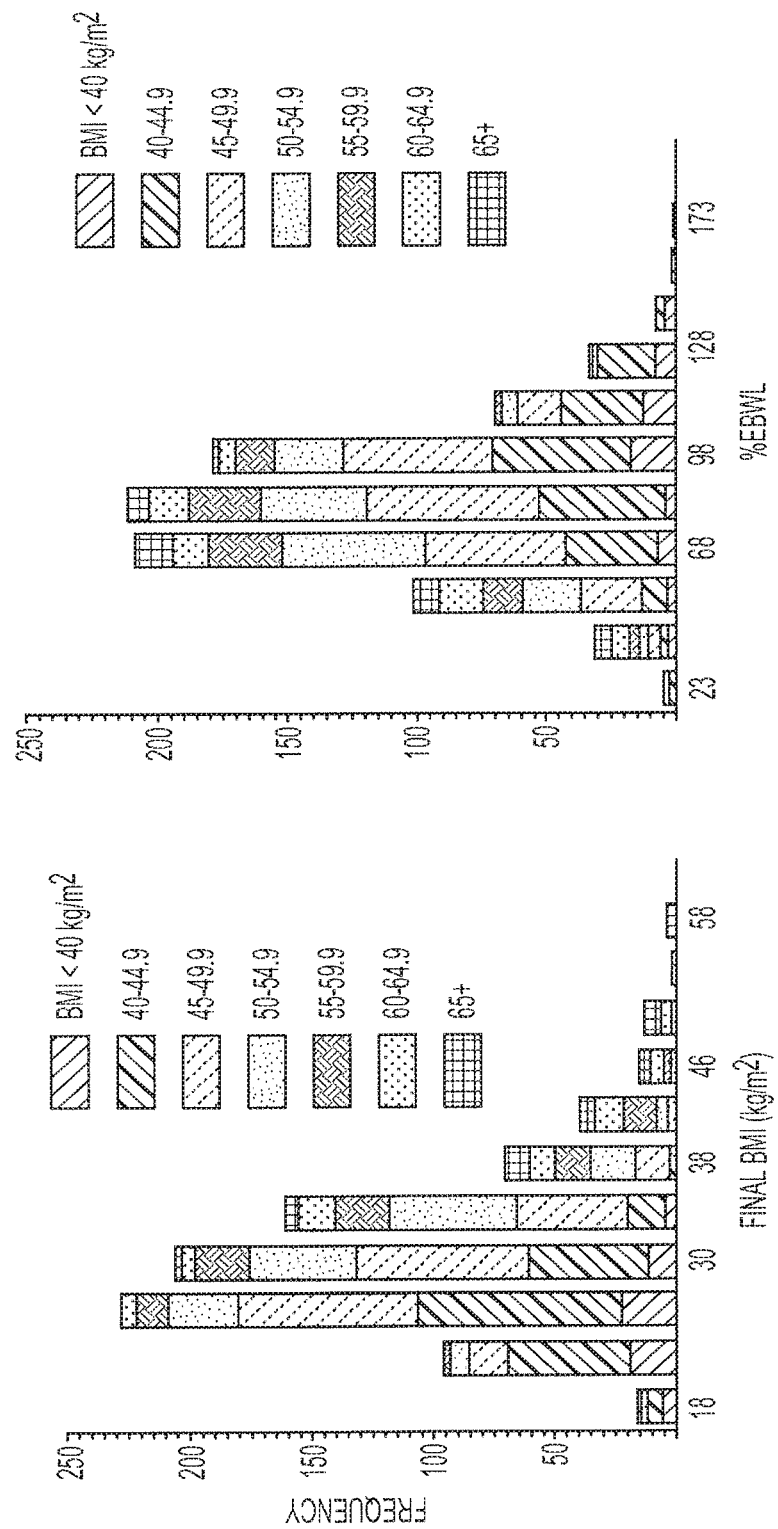
FIG. 7 is a bar graph showing final BMI obtained at 1 year postoperative of the 848 patients after 1 year postoperative.
FIG. 8 is a bar graph showing percent excess body weight lost (% EBWL) obtained at 1 year postoperative of the 848 patients after 1 year postoperative with patients at a lower pBMI losing more % EBWL at both 1 year and weight nadir.

The residuals derived from regressing postoperative BMI on preoperative BMI showed no difference across pBMI groups (r=0, p=0.9 at both one year and weight nadir; Table 3, FIG. 3). In contrast, there was a strong positive association between absolute change in weight (pounds lost or gained) and pBMI, with patients in lower BMI groups losing significantly less weight ($r_{1y}$=0.52, $p_{1y}$=3.4*10$^{-53}$; $r_{nadir}$=0.54, $p_{nadir}$=6.5*10$^{-84}$; Table 3, FIG. 4).

Figure 9:
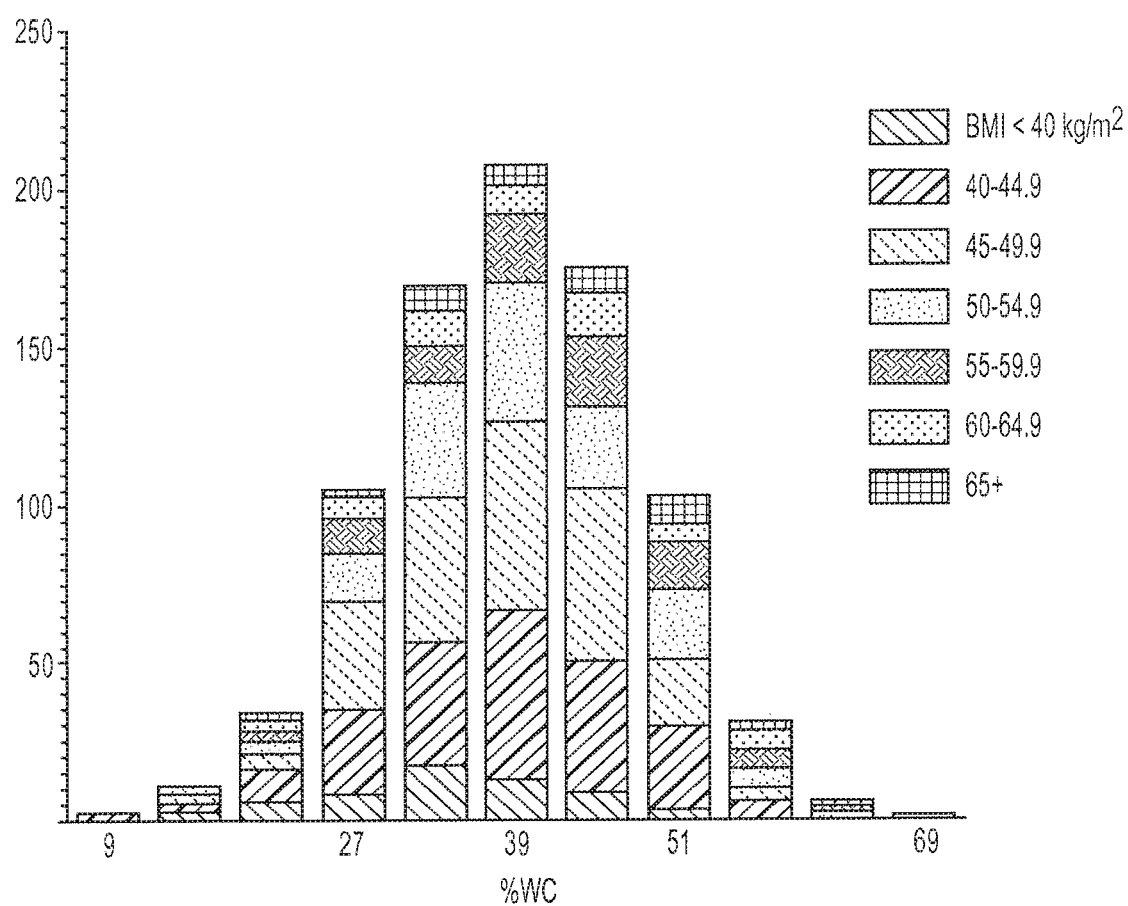
FIG. 9 is a bar graph showing percent weight change (% WC) obtained at 1 year postoperative of the 848 patients after 1 year postoperative with no significant association between pBMI group and % WC at one year, and a relatively weak association between pBMI and % WC and weight nadir.

The same pattern is observed when change in BMI, final attained weight, or final attained BMI is used (Table 3, FIGS. 3-7). When weight loss was characterized as % EBWL, the opposite pattern was observed, with patients at a lower pBMI lose more % EBWL at both 1 year and weight nadir ($r_{1y}$=−0.51, $p_{1y}$=1.0*10$^{-40}$; $r_{nadir}$=−0.43, $p_{nadir}$=6.9*10$^{-38}$; Table 3, FIG. 8). In contrast, there was no association ($r_{1y}$=0.04, $p_{1y}$=0.52) between pBMI group and % WC at one year, and a relatively weak association between pBMI and % WC and weight nadir ($r_{nadir}$=0.13, $p_{nadir}$=0.003; FIG. 9).

Similar patterns were seen when a continuous characterization of pBMI was used (Table 3). The number of pounds lost was strongly and positively correlated with pBMI at both one year ($r_{Spearman}$=0.53, p=4.3*10$^{-46}$) and at weight nadir ($r_{Spearman}$=0.55, p=5.1*10$^{-69}$); BMI units lost showed a similar pattern (Table 3). % EBWL was strongly negatively correlated with pBMI at both one year ($r_{Spearman}$=−0.52, p=3.8*10$^{-44}$) and at weight nadir ($r_{Spearman}$=−0.45, p=7.2*10$^{-43}$). In contrast, % WC was not associated with pBMI at one year ($r_{Spearman}$=0.04, p=0.33) and was only weakly associated with pBMI at weight nadir ($r_{Spearman}$=0.13, p=0.0002). While pBMI explains a substantial proportion of the variability in number of pounds lost ($r^2_{1y}$=0.36, $r^2_{nadir}$=0.39) and % EBWL ($r^2_{1y}$=0.25, $r^2_{nadir}$=0.18), it explains only a small percentage of the variability in % WC ($r^2_{1y}$=0.002, $r^2_{nadir}$=0.02).

The findings reflect the biology of weight loss after RYGB—to the extent that a higher pBMI represents a more severe form of obesity, severe obesity may "normalize" less completely after RYGB. A parallel can be drawn to other metabolic conditions, such as systolic blood pressure (SBP), where patients with more extreme levels of SBP are less likely to achieve a normal SBP and are more likely to need aggressive treatment with multiple antihypertensive treatments.

Conversely, in this study patients with a lower pBMI lost less absolute weight relative to those patients with a higher pBMI, thus appearing less "successful" if absolute pounds are chosen as the weight loss metric. Whether the association between the weight loss metric and preoperative BMI is observed for biological or artificial reasons, the results indicate a potential for confounding by preoperative BMI (hidden variables associated with BMI) when searching for novel predictors. While it may be possible to partly account for the effects of preoperative BMI through adjustment for preoperative BMI using statistical models, if a relationship between the potential predictor and preoperative BMI exists there will be the potential for collinearity, which can result in incorrect estimation of the effect size and standard error of the novel predictor. Thus, it is advantageous to utilize a weight loss metric that both minimizes the association with pBMI (unlike pounds lost or % EBWL) and that is clinically interpretable (unlike the use of residuals).

Example 5: Genetic Factors Materials and Methods

Cohort 1: To identify genetic factors contributing to weight loss after RYGB, an exploratory genome-wide association study of Caucasian individuals undergoing RYGB was performed. From February 2000 until April 2007, consent was obtained from 1018 (97%) of Massachusetts General Hospital (MGH) Weight Center patients undergoing RYGB to collect and extract DNA from tissue samples removed at the time of surgery. Cohort 1 may also be described herein as the original cohort, the GWAS cohort, the training cohort, or the training set.

In addition, one person was removed from analyses due to >10% of genetic information missing. Of the remaining 933 individuals, 806 self-identified as Caucasian. To address population structure not captured through self-identification, EIGENSTRAT (Price, A. L. et al., Nat. Genet. 38, 904-909 (2006)) was used to calculate principal components of ancestry, and identified 25 outlying samples (greater than six standard deviations) for a sample of 781 patients. Of these 781 samples, 693 had a weight nadir value, were not on weight-lowering medications after surgery, did not have cancer or other severe illness, and were thus included in the final data set. Imputation of 1,674,205 SNPs was performed using MACH software (Li, Y., Willer, C. J., Ding, J., Scheet, P. & Abecasis, G. R., Genet. Epidemiol. 34, 816-834 (2010)). A SNP was excluded from analyses if it was missing in >10% of samples, if it has less than 1% minor allele frequency, or if it was not in Hardy-Weinberg equilibrium, resulting in a SNP set of 1,943,373 SNPs.

Genotyping and Data Cleaning of Cohort 1: Samples were shipped to Rosetta Inpharmatics Gene Expression Laboratory (Seattle, Wash.) where genomic DNA was extracted from liver samples. Nine hundred fifty samples were successfully genotyped using the Illumina HumanHap 650Y BeadChip array (Illumina Corp, San Diego, Calif.). Data were converted to PLINK format (Purcell, S. et al. PLINK: a tool set for whole-genome association and population-based linkage analyses. Am. J. Hum. Genet. 81, 559-575 (2007)) and all genetic analyses were performed using this software. Using identity-by-descent (IBD) coefficients for all pairs of individuals, 36 related individuals were identified, defined as an IBD coefficient >0.125. One person per family was included for analysis, based on completeness of phenotypic and genetic information.

Cohort 2: From May 2007 until October 2009, consent was obtained from 369 Caucasian MGH Weight Center patients undergoing RYGB to collect and extract DNA from tissue samples removed at the time of surgery. Intraoperative liver was collected in RNAlater (Amion/Applied Biosystems) and stored at −80°. Operations were as described for the Cohort 1. Clinical traits were extracted from the electronic medical records, as described for the GWAS cohort. Cohort 2 may also be described herein as the replication cohort, the test cohort, or the test set.

Genotyping and Data Cleaning of Cohort 2: Samples were shipped to the Eli and Edyth Broad Institute (Cambridge, Mass.) where genomic DNA was extracted from liver samples. Three hundred sixty-nine samples were successfully genotyped using Sequenom MassARRAY (Sequenom Inc., San Diego, Calif.). Of these, 327 had a weight nadir value, were not on weight-lowering medications after surgery, did not have cancer or other severe illness, and were thus included in the final data set.

Tissue Samples: Intraoperative liver, subcutaneous fat, omental fat, and stomach tissues were collected in RNAlater (Amion/Applied Biosystems) and stored at −80° C. Operations were either open (41%) or laparoscopic (59%) RYGB. For the open procedure, the stomach was partitioned but not divided, and for the laparoscopic procedure the pouch was partitioned and divided from the remaining stomach. Otherwise, the techniques were the same, with an approximately 30 ml pouch, a 100-120 cm Roux limb fashioned in a retrocolic, retrogastric configuration, and a pancreaticobiliary limb extending approximately 75 cm beyond the ligament of Treitz.

Endpoint and Covariate Assessment: Demographic and clinical information was extracted from review of the electronic medical charts. Weight nadir was defined as the lowest weight achieved after surgery. Chart-derived nadir weight was validated through telephone interviews in a subset of patients (n=306); there was a 94% correlation between these two sources. Percent weight loss (% WL) at weight nadir was calculated by subtracting the patient's weight at nadir from his or her presurgical weight, and then dividing by the patient's presurgical weight. Percent excess body weight loss (% EBWL) was calculated by subtracting the patient's current weight from the patient's presurgical weight, and dividing this difference by the difference between the patient's presurgical weight and the patient's ideal weight.

Gene Expression Profiling: Total RNA was extracted from liver, subcutaneous fat, and omental fat tissues. Liver, subcutaneous fat and omental fat RNA was amplified and converted to fluorescently labeled cRNA that was hybridized to custom 44K DNA oligonucleotide microarrays from Agilent Technologies (Santa Clara, Calif., USA). A detailed description of the normalization and data cleaning methods has been described previously.[4] Successful profiling of 707, 870, and 916 samples from liver, subcutaneous fat, and omental fat, respectively, was performed.

Statistical Analysis: Each SNP was compared to % WL using linear regression in PLINK. SNPs within a 250 kb window of each other with a $r^2>0.5$ were not considered independent; only the strongest associated SNP for each block was considered for replication and follow-up analyses. Association results from the GWAS and replication cohorts were meta-analyzed. The association between rs17702901 and gene expression in liver, subcutaneous fat, and omental fat was determined using Kruskal-Wallace tests with adjustment for the effect of surgery year, age, race, and gender using a principle components analysis.[2] All genetic analyses were performed using PLINK. All non-genetic analyses were performed using SAS statistical software (SAS Institute, Cary, N.C.).

Animal Studies: All experiments in mice were performed in compliance with and were approved by the Institutional Animal Care and Use Committee of the Massachusetts General Hospital. We have developed a mouse model of RYGB that closely mimics the procedure in humans. At 12 weeks of age, mice with a C57BL/6 background (Jackson Laboratories, Bar Harbor, Me.) were randomized to RYGB, sham operation with post-operative ad libitum food intake, or sham operation with food restriction to match the weights of the RYGB mice weekly. In the RYGB procedure, the stomach was divided into a gastric pouch and distal stomach using a vascular clip (Ethicon Endo-Surgery, Inc., Cincinnati, Ohio). For each of the Roux and biliopancreatic limbs, the length of the intestine was 6 cm, approximating the 12-15% instestinal bypass in human RYGB. The Roux limb was then secured to the gastric fundus by a gastrojejunal anastamosis. Sham operations consisted of a laparotomy and repair. Mice were maintained on a high-fat diet (D12492 diet; Research Diets, New Brunswick, N.J.) except during the 7-14 days after surgery, when all mice were maintained on a postoperative protocol that progressed from water only to liquid diet to solid diet. Animals were individually housed in a 12 hour light, 12 hour dark cycle under controlled temperature and humidity.

At 10 weeks post-surgery, mice were sacrificed in a carbon monoxide chamber followed by cervical dislocation. Tissues were harvested immediately, flash frozen, and stored at −80°. Samples were shipped to Rosetta Inpharmatics Gene Expression Laboratory (Seattle, Wash.) where mRNA was extracted and converted to cDNA. Quantitative PCR was performed on genes of interest (to be expanded with primer and QC information as it becomes available).

Example 6: Genetic Factors Contributing to Weight Loss

Figure 10:
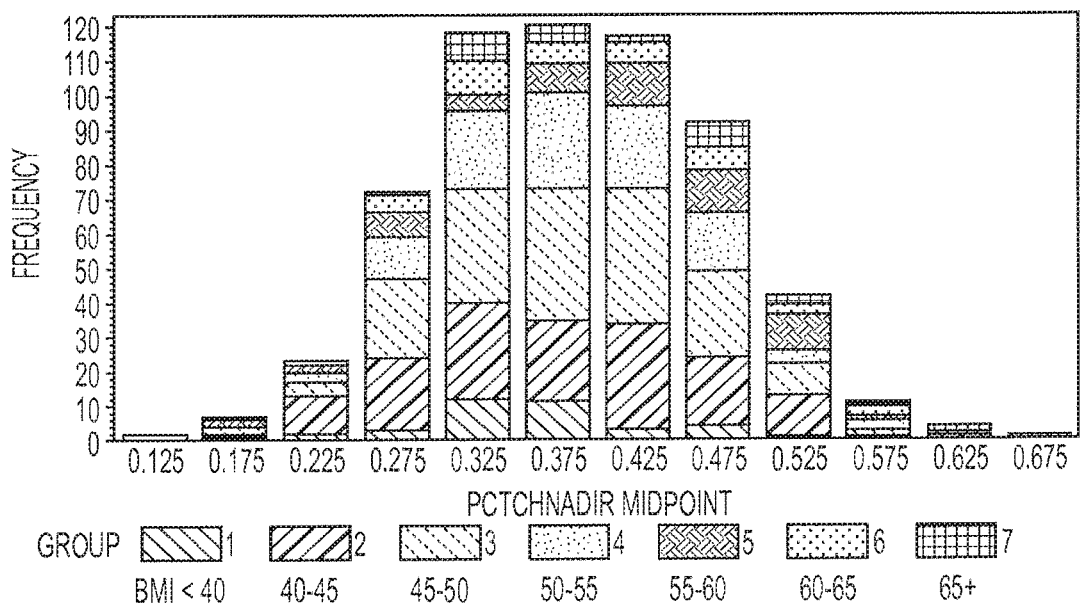
FIG. 10 is a bar graph showing percent change in weight in 858 unrelated Caucasian individuals grouped according to preoperative BMI.

To identify genetic factors contributing to weight loss after RYGB, an exploratory genome-wide association study (GWAS) of cohorts of 858 unrelated Caucasian individuals undergoing RYGB was performed. The individuals were grouped according to preoperative BMI (>40, 40-45, 45-50, 50-55, 55-60, 60-65, 65+) and percent change in weight can be found in FIG. 10 and demographic information is shown in Table 4.

TABLE 4

Pre- and post-operative characteristics of
the RYGB original and replication cohorts

| | Original Cohort | Replication Cohort | p-value |
|---|---|---|---|
| Age (years; ±SD) | 45.8 ± 11.2 | 47.1 ± 11.1 | 0.07 |
| Preoperative BMI (mean kg/m$^2$; ±SD) | 50.3 ± 8.4 | 48.1 ± 8.5 | 0.0002 |
| Sex (% female) | 73.2 | 71.7 | 0.65 |
| Diabetes (%) | 40.2 | 41.5 | 0.19 |
| BMI at weight nadir (mean kg/m$^2$; ±SD) | 30.6 ± 6.4 | 29.9 ± 6.0 | 0.32 |
| % WL at nadir (%; ±SD) | 39.0 ± 9.1 | 37.5 | 0.01 |

Single nucleotide polymorphisms (SNPs) in this cohort were genotyped using the Illumina HumanHap 650Y array. After implementing stringent quality control measures, 524,284 SNPs were available for analysis. To increase the coverage of genetic variants additional missing genotypes were imputed and applied to these imputed SNPs. The same quality control measures were performed on the genotyped SNPs. A total of 1,943,373 genetic markers were analyzed.

Figure 11:
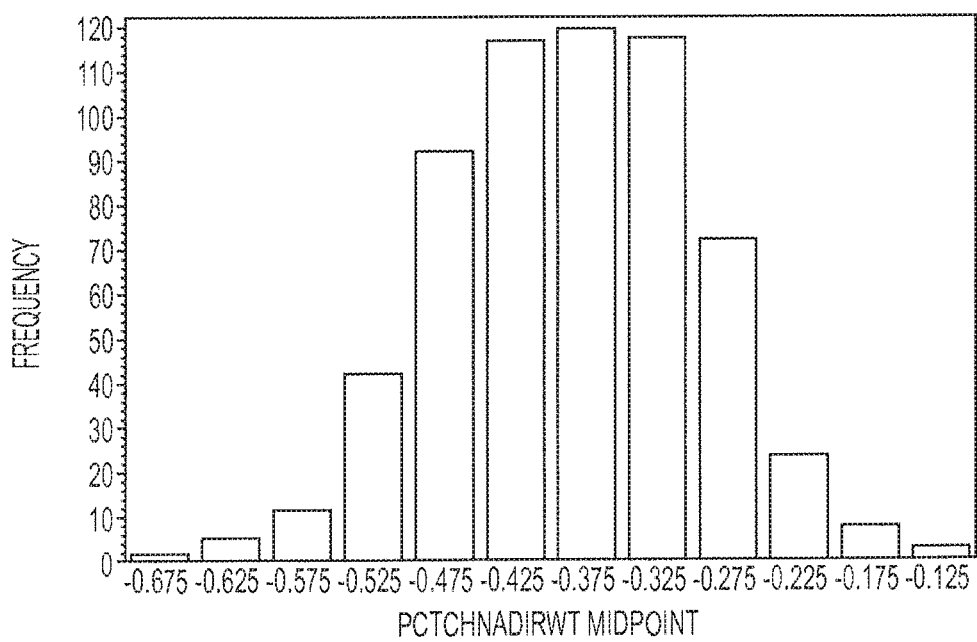
FIG. 11 is a bar graph showing percent change of weight nadir measured in a subgroup consisting of 693 patients (Cohort 1)

To minimize heterogeneity due to underlying population structure, the patients who self-identified as Caucasian using principle components analysis were analyzed. There was 97% concordance between self-identified and genetically-identified race, and only patients genetically determined to be Caucasian were included in analyses. Additionally, patients who were related, patients who had complete follow-up information, patients who were on weight-altering medications or had severe illness after surgery were excluded, leaving 693 patients (Cohort 1) for analysis. FIG. 11 shows the percent change of weight nadir measured in Cohort 1.

Figure 12:
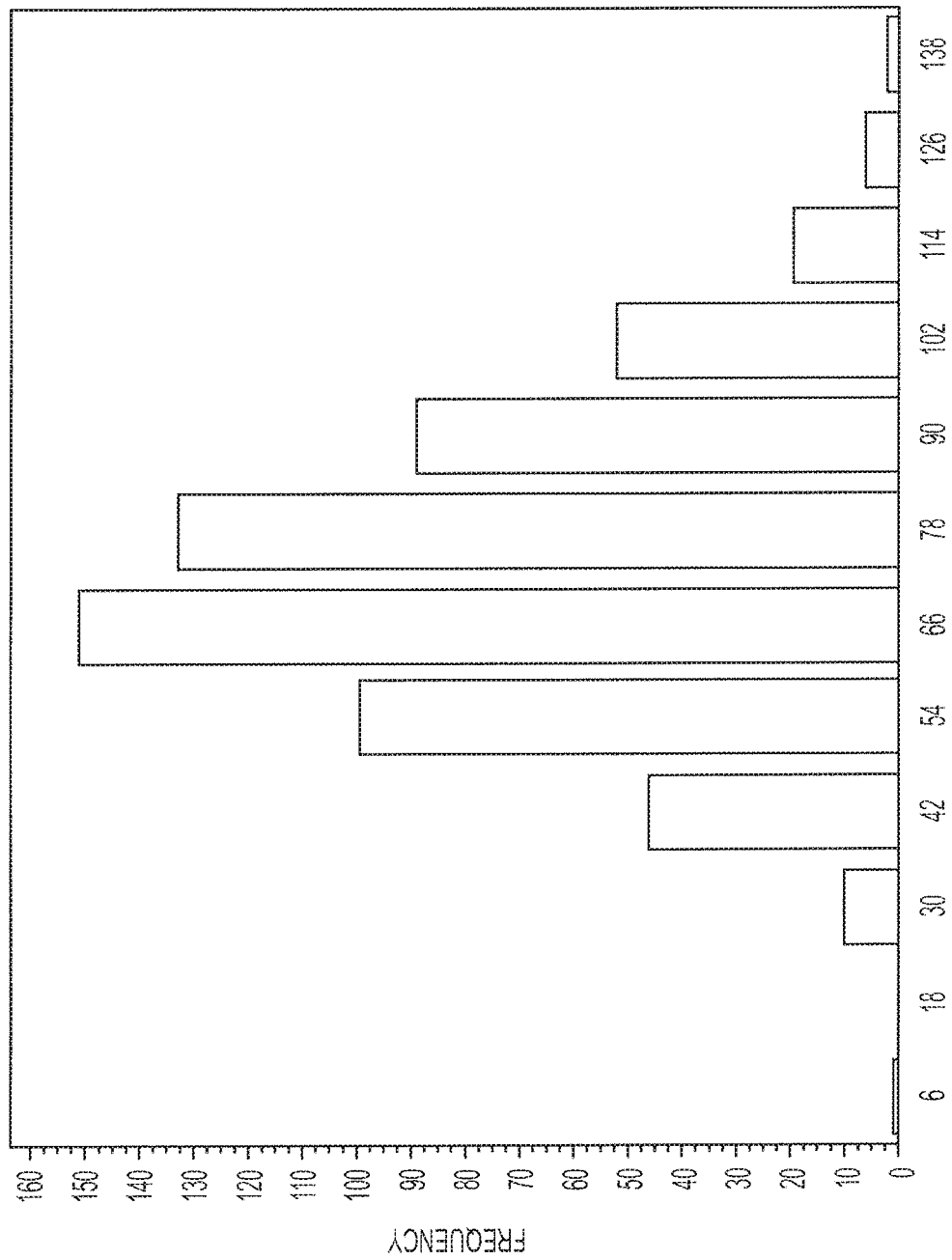
FIG. 12 is a bar graph showing percent change of weight nadir measured in an independent group of 349 Caucasian RYGB patients (Cohort 2)
Figure 13:
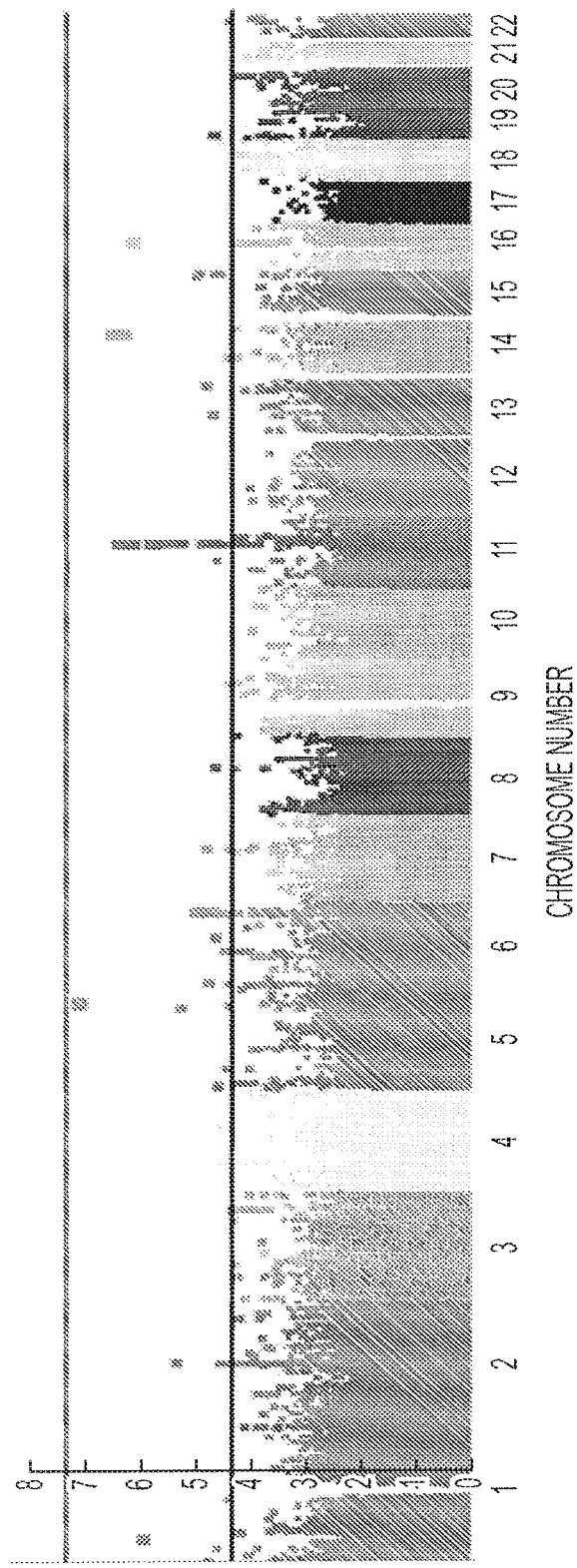
FIG. 13 is a graphical representation of 112 significant ($P<5\times10^{-5}$) single nucleotide polymorphisms (SNPs) identified in Cohort 2.

FIG. 12 shows the percent change of weight nadir measured in an independent cohort of 327 Caucasian RYGB patients (Cohort 2). One hundred and three marginally significant (P<5×10$^{-5}$) SNPs were identified (FIG. 13; Table 5), representing 26 independent loci (pairwise r$^2$<0.5) from Cohort 1. The top SNP per region was carried forward for validation in Cohort 2, 327 Caucasian RYGB patients (Table 5).

TABLE 5

Association results for 103 SNPs with p < 5.0 × 10$^{-5}$ for nadir % WL in the Cohort 1.

| Index SNP | Chr | Position | Other SNPs | Distance from index SNP (kb) | R2 with index SNP | P-value |
|---|---|---|---|---|---|---|
| rs1051508 | 5 | 159753509 | | | | 8.21e-08 |
| rs7158359 | 14 | 88664048 | | | | 3.36e-07 |
| | | | rs4904510 | -1.28 | 1.0 | 5.4e-07 |
| rs7129556 | 11 | 76977696 | | | | 4.28e-07 |
| | | | rs11605638 | -61 | 0.986 | 5.79e-06 |
| | | | rs11823651 | -46 | 0.997 | 1.6e-06 |
| | | | rs7481282 | -36 | 1.0 | 8.64e-07 |
| | | | rs11237220 | -31 | 0.997 | 5.41e-07 |
| | | | rs10899387 | -23 | 0.993 | 4.87e-07 |
| | | | rs20323951 | 14 | 1.0 | 6.51e-07 |
| | | | rs6592738 | 23 | 0.967 | 3.18e-06 |
| | | | rs10899394 | 24 | 0.961 | 4.26e-06 |
| | | | rs11237249 | 41 | 0.957 | 1.91e-06 |
| | | | rs11604207 | 67 | 0.71 | 2.5e-06 |
| | | | rs12286317 | 89 | 0.711 | 6.48e-06 |
| | | | rs7950873 | 113 | 0.709 | 4.29e-06 |
| | | | rs4344516 | 138 | 0.703 | 3.61e-05 |
| | | | rs10899404 | 163 | 0.696 | 2.95e-05 |
| | | | rs537811 | 168 | 0.696 | 2.95e-05 |
| | | | rs684813 | 195 | 0.691 | 3.86e-05 |
| | | | rs650171 | 198 | 0.696 | 2.34e-05 |
| | | | rs7123080 | 199 | 0.696 | 2.34e-05 |
| | | | rs4945220 | 228 | 0.695 | 2.29e-05 |
| | | | rs7951033 | 234 | 0.695 | 2.29e-05 |
| rs7185923 | 16 | 49802988 | | | | 8.08e-07 |
| rs2994537 | 1 | 44650917 | | | | 1.17e-06 |
| rs934760 | 2 | 122002672 | | | | 4.6e-06 |
| | | | rs6712661 | -183 | 0.907 | 3.19e-05 |
| | | | rs12622908 | -182 | 0.906 | 4.58e-05 |
| | | | rs735483 | -181 | 0.908 | 3.19e-05 |
| | | | rs12615396 | -176 | 0.908 | 3.19e-05 |
| | | | rs12615068 | -171 | 0.907 | 4.58e-05 |
| | | | rs7601226 | -171 | 0.908 | 3.19e-05 |
| | | | rs17006394 | -168 | 0.907 | 4.58e-05 |
| | | | rs13414513 | -167 | 0.908 | 3.19e-05 |
| | | | rs9653407 | -166 | 0.908 | 3.19e-05 |
| | | | rs7564564 | -152 | 0.898 | 4.68e-05 |
| | | | rs12711551 | -123 | 0.917 | 3.22e-05 |
| | | | rs17006485 | -79 | 0.902 | 3.1e-05 |
| | | | rs2164796 | -67 | 0.918 | 3.35e-05 |
| | | | rs2118387 | -67 | 0.918 | 3.35e-05 |
| | | | rs13000440 | -49 | 0.918 | 3.35e-05 |
| | | | rs724403 | -48 | 0.918 | 3.5e-05 |
| | | | rs13413270 | -46 | 0.918 | 3.35e-05 |
| | | | rs6711921 | -13 | 0.918 | 3.35e-05 |
| | | | rs9678017 | 2 | 0.918 | 3.35e-05 |

TABLE 5-continued

Association results for 103 SNPs with p < 5.0 × $10^{-5}$ for nadir % WL in the Cohort 1.

| Index SNP | Chr | Position | Other SNPs | Distance from index SNP (kb) | R2 with index SNP | P-value |
|---|---|---|---|---|---|---|
| | | | rs10177322 | 4 | 0.918 | 3.47e−05 |
| | | | rs7580531 | 19 | 0.909 | 4.11e−05 |
| | | | rs12711559 | 120 | 0.859 | 3.7e−05 |
| rs1104959 | 5 | 149722429 | | | | 5.83e−06 |
| rs9403832 | 6 | 147296219 | | | | 9.77e−06 |
| | | | rs7383179 | −6.69 | 1 | 9.77e−06 |
| | | | rs9322082 | −2.17 | 0.985 | 1.37e−05 |
| | | | rs11155492 | −0.453 | 0.985 | 1.37e−05 |
| | | | rs9403834 | 5 | 1 | 1.35e−05 |
| | | | rs11155494 | 5.34 | 1 | 1.35e−05 |
| | | | rs1408577 | 12.6 | 0.98 | 1.93e−05 |
| | | | rs7742886 | 13.8 | 0.995 | 1.38e−05 |
| | | | rs4267966 | 17.7 | 0.956 | 4.74e−05 |
| | | | rs4452660 | 21.9 | 0.972 | 2.23e−05 |
| | | | rs4323329 | 22.3 | 0.972 | 2.23e−05 |
| | | | rs9377038 | 27.4 | 0.957 | 3.05e−05 |
| | | | rs7775644 | 47.8 | 0.667 | 2.11e−05 |
| | | | rs9322085 | 58.6 | 0.632 | 4.17e−05 |
| | | | rs6570781 | 58.8 | 0.6 | 3.13e−05 |
| | | | rs6902235 | 60.8 | 0.611 | 2.31e−05 |
| | | | rs7745042 | 66.9 | 0.6 | 2.18e−05 |
| rs8032450 | 15 | 87573927 | | | | 1.09e−05 |
| rs17702901 | 15 | 90731415 | | | | 1.19e−05 |
| | | | rs17646351 | −3.58 | 1 | 3.17e−05 |
| | | | rs17646434 | 0.93 | 1 | 2.38e−05 |
| | | | rs17702960 | 2.12 | 1 | 2.38e−05 |
| | | | rs17646492 | 3.45 | 1 | 3.21e−05 |
| rs588217 | 11 | 77261024 | | | | 1.36e−05 |
| | | | rs621456 | −30.3 | 0.805 | 3.93e−05 |
| | | | rs4085813 | −15.8 | 0.985 | 2.24e−05 |
| | | | rs648601 | 3.53 | 0.985 | 1.86e−05 |
| rs6554217 | 4 | 55672161 | | | | 1.49e−05 |
| | | | rs4450992 | 0.861 | 0.979 | 3.72e−05 |
| rs9357419 | 6 | 12690973 | | | | 1.79e−05 |
| | | | rs7744769 | −1.12 | 1 | 4.29e−05 |
| rs11260025 | 19 | 7687753 | | | | 2.21e−05 |
| | | | rs8111760 | 0.267 | 1 | 2.35e−05 |
| rs7749399 | 6 | 96086077 | | | | 2.39e−05 |
| rs443673 | 5 | 3265963 | | | | 2.62e−05 |
| rs12803675 | 11 | 49858702 | | | | 2.74e−05 |
| rs13380914 | 18 | 69312767 | | | | 2.94e−05 |
| | | | rs1954888 | −8.71 | 1 | 4.08e−05 |
| | | | rs12968184 | 44.7 | 0.626 | 3.31e−05 |
| rs10518316 | 4 | 120241167 | | | | 2.98e−05 |
| rs6911409 | 6 | 73910091 | | | | 3.52e−05 |
| | | | rs6911751 | 0.198 | 1 | 4.87e−05 |
| rs4703388 | 5 | 34834358 | | | | 3.92e−05 |
| | | | rs16867581 | 1.58 | 1 | 3.92e−05 |
| | | | rs12659689 | 1.75 | 1 | 3.92e−05 |
| rs1952291 | 14 | 45410504 | | | | 4.3e−05 |
| rs1289666 | 1 | 117350312 | | | | 4.35e−05 |
| rs10242229 | 7 | 92996322 | | | | 4.37e−05 |
| | | | rs2157814 | 1.37 | 1 | 4.73e−05 |
| rs11788785 | 9 | 96111183 | | | | 4.53e−05 |
| rs1883264 | 22 | 41834344 | | | | 4.59e−05 |
| rs12696123 | 3 | 163099074 | | | | 4.71e−05 |
| | | | rs2029600 | −2.47 | 1 | 4.71e−05 |

Figure 14:
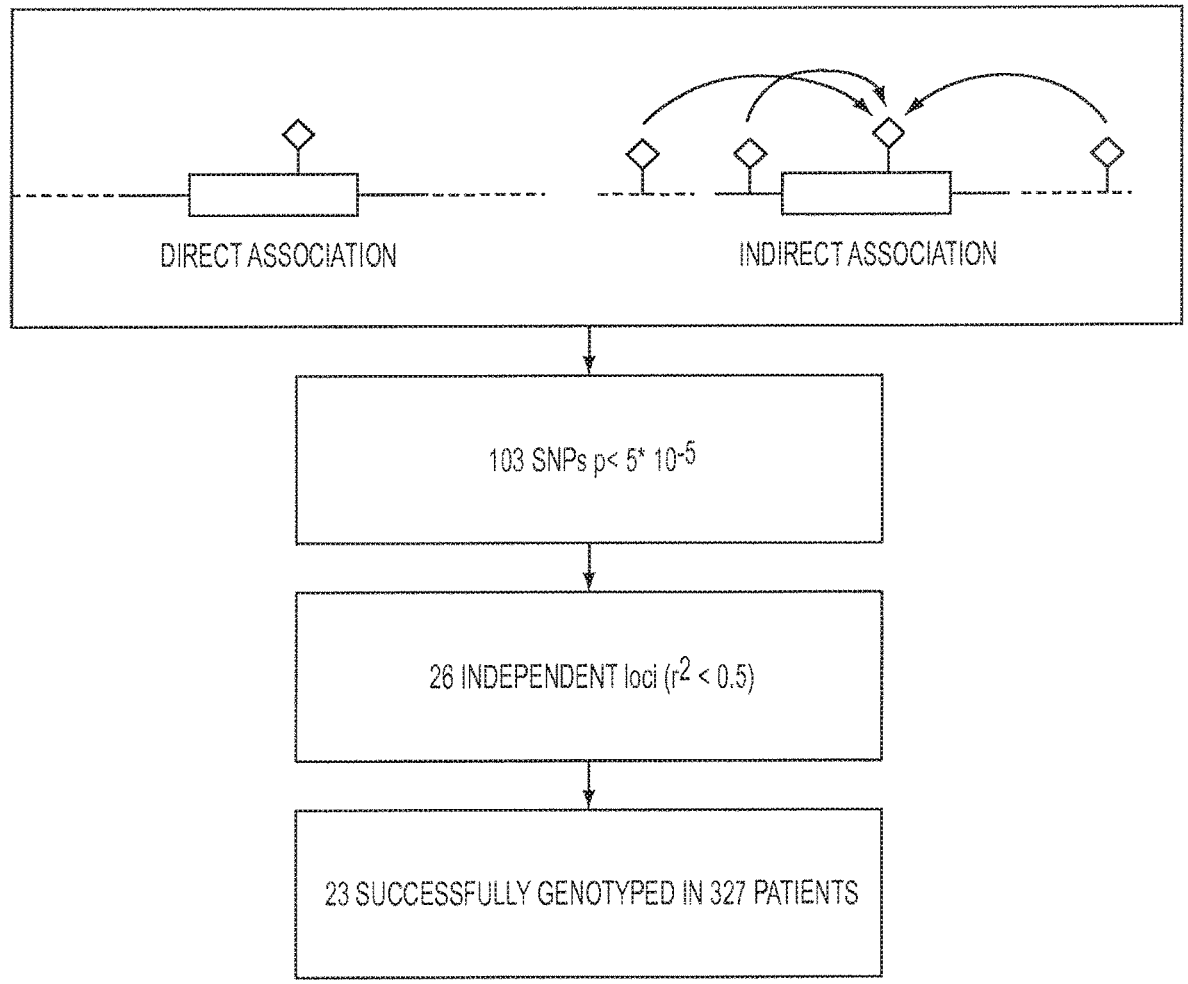
FIG. 14 is a flow diagram illustrating direct or indirect association of the SNP with surrounding loci.

The top SNP per region underwent validation in Cohort 2. Twenty-three mutations were determined using Sequenom MassARRAY, see FIG. 14. The association between SNPs and percent total weight loss (% WL) at the lowest weight (weight nadir) after RYGB were analyzed using linear regression models. A genomic control inflation factor of 1.00 was observed, indicating there was no inflation of test statistics due to population stratification. Results of the original and validation cohorts were meta-analyzed using fixed effects models.

Figure 15:
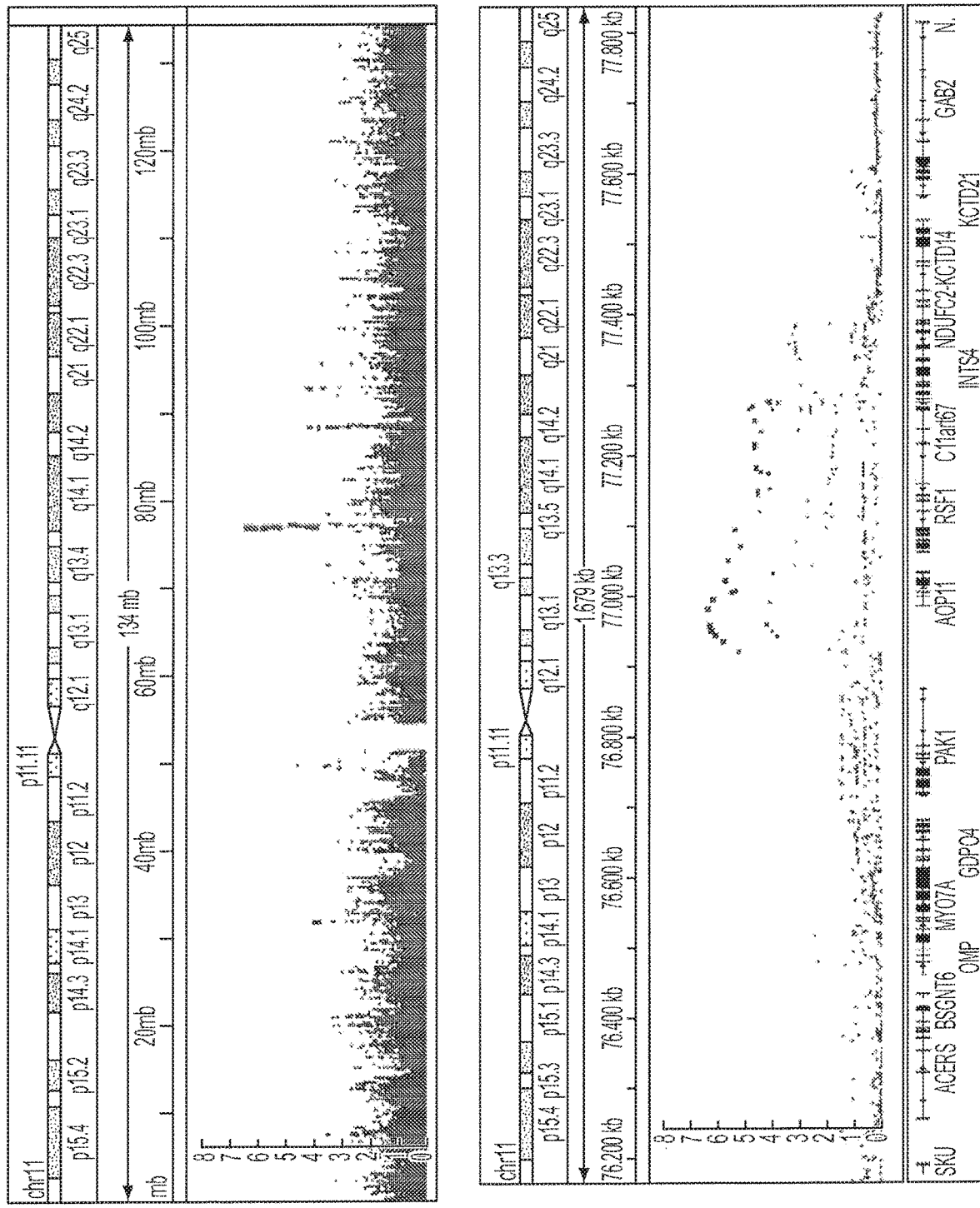
FIG. 15 is a graphical representation of chromosome 11 with the SNPs identified as having significant association with percent total weight loss (% WL) at the lowest weight (weight nadir) after RYGB.

Multiple regions on several chromosomes, such as chromosome 11, were found to have numerous SNPs or "clouds" of SNPs with signification association to percent total weight loss (% WL) at the lowest weight (weight nadir) after RYGB (FIG. 15). Additionally, a SNP at 15q26.1, rs17702901 was identified as being significantly associated with % WL after RYGB ($P_{replication}$=0.002; $P_{meta-analyzed}$=7.4×10$^{-8}$). The magnitude of effect was strikingly similar across the two cohorts, with betas of −6.70 and −6.52, respectively (Table 6).

TABLE 6

SNPs Associated with % WC at Nadir.

| SNP | Chr | Cohort 1 | | Cohort 2 | | Meta-Analyzed | |
|---|---|---|---|---|---|---|---|
| | | p-value | β | p-value | β | p-value | β |
| rs7158359 | 14 | 3.361E−07 | −3.029 | 0.6593 | −0.4075 | 0.00000456 | 2.2731 |
| rs7129556 | 11 | 4.276E−07 | −2.803 | 0.441 | −0.6013 | 0.000003866 | 2.073 |
| rs10899387 | 11 | 4.873E−07 | −2.876 | 0.5991 | 4.336 | | |
| rs934760 | 2 | 0.000004595 | −4.276 | 0.68 | 0.5647 | | |
| rs1104959 | 5 | 0.000005829 | 7.748 | 0.6605 | 0.8592 | 0.0001832 | 4.7901 |
| rs17702901 | 15 | 0.00001188 | −6.703 | 0.002259 | −6.524 | 7.439E−08 | 6.6422 |
| rs588217 | 11 | 0.00001363 | −2.547 | 0.4659 | −0.5852 | 0.00006972 | 1.8713 |
| rs9357419 | 6 | 0.0000179 | −2.95 | 0.5694 | 0.5581 | 0.001292 | 1.8029 |

Because the physiological mechanisms of weight gain to generate obesity and weight loss after RYGB may be related, previously reported and validated BMI loci associated with weight loss after RYGB in humans were assessed. None of the 32 previously reported BMI loci was associated with weight loss after surgery, nor did loci previously reported to be associated with diabetes (Table 8).

TABLE 7

Association results for SNPs previously identified as associated with obesity.

| SNP | Closest Genes | Chr | Position | Cohort 1 | | Cohort 2 | | Combined | |
|---|---|---|---|---|---|---|---|---|---|
| | | | | Beta | P-value | Beta | P-value | Beta | P-value |
| rs3810291 | TMEM160, ZC3H4 | 19 | 52260843 | 0.8816 | 0.09116 | 1.627 | 0.03188 | 1.1222 | 0.008874 |
| rs9816226 | ETV5 | 3 | 187317193 | 1.18 | 0.08907 | 0.04788 | 0.9598 | | |
| rs713586 | RBJ, ADCY3, POMC | 2 | 25011512 | 0.2023 | 0.678 | 1.117 | 0.1079 | | |
| rs206936 | NUDT3, HMGA1 | 6 | 34410847 | 0.8864 | 0.1432 | −1.133 | 0.1898 | 0.2204 | 0.6562 |
| rs12444979 | GPRC5B, IQCK | 16 | 19841101 | 0.4432 | 0.5179 | 0.1076 | 0.9165 | 0.3396 | 0.551 |
| rs3817334 | MTCH2, NDUFS3, CUGBP1 | 11 | 47607569 | 0.7219 | 0.1428 | 0.2568 | 0.7194 | 0.5722 | 0.1579 |
| rs2890652 | LRP1B | 2 | 142676401 | | | 1.07 | 0.2291 | | |
| rs4929949 | RPL27A, TUB | 11 | 8561169 | | | −1.146 | 0.1109 | | |
| rs2112347 | FLJ35779, HMGCR | 5 | 75050998 | −0.252 | 0.6206 | −1.337 | 0.08203 | 0.5839 | 0.1684 |
| rs1558902 | FTO | 16 | 52361075 | −0.1002 | 0.8373 | 0.7299 | 0.322 | | |
| rs7359397 | SH2B1, APOB48R, SULT1A2, AC138894.2, ATXN2L, TUFM | 16 | 28793160 | | | −0.3648 | 0.6172 | | |
| rs1555543 | PTBP2 | 1 | 96717385 | −0.1002 | 0.8373 | 0.7299 | 0.322 | | |
| rs10767664 | BDNF | 11 | 27682562 | −0.6604 | 0.2437 | −3.103 | 0.08731 | 0.8798 | 0.1033 |
| rs29941 | KCTD15 | 1 | 39001372 | | | | | | |
| rs10968576 | LRRN6C | 9 | 28404339 | −0.2771 | 0.6109 | 0.9994 | 0.1874 | 0.1585 | 0.7198 |
| rs2287019 | QPCTL, GIPR | 19 | 50894012 | −0.2966 | 0.6254 | 0.3084 | 0.7506 | 0.1261 | 0.8064 |
| rs4836133 | ZNF608 | 5 | 124360002 | 0.1233 | 0.8095 | 0.272 | 0.6757 | | |
| rs2867125 | TMEM18 | 2 | 612827 | 1.131 | 0.09057 | 1.074 | 0.2894 | 1.1137 | 0.04559 |
| rs2241423 | MAP2K5, LBXCOR1 | 15 | 65873892 | 0.8342 | 0.1576 | −0.6305 | 0.4646 | 0.3667 | 0.451 |
| rs11847697 | PRKD1 | 14 | 29584863 | 1.22 | 0.3201 | 5.553 | 0.002041 | 2.6094 | 0.009877 |
| rs4771122 | MTIF, GTF3A | 13 | 26918180 | −0.05777 | 0.9246 | 2.139 | 0.02102 | 0.6115 | 0.2295 |
| rs10150332 | NRXN3 | 14 | 79006717 | −0.7973 | 0.1883 | 0.3959 | 0.6395 | 0.3922 | 0.4254 |
| rs13078807 | CADM2 | 3 | 85966840 | −0.4147 | 0.4005 | −0.2349 | 0.7358 | | |
| rs1514175 | TNNI3K | 1 | 74764232 | −0.4147 | 0.4005 | −0.2349 | 0.7358 | | |
| rs7138803 | FAIM2 | 12 | 48533735 | −0.1494 | 0.7614 | −1.144 | 0.1332 | 0.4429 | 0.2834 |
| rs10938397 | GNPDA2 | 4 | 44877284 | 0.484 | 0.325 | 2.172 | 0.2447 | | |
| rs571312 | MC4R | 18 | 55990749 | −0.3649 | 0.5281 | −0.1409 | 0.8599 | 0.2878 | 0.5387 |
| rs887912 | FANCL | 2 | 59156381 | | | −0.9561 | 0.2035 | | |
| rs13107325 | SLC39A8 | 4 | 103407732 | | | −1.233 | 0.3084 | | |
| rs543874 | SEC16B | 1 | 176156103 | 0.4599 | 0.444 | 0.453 | 0.5792 | | |
| rs987237 | TFAP2B | 6 | 50911009 | −0.1616 | 0.7928 | 1.557 | 0.07323 | 0.4139 | 0.4091 |
| rs2815752 | NEGR1 | 1 | 72585028 | −0.1446 | 0.7788 | −1.347 | 0.06805 | | |

Figure 16:
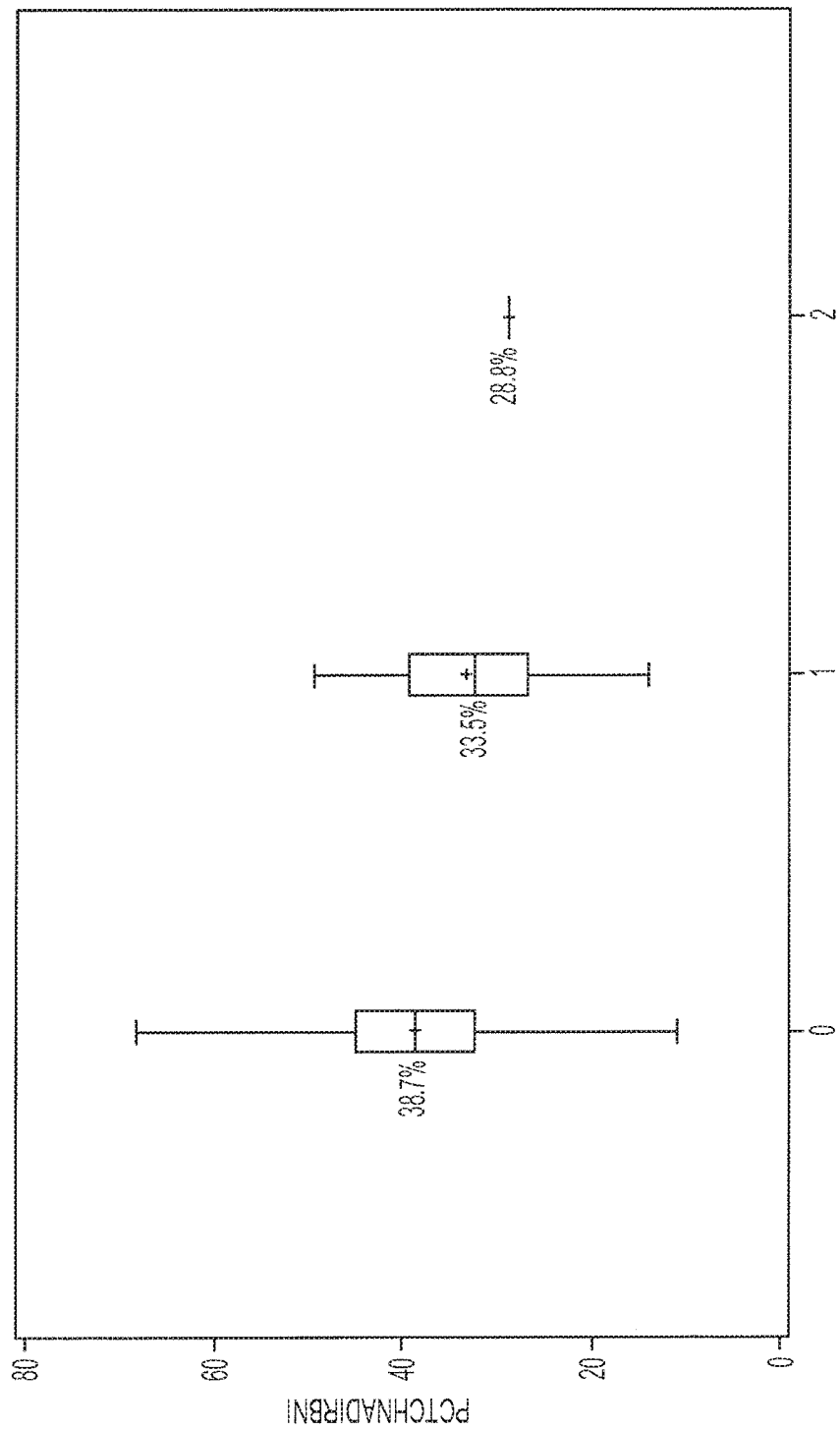
FIG. 16 is graph showing the association of carrying the minor allele (MA), rs17702901, and percent weight change at nadir in patients homozygous null for MA, heterozygous for MA or homozygous for MA.

After pooling data from the two cohorts (n=953), patients lacking the minor allele (MA) of rs17702901 lost an average of 38.7% of their body weight, while patients carrying a single copy of this mutation (n=52, 5.0% of the population) lost an average of 33.5%. The sole patient with two copies of the MA had a percent weight loss of 28.8% (FIG. 16).

Figure 17:
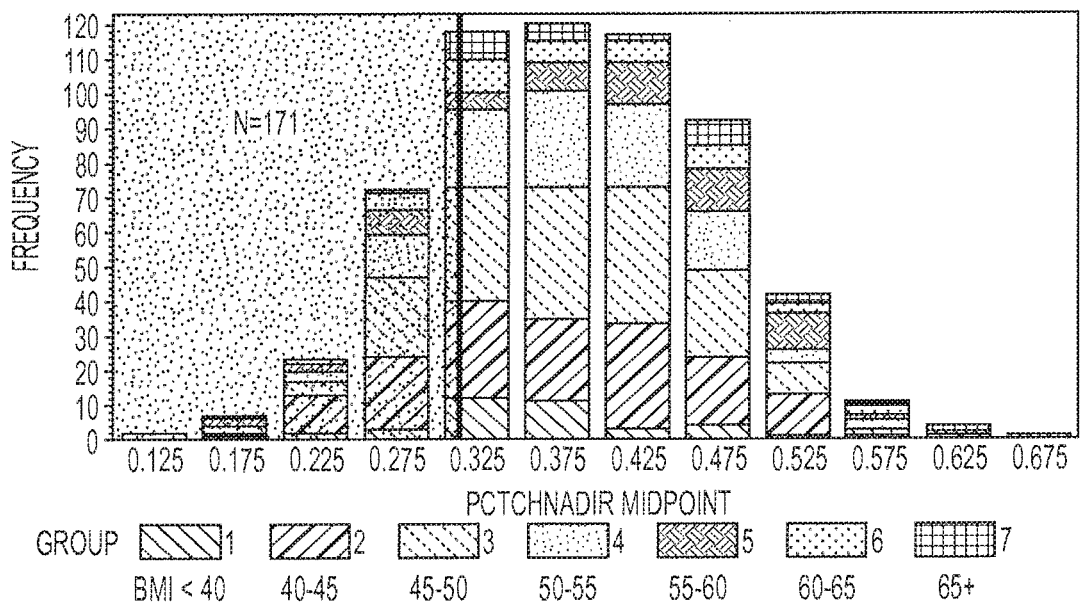
FIG. 17 is a bar graph showing percent weight change at nadir measured in pooled data from combination of Cohort 1 and Cohort 2 (953 RYGB patients). The shaded area identifies 171 patients having % WL categorized as less than or greater than or equal to 30% at weight nadir.
Figure 18:
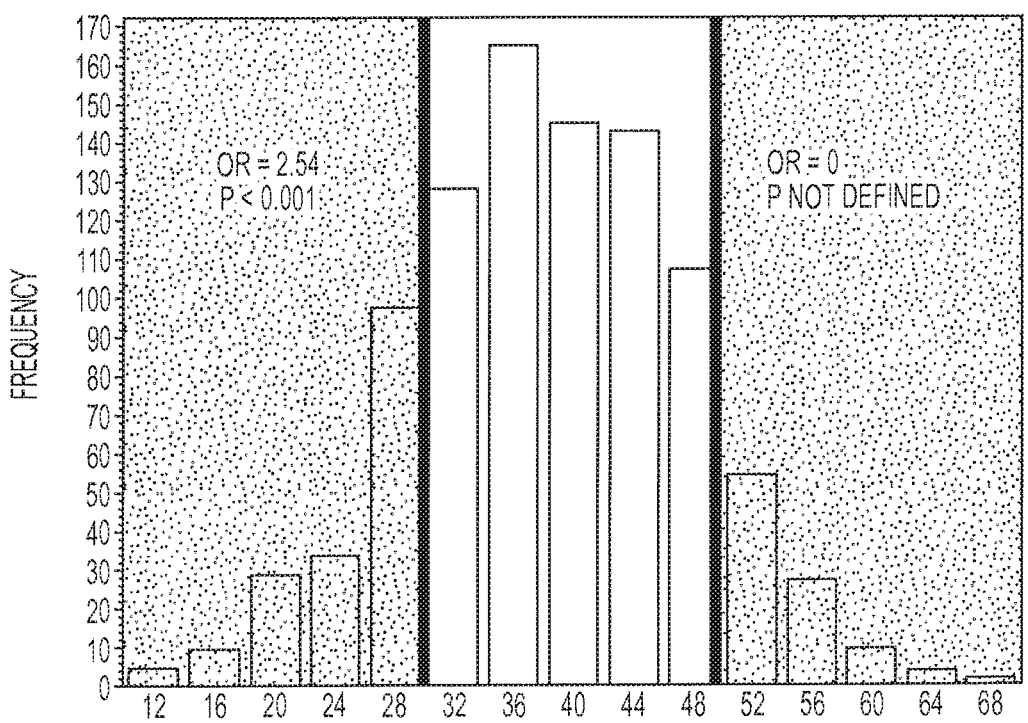
FIG. 18 is a bar graph showing percent weight loss with patients carrying at least one copy of the MA being 2.54 times more likely to fall below 30% WL (left shaded area) and no patients with this polymorphism lost more than 50% of his or her weight (right shaded area)

To examine the potential predictive utility of this SNP for discriminating amongst patients, % WL was categorized as less than or greater than or equal to 30% at weight nadir (n=171, 17.9%), FIG. 17. Patients with at least one copy of the MA were 2.54 times more likely to fall below 30% WL, than patients with no copies of the MA (P<0.001)(left shaded area in FIG. 18). Notably, no patients with this polymorphism lost more than 50% of his or her weight (corresponding to the upper 10% of the weight loss distribution)(right shaded area in FIG. 18).

Example 7: Genetic Models

Figure 19:
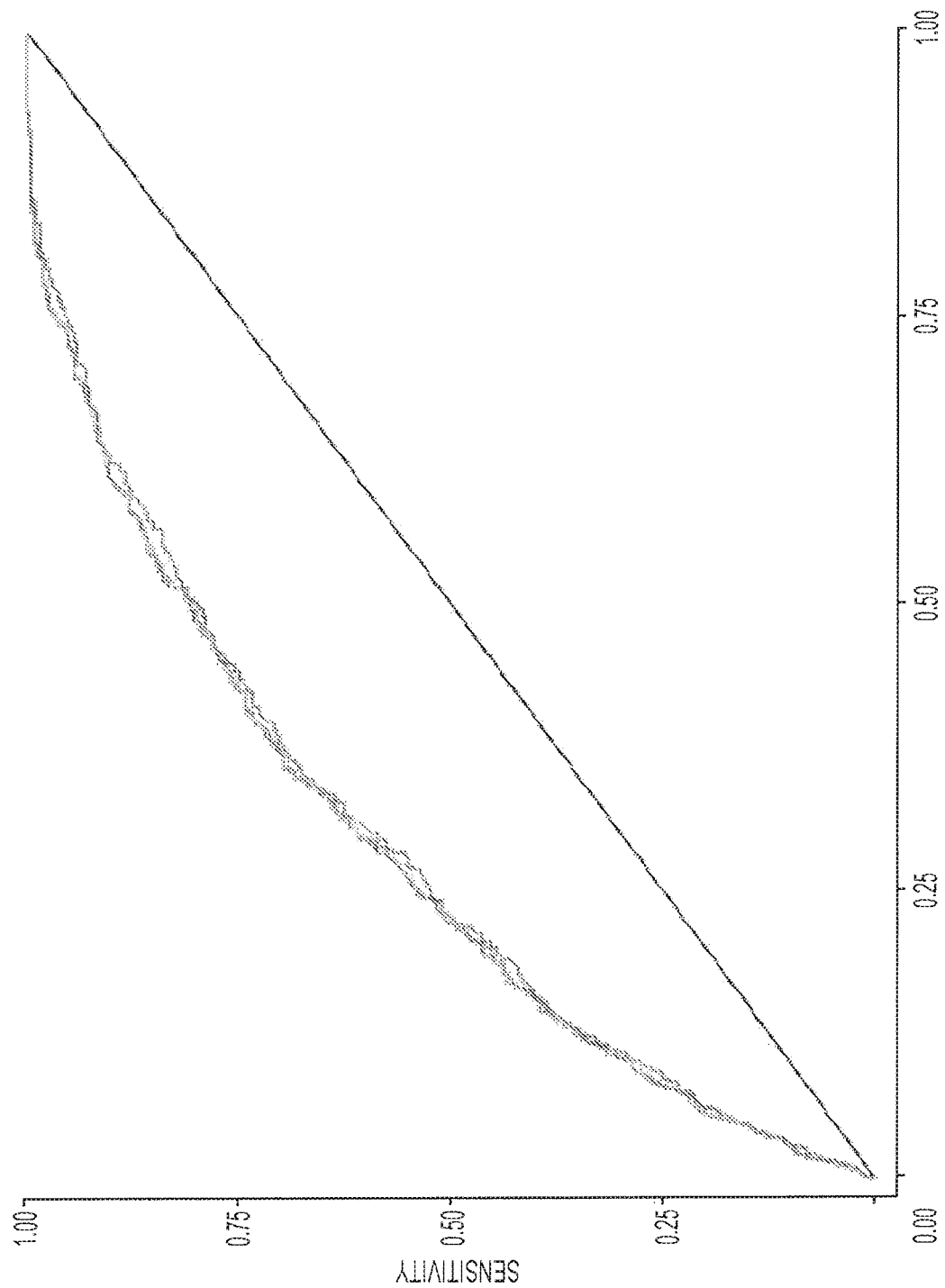
FIG. 19 is an area under the receiver operating characteristic curve (AUROC) showing that inclusion of rs17709201 has a higher probability of being a predictor of weight loss than rs17709201 as a random positive influence on weight loss.

The predictive ability of this SNP was further tested by adding this marker to a clinical model for predicting weight loss after RYGB, Table 8. The model was constructed by selecting one or more SNPs that met specific p-value criteria and then using backward and stepwise regression. The coefficients for each variable were determined using the training population (Cohort 1) and then the genetic information was entered into a regression model to determine the improvement genetics has on weight loss predictions. In a multivariable model that included age, sex, preoperative BMI (pBMI), and diabetes as variables, the area under the receiver operating characteristic curve (AUROC) was calculated as 0.620. After inclusion of rs17709201 in the model, the AUROC improved to 0.633 (FIG. 19), showing that inclusion of rs17709201 has a higher probability of being a predictor of weight loss than rs17709201 as a random positive influence on weight loss.

TABLE 8

Model Performance.

|  | Clinical | Clinical + rs17702901 |
|---|---|---|
| Percent Concordant | 61.2 | 62.6 |
| Percent Discordant | 38.2 | 36.6 |
| Percent Tied | 0.6 | 0.8 |
| AUROC/C-statistic | 0.665 | 0.676 |

To further demonstrate the predictive ability of incorporating genetic information with clinical data, multivariable models were tested by adding multiple SNPs to a clinical model for predicting weight loss after RYGB, Table 9. Variables for the clinical model included age, sex, diabetes, and preoperative BMI (pBMI). Variables for the genetic model included all of the variables in the clinical model with the addition of the following genetic variables: rs1108723, rs11739371, rs11942914, rs12425125, rs17710780, rs2383289, rs3734399, rs4325727, rs4603757, rs6737079, rs6911751, rs6925786, rs9474779. Similar to the model with one SNP, the multi-SNP model was constructed by selecting multiple SNPs that met specific p-value criteria and then using backward and stepwise regression. For each model, coefficients for each variable were determined using the training population (Cohort 1). Validation that these coefficients are applicable to other data sets was assessed using Cohort 2 as a test set of data. Data from Cohort 2 was not used in establishing the coefficients and therefore serves as a valid test case. For the clinical multivariable model that included age, sex, diabetes, and preoperative BMI (pBMI) as variables, the AUROC score was calculated to be 0.665 in Cohort 1. The AUROC score in the test population, Cohort 2, showed significant similarity (0.699) and affirmed the performance of the model. For the genetic multivariable model that included clinical and genetic factors, the AUROC was significantly better (0.971) after determining the optimal coefficients to this model in the training set (Cohort 1). Using the genetic multivariable model with the coefficients derived from Cohort 1, the AUROC in the test set (Cohort 2) was also improved (0.795) over the respective AUROC scores based on clinical data alone, verifying that inclusion of multiple SNPs (rs1108723, rs11739371, rs11942914, rs12425125, rs17710780, rs2383289, rs3734399, rs4325727, rs4603757, rs6737079, rs6911751, rs6925786, rs9474779) significantly improves weight loss predictions.

TABLE 9

Model Performance.

|  | Cohort 1-Clinical | Cohort 2-Clinical | Cohort 1-Clinical + SNPs | Cohort 2-Clinical + SNPs |
|---|---|---|---|---|
| Percent Concordant | 65.7 | 69.3 | 96.3 | 79.2 |
| Percent Discordant | 32.7 | 29.6 | 2.0 | 20.2 |
| Percent Tied | 1.6 | 1.0 | 1.7 | 0.6 |
| AUROC/C-statistic | 0.665 | 0.699 | 0.971 | 0.795 |

To determine the potential biological function of this SNP, the presence of the MA associated with expression of any of ~44,000 gene expression transcripts in liver, omental fat tissue, and subcutaneous fat tissue was examined. No obvious association between rs17702901 and expression of other transcripts was found upon initial inspection, including expression of two genes located closest to rs17702901-ST8SIA2 (~6.7 kilobases (kb) downstream of rs17702901) and SLCO3A1 (~223 kb upstream of rs17702901).

Because expression of transcripts may be influenced by the patient's physiological state, expression of these genes in a controlled environment was analyzed. Expression of ST8SIA2 and SLCO3A1 were previously analyzed in a mouse model of RYGB (Hatoum, I. J. et al., *J Clin Endocrinol Metab*, vol 97, pp E1023-E1031, 2012). Age- and sex-matched animals were randomized to RYGB, sham operation with ad libitum food intake (SO-AL), or sham operation with food restriction to match the weight of the RYGB animals (SO-WM). After ten weeks, animals were sacrificed and expression was determined in upper bypassed limb (BL), the upper Roux limb (RL), the upper common limb (CL), the colon, the liver, the muscle, the epididymal fat and the subcutaneous fat.

Expression of ST8SIA2 was not significantly altered in any tissue after RYGB relative to SO-AL and SO-WM. In contrast, expression of SLCO3A1 was significantly altered in the RL, CL, and subcutaneous fat after RYGB, relative to ad libitum-fed shams. It appeared that effects in RL and CL were weight loss-independent, as these remained significant in the RYGB compared to SO-WM animals. The effects in the BL and colon were also significant in Roux animals compared to weight matched animals. The biological relationship between rs17702901 and regulation of ST8SIA2 or SLCO3A1 does not appear to be in strong linkage disequilibrium.

Figure 20:
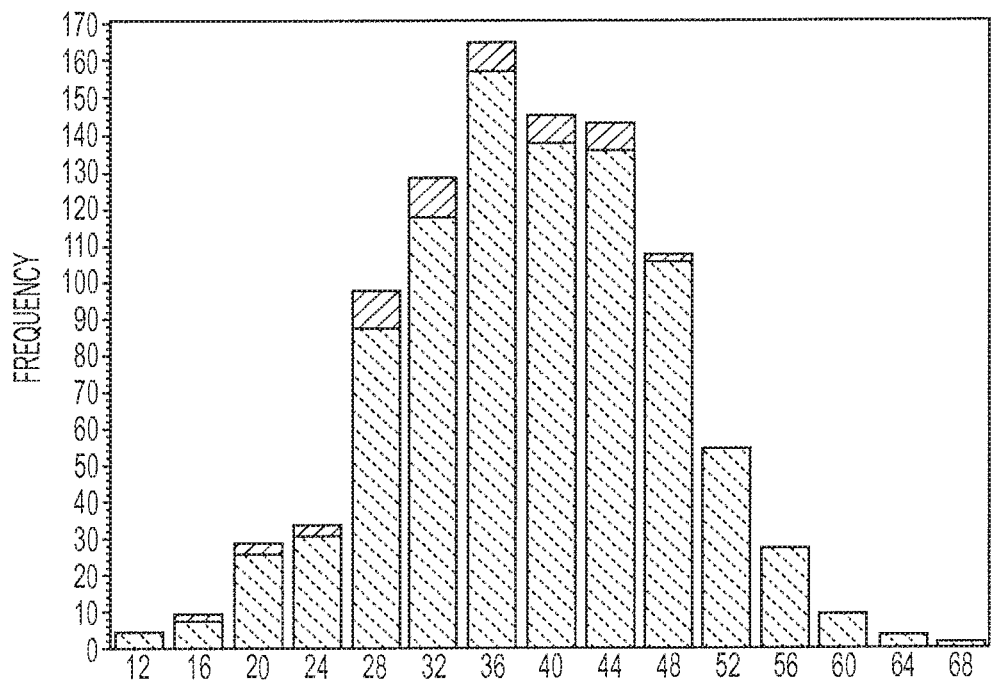
FIG. 20 is a bar graph of percent weight loss showing association of rs17702901 with weight loss in RYGB patients.
Figure 21:
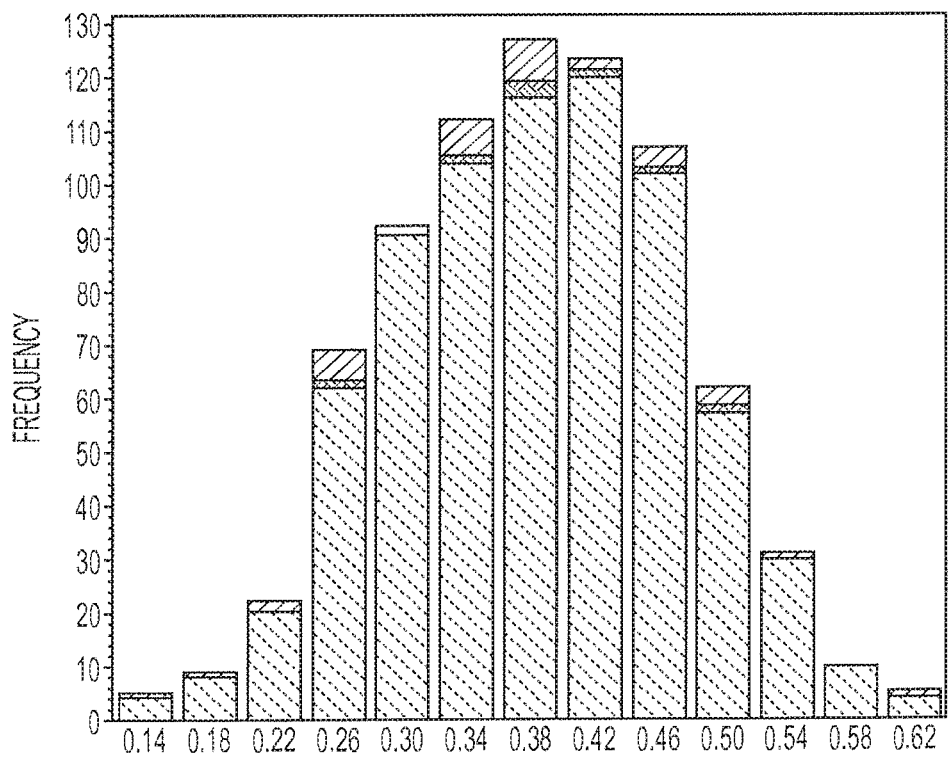
FIG. 21 is a bar graph of percent weight loss showing a lack of an association of validated BMI locus, Melanocortin 4 Receptor (MC4R), with weight loss in RYGB patients.

Because the mechanisms of weight gain and weight loss may be shared, previously reported and validated BMI loci (Speliotes, E. K. et al., *Nat Genet*, vol 42, pp 937-48, 2010)

were analyzed for association with weight loss after surgery. Unlike the association of rs17702901 with weight loss after RYGB (FIG. 20), deep sequencing of the MC4R locus did not indicate any association between variants in this gene and weight loss after surgery (FIG. 21).

Example 8: Different Bariatric Surgeries Act Through Similar Mechanisms

To determine if different metabolic procedures produce similar results, possibly using similar mechanisms of action, patients that have undergone gastric bypass, biliopancreatic diversion, sleeve gastrectomy and duodenal endoluminal sleeve were analyzed for effects of weight loss, food intake, insulin sensitivity, glucose tolerance, insulin secretion, and endogenous glucose production. Despite the disparity in the type of procedure performed, gastric bypass, biliopancreatic diversion, sleeve gastrectomy and duodenal endoluminal sleeve surprisingly had similar effects, increased weight loss, decreased food intake, increased energy expenditure, greater insulin sensitivity, increased glucose tolerance and enhanced insulin secretion. (Data not shown.)

Moreover, the different metabolic procedures also had similar effects on the gastrointestinal endocrine system. Levels of ghrelin, glucagon-like peptide-1, peptide YY and gastric inhibitory polypeptide demonstrated similar changes in post-prandial secretion levels in individuals that have undergone gastric bypass, biliopancreatic diversion, sleeve gastrectomy, ileal interposition or duodenal endoluminal sleeve.

Example 9: Genetic Factors Contributing to Weight Loss

Figure 22:
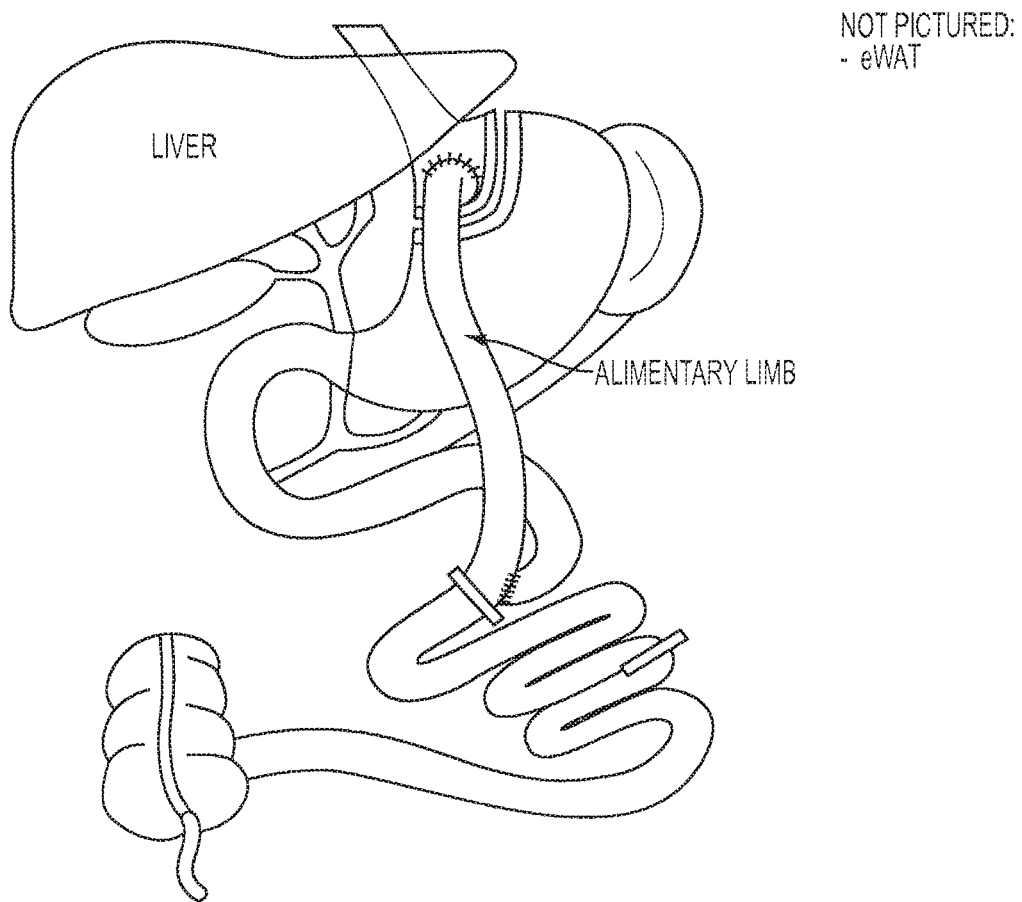
FIG. 22 is a schematic diagram of the anatomy of Roux-en-Y gastric bypass. Tissues noted were dissected from mice 10 weeks after RYGB or sham operation.

The effect of RYGB on expression of genes in a previously described (McAuley, E. Z. et al., Identification Of Sialyltransferase 8B As A Generalized Susceptibility Gene For Psychotic And Mood Disorders On Chromosome 15q25-26, *PLoS ONE* 7, e38172 (2012)) mouse model was determined. Mice were randomized to RYGB or sham operation with food restriction to match the weight of the RYGB animals (WMS). Animals were sacrificed after 10 weeks, and gene expression was measured in the alimentary limb, liver, and epididymal fat (FIG. 22, Table 10).

TABLE 10

Differentially expressed genes.

| SEQ ID NO | Gene Name | Gene Description | ACCESSION_NUMBER |
|---|---|---|---|
| 1 | c1qtnf2 | C1q and tumor necrosis factor related protein 2 | NM_026979 |
| 2 | aqp11 | aquaporin 11 | NM_175105 |
| 3 | aqp11 | aquaporin 11 | AK137326 |
| 4 | sall1 | sal-like 1 | NM_021390 |
| 5 | clasp1 | cytoplasmic linker associated protein 1 | BB190028 |
| 6 | clasp1 | cytoplasmic linker associated protein 1 | NM_001081276 |
| 7 | clasp1 | cytoplasmic linker associated protein 1 | AK006534 |
| 8 | clasp1 | cytoplasmic linker associated protein 1 | AK080782 |
| 9 | clasp1 | cytoplasmic linker associated protein 1 | AW557056 |
| 10 | rps14 | 30S ribosomal protein S14 | NM_020600 |
| 11 | stxbp5 | syntaxin binding protein 5 (tomosyn) | BC038042 |
| 12 | stxbp5 | syntaxin binding protein 5 (tomosyn) | NM_001081344 |
| 13 | stxbp5 | syntaxin binding protein 5 (tomosyn) | BC094582 |
| 14 | stxbp5 | syntaxin binding protein 5 (tomosyn) | AK029982 |
| 15 | st8sia2 | ST8 alpha-N-acetyl-neuraminide alpha-2,8-sialyltransferase 2 | NM_009181 |
| 16 | st8sia2 | ST8 alpha-N-acetyl-neuraminide alpha-2,8-sialyltransferase 2 | BB801232 |
| 17 | ints4 | integrator complex subunit 4 | NM_027256 |
| 18 | phactr1 | phosphatase and actin regulator 1 | NM_198419 |
| 19 | phactr1 | phosphatase and actin regulator 1 | ENSMUST00000095844 |
| 20 | clec4g | | NM_029465 |
| 21 | fbxo15 | F-box protein 15 | NM_015798 |
| 22 | synpo2 | | AK035258 |
| 23 | synpo2 | | ENSMUST00000051443 |
| 24 | synpo2 | | AK004418 |
| 25 | kcnq5 | potassium voltage-gated channel, KQT-like subfamily, member 5 | AK147264 |
| 26 | kcnq5 | potassium voltage-gated channel, KQT-like subfamily, member 5 | NM_023872 |
| 27 | rai14 | retinoic acid induced 14 | NM_030690 |
| 28 | ttf2 | transcription termination factor, RNA polymerase II | BB283807 |
| 29 | hsd17b3 | hydroxysteroid (17-beta) dehydrogenase 3 | NM_008291 |
| 30 | bik | BCL2-interacting killer (apoptosis-inducing) | NM_007546 |
| 31 | cabp5 | | NM_013877 |
| 32 | pax5 | paired box gene 5 | NM_008782 |
| 33 | sstr4 | | ENSMUST00000047292 |
| 34 | cdh11 | cadherin 11, osteoblast | BY359179 |
| 35 | cdh11 | cadherin 11, osteoblast | NM_009866 |
| 36 | slc12a4 | solute carrier family 12 (potassium/chloride transporters), member 4 | NM_009195 |
| 37 | eraf | | NM_133245 |
| 38 | hoxa1 | homeobox A1 | NM_010449 |

TABLE 10-continued

Differentially expressed genes.

| SEQ ID NO | Gene Name | Gene Description | ACCESSION_NUMBER |
|---|---|---|---|
| 39 | satl1 | spermidine/spermine N1-acetyl transferase-like 1 | ENSMUST00000026601 |
| 40 | adipor1 | adiponectin receptor 1 | AK182949 |
| 41 | adipor1 | adiponectin receptor 1 | NM_028320 |
| 42 | adipor1 | adiponectin receptor 1 | AK143680 |
| 43 | abcf2 | ATP-binding cassette, sub-family F (GCN20), member 2 | NM_013853 |
| 44 | abcf2 | ATP-binding cassette, sub-family F (GCN20), member 2 | CA751126 |
| 45 | mier3 | mesoderm induction early response 1, family member 3 | NM_172593 |
| 46 | ddr2 | discoidin domain receptor tyrosine kinase 2 | BB613073 |
| 47 | ddr2 | discoidin domain receptor tyrosine kinase 2 | AK028767 |
| 48 | ddr2 | discoidin domain receptor tyrosine kinase 2 | NM_022563 |
| 49 | nphs1 | nephrosis 1, congenital, Finnish type (nephrin) | AK141081 |
| 50 | zranb3 | zinc finger, RAN-binding domain containing 3 | ENSMUST00000097598 |
| 51 | zranb3 | zinc finger, RAN-binding domain containing 3 | NM_172642 |
| 52 | cldn16 |  | NM_053241 |
| 53 | dhrs3 | dehydrogenase/reductase (SDR family) member 3 | AF061743 |
| 54 | dhrs3 | dehydrogenase/reductase (SDR family) member 3 | NM_011303 |
| 55 | adnp2 | ADNP homeobox 2 | ENSMUST00000066743 |
| 56 | scrt1 |  | NM_130893 |
| 57 | trappc5 | trafficking protein particle complex 5 | NM_025701 |
| 58 | trappc5 | trafficking protein particle complex 5 | AK003633 |
| 59 | polk | polymerase (DNA directed) kappa | ENSMUST00000091386 |
| 60 | polk | polymerase (DNA directed) kappa | NM_012048 |
| 61 | clns1a | chloride channel, nucleotide-sensitive, 1A | NM_023671 |
| 62 | col4a3bp | collagen, type IV, alpha 3 (Goodpasture antigen) binding protein | AK020301 |
| 63 | col4a3bp | collagen, type IV, alpha 3 (Goodpasture antigen) binding protein | NM_023420 |
| 64 | col4a3bp | collagen, type IV, alpha 3 (Goodpasture antigen) binding protein | AK018103 |
| 65 | ckap2 |  | NM_001004140 |
| 66 | spag6 | sperm associated antigen 6 | AK005732 |
| 67 | rps27a | ribosomal protein S27a | NM_001033865 |
| 68 | vps36 | vacuolar protein sorting 36 homolog | AK008946 |
| 69 | vps36 | vacuolar protein sorting 36 homolog | AK156241 |
| 70 | calml4 | calmodulin-like 4 | NM_138304 |
| 71 | thsd1 |  | NM_019576 |
| 72 | thsd1 |  | ENSMUST00000069828 |
| 73 | hmgcr | 3-hydroxy-3-methylglutaryl-CoA reductase | NM_008255 |
| 74 | cln6 | ceroid-lipofuscinosis, neuronal 6, late infantile, variant | NM_001033175 |
| 75 | klk8 |  | NM_008940 |
| 76 | rsf1 | remodeling and spacing factor 1 | AA546468 |
| 77 | rsf1 | remodeling and spacing factor 1 | AK146675 |
| 78 | krt7 |  | NM_033073 |
| 79 | lman2l | lectin, mannose-binding 2-like | NM_001013374 |
| 80 | lman2l | lectin, mannose-binding 2-like | AK031056 |
| 81 | lman2l | lectin, mannose-binding 2-like | AK184498 |
| 82 | lman2l | lectin, mannose-binding 2-like | BY763843 |
| 83 | cnnm4 | cyclin M4 | NM_033570 |
| 84 | cnnm4 | cyclin M4 | ENSMUST00000045383 |
| 85 | gja4 | gap junction protein, alpha 4, 37 kDa | NM_008120 |
| 86 | opalin |  | NM_153520 |
| 87 | opalin |  | AK078150 |
| 88 | klk11 |  | NM_019974 |
| 89 | hoxa4 | homeobox A4 | NM_008265 |
| 90 | retn | retained | ENSMUST00000012849 |
| 91 | klk9 |  | NM_028660 |
| 92 | klk10 |  | NM_133712 |
| 93 | klk12 |  | ENSMUST00000014063 |
| 94 | phf3 | PHD finger protein 3 | BI413552 |
| 95 | phf3 | PHD finger protein 3 | BC099524 |
| 96 | phf3 | PHD finger protein 3 | AK135686 |

TABLE 10-continued

Differentially expressed genes.

| SEQ ID NO | Gene Name | Gene Description | ACCESSION_NUMBER |
|---|---|---|---|
| 97 | phf3 | PHD finger protein 3 | AK122230 |
| 98 | grpel1 | GrpE-like 1, mitochondrial | NM_024478 |
| 99 | grpel1 | GrpE-like 1, mitochondrial | AK212713 |
| 100 | grpel1 | GrpE-like 1, mitochondrial | AK212713 |
| 101 | hoxa5 | homeobox A5 | NM_010453 |
| 102 | pacrg | PARK2 co-regulated | NM_027032 |
| 103 | akap8 | A kinase (PRKA) anchor protein 8 | NM_019774 |
| 104 | akap8 | A kinase (PRKA) anchor protein 8 | ENSMUST00000002699 |
| 105 | med21 | mediator complex subunit 21 | NM_025315 |
| 106 | ap1m2 | adaptor-related protein complex 1, mu 2 subunit | NM_009678 |
| 107 | ulk4 | unc-51-like kinase 4 | NM_177589 |
| 108 | ulk4 | unc-51-like kinase 4 | ENSMUST00000098284 |
| 109 | ulk4 | unc-51-like kinase 4 | BU946109 |
| 110 | ift57 | intraflagellar transport protein 57 | NM_028680 |
| 111 | ift57 | intraflagellar transport protein 57 | AK014731 |
| 112 | lca5l | | NM_001001492 |
| 113 | armc9 | armadillo repeat containing 9 | NM_030184 |
| 114 | armc9 | armadillo repeat containing 9 | NM_027456 |
| 115 | armc9 | armadillo repeat containing 9 | AK019600 |
| 116 | dio3 | deiodinase, iodothyronine, type III | NM_172119 |
| 117 | wfdc8 | | NM_001080550 |
| 118 | cfb | complement factor B | NM_008198 |
| 119 | eif4e | eukaryotic translation initiation factor 4e | NM_007917 |
| 120 | eif4e | eukaryotic translation initiation factor 4e | M61731 |
| 121 | eif4e | eukaryotic translation initiation factor 4e | AK146757 |
| 122 | igj | immunoglobulin J polypeptide, linker protein for immunoglobulin alpha and mu polypeptides | NM_152839 |
| 123 | ctnnd2 | catenin (cadherin-associated protein), delta 2 (neural plakophilin-related arm-repeat protein) | ENSMUST00000081728 |
| 124 | ampd2 | adenosine monophosphate deaminase 2 (isoform L) | NM_028779 |
| 125 | rtkn | rhotekin | NM_009106 |
| 126 | rsl1d1 | ribosomal L1 domain containing 1 | NM_025546 |
| 127 | elk4 | ELK4, ETS-domain protein | AK156537 |
| 128 | elk4 | ELK4, ETS-domain protein | ENSMUST00000086556 |

To identify genetic factors contributing to weight loss after RYGB, an exploratory genome wide association study (GWAS) of 858 genetically unrelated individuals was performed (Table 2). After stringent quality control measures, 1,943,373 single nucleotide polymorphisms (SNPs) were analyzed. To minimize heterogeneity from the underlying population structure, we limited the analyses to 693 patients genetically determined to be Caucasian. The association between SNPs and percent total weight loss (% WL) at the lowest weight (nadir) after RYGB using additive models of quantitative trait associations was assessed.

TABLE 11

Pre- and post-operative characteristics of the RYGB study population and replication cohort.

| | Original Cohort | Replication Cohort | p-value |
|---|---|---|---|
| Age (years; ±SD) | 45.8 ± 11.2 | 47.1 ± 11.1 | 0.07 |
| Preoperative BMI (mean kg/m²; ±SD) | 50.3 ± 8.4 | 48.1 ± 8.5 | 0.0002 |
| Sex (% female) | 73.2 | 71.7 | 0.65 |
| Diabetes (%) | 40.2 | 41.5 | 0.19 |
| BMI at weight nadir (mean kg/m²; ±SD) | 30.6 ± 6.4 | 29.9 ± 6.0 | 0.32 |
| % WL at nadir (%; ±SD) | 39.0 ± 9.1 | 37.5 | 0.01 |

103 marginally significant ($P<5\times10^{-5}$) SNPs were identified (Table 12), representing 26 independent loci (pairwise $r^2<0.5$). The most highly associated SNP per region was carried forward for validation in an independent cohort of 327 Caucasian RYGB patients. 23 of the SNPs were successfully genotyped, and associations with percent weight loss were analyzed using linear regression models. Results of the original and validation cohorts were then meta-analyzed using fixed effects models.

TABLE 12

Top 50 expression transcripts associated with rs17702901.

| Gene | P-value | Tissue |
|---|---|---|
| AK093355 | 1.72664E-05 | liver |
| hCT1814610 | 1.84938E-05 | liver |
| CABP5 | 3.39269E-05 | liver |
| HSS00373574 | 3.99297E-05 | liver |
| PAX5 | 4.16901E-05 | liver |
| hCT2261424 | 4.18181E-05 | subcutaneous fat |
| hCT32381 | 4.7966E-05 | subcutaneous fat |
| SSTR4 | 6.26125E-05 | liver |
| AK096731 | 7.36552E-05 | liver |
| CDH11 | 9.30141E-05 | liver |
| HSS00051247 | 0.000109662 | liver |
| SLC12A4 | 0.000119327 | liver |
| Contig34964 | 0.000125475 | liver |
| BC009871 | 0.000139822 | liver |
| hCT1646793 | 0.000169095 | liver |
| HSS00381099 | 0.000178477 | liver |
| FAM10A4 | 0.000193237 | subcutaneous fat |
| Contig12033 | 0.000200709 | omental fat |
| CNTNAP3B | 0.000212491 | omental fat |
| AK094533 | 0.00022344 | liver |

TABLE 12-continued

Top 50 expression transcripts associated with rs17702901.

| Gene | P-value | Tissue |
|---|---|---|
| ERAF | 0.000249779 | omental fat |
| HOXA1 | 0.000251027 | liver |
| SATL1 | 0.000251598 | subcutaneous fat |
| U84510 | 0.000259264 | liver |
| ADIPOR1 | 0.000260775 | liver |
| ABCF2 | 0.000289326 | liver |
| hCT1958096 | 0.000291375 | liver |
| MIER3 | 0.000305798 | liver |
| DDR2 | 0.000308075 | liver |
| NPHS1 | 0.000315369 | liver |
| HSS00053942 | 0.000327271 | liver |
| ZRANB3 | 0.000339101 | subcutaneous fat |
| CLDN16 | 0.000362854 | liver |
| DHRS3 | 0.000398518 | liver |

SNP rs17702901 at 15q26.1 was significantly associated with percent weight loss after Roux-en-Y gastric bypass (RYGB) ($P_{replication}$=0.002; $P_{meta-analyzed}$=7.4×10$^{-8}$). To determine the potential biological function of rs17702901, its association with the expression level of ~44,000 transcripts in liver, omental fat and subcutaneous fat was examined. No multiple test-corrected, significant associations were detected between rs17702901 and preoperative expression of any transcripts, including the two nearest genes—ST8SIA2, located ~6.7 kilobases (kb) downstream of rs17702901 and SLCO3A1, ~223 kb upstream of this SNP (Table 12). The magnitude of effect was similar in the study population and replication cohorts, with betas of −6.70 and −6.52, respectively (Table 13).

TABLE 13

SNP association results from the genome-wide association analysis.

| SNP | Closest Gene | Distance from Gene to SNP (bp)[1] | MA[2] | Chr | Position | GWAS Cohort Beta | P-value | Replication Cohort Beta | P-value | Combined Beta | P-value |
|---|---|---|---|---|---|---|---|---|---|---|---|
| rs10515808 | C1QTNF2 | 23283 | A | 5 | 159753509 | −4.06 | 8.2 × 10$^{-8}$ | −1.17 | 0.27 | −3.08 | 4.2 × 10$^{-7}$ |
| rs7158359 | CHES1 | 28219 | G | 14 | 88664048 | −3.03 | 3.4 × 10$^{-7}$ | −0.41 | 0.65 | −2.27 | 4.6 × 10$^{-6}$ |
| rs7129556 | AQP11 | 631 | T | 11 | 76977696 | −2.80 | 4.3 × 10$^{-7}$ | −0.60 | 0.44 | −2.07 | 3.9 × 10$^{-6}$ |
| rs7185923 | SALL1 | 60335 | C | 16 | 49802988 | −2.40 | 8.1 × 10$^{-7}$ | −0.63 | 0.40 | −1.89 | 3.5 × 10$^{-6}$ |
| rs934760 | CLASP1 | 0 | G | 2 | 12202672 | −4.28 | 4.6 × 10$^{-6}$ | 0.56 | 0.68 | — | — |
| rs1104959 | RPS14 | 79991 | T | 5 | 149722429 | 7.75 | 5.8 × 10$^{-6}$ | 0.86 | 0.66 | 4.79 | 1.8 × 10$^{-4}$ |
| rs9403832 | STXBP5 | 0 | C | 6 | 14795969 | 2.17 | 9.8 × 10$^{-6}$ | −0.51 | 0.47 | 1.30 | 0.001 |
| rs17702901 | ST8SIA2 | 6728 | A | 15 | 90731415 | −6.70 | 1.1 × 10$^{-5}$ | −6.52 | 0.002 | −6.64 | 7.4 × 10$^{-8}$ |
| rs588217 | INTS4 | 6391 | A | 11 | 77261024 | −2.55 | 1.4 × 10$^{-5}$ | −0.59 | 0.47 | −1.87 | 7.0 × 10$^{-5}$ |
| rs6554217 | RNU5B | 63795 | T | 4 | 55672161 | 2.89 | 1.5 × 10$^{-5}$ | −1.43 | 0.15 | — | — |
| rs9357419 | PHACTR1 | 134845 | C | 6 | 12690973 | −2.95 | 1.8 × 10$^{-5}$ | 0.56 | 0.56 | −1.80 | 0.001 |
| rs11260025 | CLEC4G | 12090 | C | 19 | 7687753 | 3.33 | 2.2 × 10$^{-5}$ | −1.06 | 0.32 | 1.82 | 0.004 |
| rs12803675 | OR4C13 | 71848 | A | 11 | 49858702 | 3.69 | 2.7 × 10$^{-5}$ | 0.37 | 0.79 | 2.80 | 1.8 × 10$^{-4}$ |
| rs13380914 | FBXO15 | 578813 | A | 18 | 69312767 | −2.50 | 2.9 × 10$^{-5}$ | −0.57 | 0.51 | 1.89 | 1.2 × 10$^{-4}$ |
| rs10518316 | SYNPO2 | 0 | G | 4 | 120241167 | −2.52 | 3.0 × 10$^{-5}$ | 1.37 | 0.15 | — | — |
| rs6911409 | KCNQ5 | 0 | A | 6 | 73910091 | −3.71 | 3.5 × 10$^{-5}$ | −1.14 | 0.32 | −2.74 | 9.7 × 10$^{-5}$ |
| rs12659689 | RAI14 | 0 | C | 5 | 34836108 | −1.98 | 3.9 × 10$^{-5}$ | −0.11 | 0.87 | −1.39 | 4.6 × 10$^{-4}$ |
| rs1952291 | C14orf106 | 618149 | A | 14 | 45410504 | −4.32 | 4.3 × 10$^{-5}$ | 1.27 | 0.42 | −2.65 | 0.003 |
| rs1289666 | TTF2 | 0 | C | 1 | 117350312 | 2.73 | 4.3 × 10$^{-5}$ | −0.24 | 0.80 | — | — |
| rs11788785 | HSD17B3 | 0 | A | 9 | 96110183 | −2.79 | 4.5 × 10$^{-5}$ | −0.68 | 0.50 | — | — |
| rs1883264 | BIK | 0 | C | 22 | 41834344 | 2.85 | 4.6 × 10$^{-5}$ | 0.76 | 0.46 | — | — |
| rs12696123 | MIRN135A2 | 66339 | C | 3 | 163099074 | −2.36 | 4.7 × 10$^{-5}$ | 0.24 | 0.77 | — | — |

[1]Absolute value of the distance from the start or stop site of the closest gene. A distance of 0 indicates that the SNP is located within the gene.
[2]MA = Minor allele TABLE 12-continued Top 50 expression transcripts associated with rs17702901.

| Gene | P-value | Tissue |
|---|---|---|
| OR2A2 | 0.000430517 | liver |
| BC022568 | 0.000463747 | liver |
| Contig34719 | 0.000468504 | liver |
| hCT1845647 | 0.000470327 | liver |
| ADNP2 | 0.000470332 | liver |
| hCT2297022 | 0.000487732 | liver |
| HSS00299143 | 0.000491702 | liver |
| AF400502 | 0.000519205 | omental fat |
| SCRT1 | 0.000521866 | liver |
| Contig43708 | 0.000537265 | liver |
| HSS00214508 | 0.000540097 | subcutaneous fat |
| C2orf29 | 0.000543099 | liver |
| hCT1956088 | 0.000566656 | liver |
| Contig57822 | 0.000581398 | subcutaneous fat |
| hCT1641204 | 0.000589909 | liver |
| CR749513 | 0.000590453 | liver |

Figure 23A:
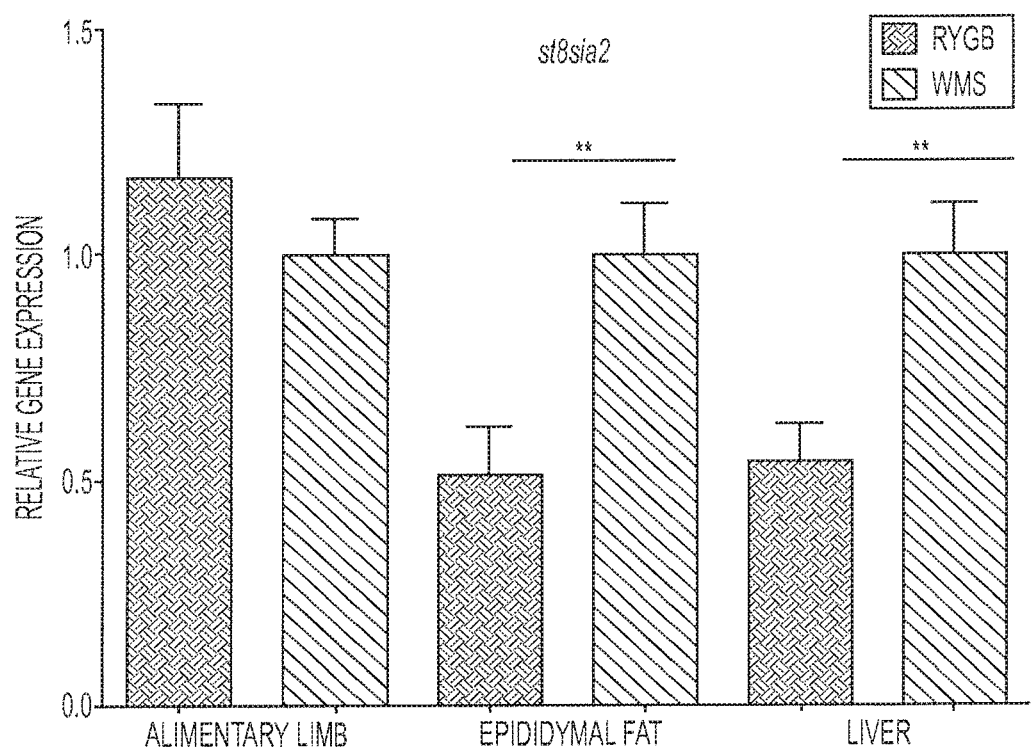
FIG. 23A is a bar graph showing the comparative expression of st8sia2 in RYGB-treated and sham operated, weight matched mice (WMS). Grey bars denote the WMS group, blue bars the RYGB group. Error bars denote the standard error of the mean. *$p<0.05$, $p<0.01$, *$p<0.001$.
Figure 23B:
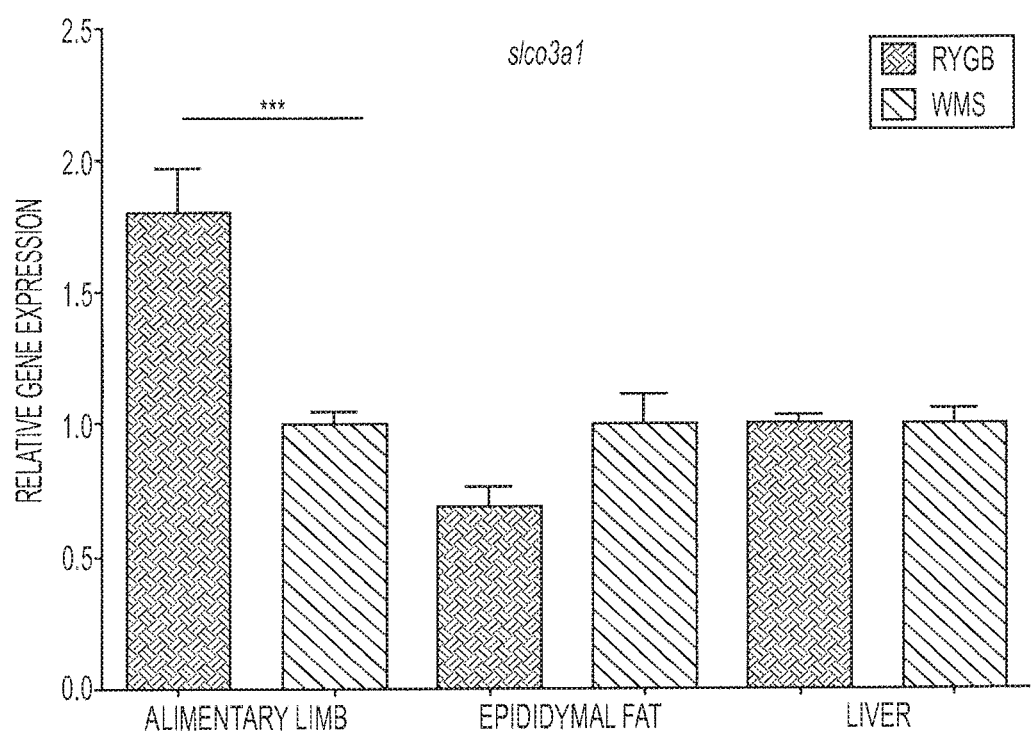
FIG. 23B is a bar graph showing the comparative expression of slco3a1 in RYGB-treated and sham operated, weight matched mice (WMS). Grey bars denote the WMS group, blue bars the RYGB group. Error bars denote the standard error of the mean. *$p<0.05$, $p<0.01$, *$p<0.001$.

Expression of sta8sia2, the mouse orthologue of the gene closest to rs17702901, was significantly lower in the epididymal fat and liver of RYGB-treated than WMS mice (FIG. 23A). In addition, intestinal alimentary limb expression of slco3a1 was significantly greater in the RYGB group than WMS controls (FIG. 23B).

Figure 24A:
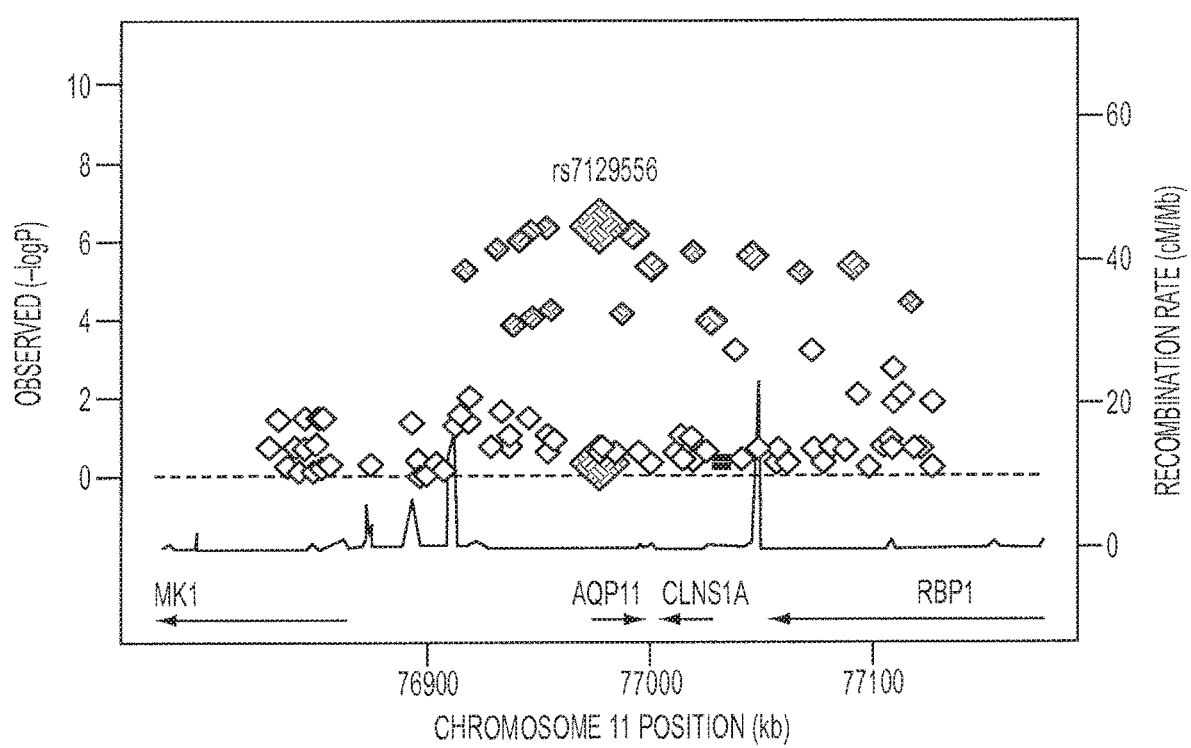
FIG. 24A is a regional association plot showing the AQP11 locus. Each SNP is plotted as a diamond based on its chromosomal location (x-axis) and $-\log_{10}$ P value (left y-axis). Recombination rates are plotted in grey toward the bottom of the graph (right y-axis). The large upper diamond represents the top SNP in the region (rs7129556) from the genome-wide association study (GWAS), and the large lower diamond represents the p-value from that SNP in the replication cohort.

Results in humans using a gene-based association test that integrates SNP associations with linkage disequilibrium patterns within each gene was analyzed and identified a marginally significant association (p=8.0×10$^{-7}$) for the aquaporin 11 gene (AQP11; Table 14). While there were 27 SNPs in this region with a P-value<0.001, there was no statistically significant association between the top SNP in this region, rs7129556, and percent weight loss in the replication cohort (FIG. 24A). No genome-wide, multiple test-corrected, significant associations between rs7129556 and the expression of any transcripts in humans was detected, but this SNP was marginally associated with expression of AQP11 itself ($P_{omental}$=9.7×10$^{-5}$, $P_{liver}$=1.6× 10$^{-4}$; Table 15).

Figure 24C:
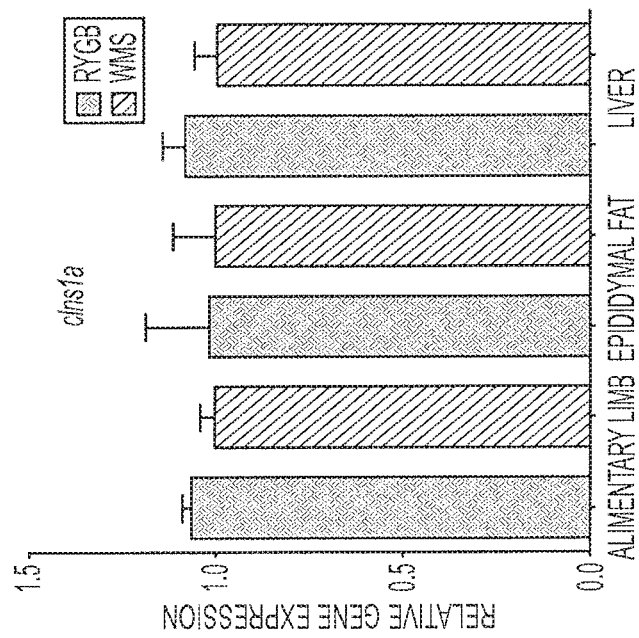
FIG. 24C is a bar graph showing the relative expression level of clns1a. Light bars denote the WMS group, dark bars the RYGB group. Error bars denote the standard error of the mean *$p<0.05$, $p<0.01$, *$p<0.001$.
Figure 24B:
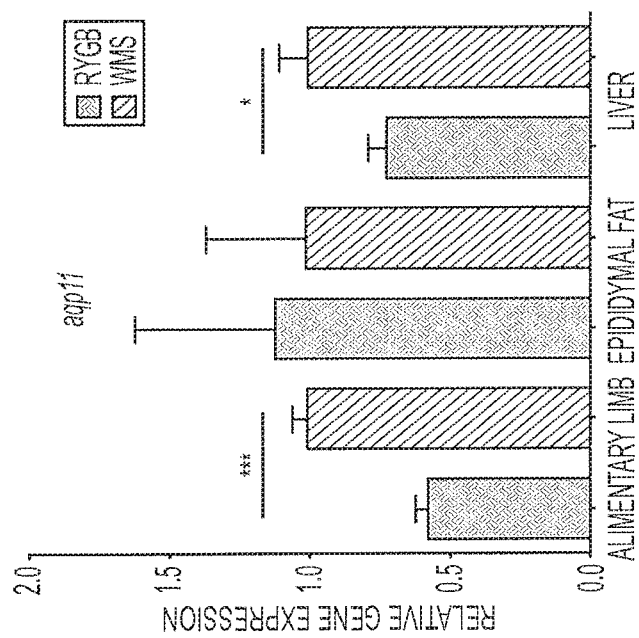
FIG. 24B is a bar graph showing the relative expression level of aqp11. Light bars denote the WMS group, dark bars the RYGB group. Error bars denote the standard error of the mean. *$p<0.05$, $p<0.01$, *$p<0.001$.

In the mouse models, aqp11 expression in the alimentary limb and liver was significantly lower after RYGB than in WMS mice (FIG. 24B). In contrast, expression of clns1a, the gene closest to aqp11, was not significantly changed after RYGB (FIG. 24C).

TABLE 14

Top 50 association results for gene-based association tests.

| Gene | Chromosome | Number of SNPs in group | Gene-based P-value | Top SNP in region | Top SNP P-value |
|---|---|---|---|---|---|
| AQP11 | 11 | 36 | 0.000008 | rs7129556 | 4.276E-07 |
| TRAPPC5 | 19 | 33 | 0.000105 | rs11260025 | 2.21E-05 |
| FCER2 | 19 | 36 | 0.000118 | rs11260025 | 2.21E-05 |
| C11orf67 | 11 | 68 | 0.000168 | rs588217 | 1.363E-05 |
| C19orf59 | 19 | 38 | 0.000187 | rs11260025 | 2.21E-05 |
| CD209 | 19 | 52 | 0.000384 | rs11260025 | 2.21E-05 |
| CLEC4G | 19 | 52 | 0.000421 | rs11260025 | 2.21E-05 |
| AP3S1 | 5 | 81 | 0.00056 | rs7722770 | 0.0008396 |
| CLASP1 | 2 | 206 | 0.000568 | rs934760 | 4.595E-06 |
| POLK | 5 | 82 | 0.0007 | rs10942739 | 0.0001566 |
| CLEC4M | 19 | 46 | 0.00071 | rs11260025 | 2.21E-05 |
| CLNS1A | 11 | 39 | 0.000747 | rs7129556 | 4.276E-07 |
| COL4A3BP | 5 | 82 | 0.000873 | rs6453134 | 0.0001267 |
| GCNT4 | 5 | 61 | 0.001 | rs4632781 | 0.0002618 |
| INTS4 | 11 | 115 | 0.00102 | rs588217 | 1.363E-05 |
| CKAP2 | 13 | 26 | 0.001241 | rs11618716 | 0.0007868 |
| SPAG6 | 10 | 4 | 0.001533 | rs9665348 | 0.03949 |
| C3orf39 | 3 | 86 | 0.00167 | rs536119 | 6.329E-05 |
| RPS27A | 2 | 56 | 0.001706 | rs1561231 | 0.0009679 |
| C1orf87 | 1 | 165 | 0.001751 | rs686119 | 0.0004618 |
| VPS36 | 13 | 46 | 0.00176 | rs4884452 | 0.0003805 |
| CALML4 | 15 | 41 | 0.00197 | rs8025947 | 0.0005017 |
| THSD1 | 13 | 43 | 0.002 | rs4884452 | 0.0003805 |
| TBC1D3B | 17 | 2 | 0.00204 | rs4500794 | 0.0004894 |
| HMGCR | 5 | 66 | 0.00214 | rs7700468 | 0.000152 |
| CLN6 | 15 | 43 | 0.00219 | rs8025947 | 0.0005017 |
| KLK8 | 19 | 81 | 0.00223 | rs1701948 | 0.0005329 |
| RSF1 | 11 | 104 | 0.002362 | rs11237249 | 1.906E-06 |
| KRT7 | 12 | 121 | 0.002513 | rs7953684 | 0.0001044 |
| ZNF223 | 19 | 80 | 0.00261 | rs8105003 | 0.0003053 |
| LMAN2L | 2 | 25 | 0.00276 | rs2872633 | 0.001663 |
| LVRN | 5 | 243 | 0.00276 | rs1593872 | 0.0003657 |
| CNNM4 | 2 | 34 | 0.0028 | rs17119562 | 0.003587 |
| SLCO6A1 | 5 | 157 | 0.002973 | rs10041015 | 0.0006075 |
| GJA4 | 1 | 28 | 0.00298 | rs4653105 | 0.001588 |
| OPALIN | 10 | 135 | 0.00298 | rs11188734 | 0.0001968 |
| KLK11 | 19 | 104 | 0.00301 | rs1701948 | 0.0005329 |
| HOXA4 | 7 | 60 | 0.00304 | rs983184 | 0.0005409 |
| RETN | 19 | 33 | 0.00305 | rs11260025 | 2.21E-05 |
| KLK9 | 19 | 84 | 0.00307 | rs1701948 | 0.0005329 |
| ZNF284 | 19 | 74 | 0.003167 | rs8105003 | 0.0003053 |
| KRT81 | 12 | 150 | 0.00317 | rs7953684 | 0.0001044 |
| SIRPG | 20 | 123 | 0.00318 | rs4254565 | 0.0006302 |
| KLK10 | 19 | 95 | 0.00323 | rs1701948 | 0.0005329 |
| C1orf212 | 1 | 46 | 0.00329 | rs4653105 | 0.001588 |
| KLK12 | 19 | 110 | 0.00334 | rs1701948 | 0.0005329 |
| PHF3 | 6 | 53 | 0.00334 | rs4710437 | 0.0001252 |
| GRPEL1 | 4 | 74 | 0.00338 | rs12648134 | 0.0005674 |
| HOXA5 | 7 | 58 | 0.00349 | rs983184 | 0.0005409 |

TABLE 15

Top 50 expression transcripts associated with rs17702901.

| Gene | P-value | Tissue |
|---|---|---|
| HSS00247867 | 1.09413E-05 | liver |
| AL137575 | 3.05555E-05 | subcutaneous fat |
| hCT1660004_2 | 5.80012E-05 | liver |
| PACRG | 6.10809E-05 | omental fat |
| AF086224 | 7.56724E-05 | subcutaneous fat |
| AQP11 | 9.69686E-05 | omental fat |
| HSS00134080 | 0.000126719 | subcutaneous fat |
| AKAP8 | 0.000144471 | liver |

TABLE 15-continued

Top 50 expression transcripts associated with rs17702901.

| Gene | P-value | Tissue |
|---|---|---|
| AQP11 | 0.000155285 | liver |
| MED21 | 0.000197981 | liver |
| AP1M2 | 0.000198556 | subcutaneous fat |
| ULK4 | 0.000234395 | liver |
| Contig36748_RC | 0.000248422 | omental fat |
| ZNF711 | 0.000258753 | omental fat |
| IFT57 | 0.000266345 | liver |
| IGLV2_14 | 0.000267441 | subcutaneous fat |
| LCA5L | 0.000271869 | liver |
| ADAM3A | 0.000276415 | liver |
| AL833696 | 0.000303924 | liver |
| ARMC9 | 0.000311108 | omental fat |
| BC040305 | 0.000315233 | liver |
| DIO3 | 0.000324871 | liver |
| WFDC8 | 0.000338595 | omental fat |
| CFB | 0.000339373 | subcutaneous fat |
| EIF4E | 0.000381093 | liver |
| IGJ | 0.000381533 | liver |
| ZNF509 | 0.000394645 | liver |
| PI4KAP2 | 0.000415647 | liver |
| CTNND2 | 0.00042246 | subcutaneous fat |
| C3orf38 | 0.000423274 | liver |
| AMPD2 | 0.000424693 | liver |
| XM_173060 | 0.000429279 | liver |
| XM_065192 | 0.00045425 | omental fat |
| RTKN | 0.000455737 | liver |
| Contig41220_RC | 0.000481428 | omen |
| RSL1D1 | 0.00048159 | subq |
| AK097908 | 0.000496614 | omental fat |
| XM_210217 | 0.000505951 | liver |
| HSS00095153 | 0.000506833 | subq |
| Contig45100_RC | 0.000518199 | liver |
| AK074192 | 0.000560538 | omental fat |
| CFB | 0.000563012 | subq |
| hCT1955907_1 | 0.000617333 | liver |
| XM_173120 | 0.000620047 | liver |
| AK022383 | 0.000638859 | omental fat |
| AL833662 | 0.000639129 | omental fat |
| Contig15012_RC | 0.000641473 | omental fat |
| Contig31661_RC | 0.000646011 | subcutaneous fat |
| PEA15 | 0.000647577 | subcutaneous fat |
| ELK4 | 0.000650268 | liver |

Because the physiological mechanisms of weight gain to generate obesity and weight loss after RYGB may be related, previously reported and validated BMI-associated loci were assessed for association with weight loss after RYGB in humans. None of the 32 previously-reported BMI-associated or 28 diabetes-associated loci was associated with weight loss after surgery (Tables 16 and 17). Deep sequencing of the MC4R locus showed no evidence of an association between variants in this gene and weight loss after RYGB.

TABLE 16

Association results for SNPs previously identified as associated with obesity.

| SNP | Closest Genes | Chr | Position | GWAS Cohort Beta | GWAS Cohort P-value | Validation Cohort Beta | Validation Cohort P-value | Combined Beta | Combined P-value |
|---|---|---|---|---|---|---|---|---|---|
| rs3810291 | TMEM160, ZC3H4 | 19 | 52260843 | 0.8816 | 0.09116 | 1.627 | 0.03188 | 1.1222 | 0.008874 |
| rs9816226 | ETV5 | 3 | 187317193 | 1.18 | 0.08907 | 0.04788 | 0.9598 | | |
| rs713586 | RBJ, ADCY3, POMC | 2 | 25011512 | 0.2023 | 0.678 | 1.117 | 0.1079 | | |
| rs206936 | NUDT3, HMGA1 | 6 | 34410847 | 0.8864 | 0.1432 | −1.133 | 0.1898 | 0.2204 | 0.6562 |
| rs12444979 | GPRC5B, IQCK | 16 | 19841101 | 0.4432 | 0.5179 | 0.1076 | 0.9165 | 0.3396 | 0.551 |
| rs3817334 | MTCH2, NDUFS3, CUGBP1 | 11 | 47607569 | 0.7219 | 0.1428 | 0.2568 | 0.7194 | 0.5722 | 0.1579 |
| rs2890652 | LRP1B | 2 | 142676401 | | | 1.07 | 0.2291 | | |
| rs4929949 | RPL27A, TUB | 11 | 8561169 | | | −1.146 | 0.1109 | | |
| rs2112347 | FLJ35779, HMGCR | 5 | 75050998 | −0.252 | 0.6206 | −1.337 | 0.08203 | 0.5839 | 0.1684 |
| rs1558902 | FTO | 16 | 52361075 | −0.1002 | 0.8373 | 0.7299 | 0.322 | | |
| rs7359397 | SH2B1, APOB48R, SULT1A2, AC138894.2, ATXN2L, TUFM | 16 | 28793160 | | | −0.3648 | 0.6172 | | |
| rs1555543 | PTBP2 | 1 | 96717385 | −0.1002 | 0.8373 | 0.7299 | 0.322 | | |
| rs10767664 | BDNF | 11 | 27682562 | −0.6604 | 0.2437 | −3.103 | 0.08731 | 0.8798 | 0.1033 |
| rs29941 | KCTD15 | 1 | 39001372 | | | | | | |
| rs10968576 | LRRN6C | 9 | 28404339 | −0.2771 | 0.6109 | 0.9994 | 0.1874 | 0.1585 | 0.7198 |
| rs2287019 | QPCTL, GIPR | 19 | 50894012 | −0.2966 | 0.6254 | 0.3084 | 0.7506 | 0.1261 | 0.8064 |
| rs4836133 | ZNF608 | 5 | 124360002 | 0.1233 | 0.8095 | 0.272 | 0.6757 | | |
| rs2867125 | TMEM18 | 2 | 612827 | 1.131 | 0.09057 | 1.074 | 0.2894 | 1.1137 | 0.04559 |
| rs2241423 | MAP2K5, LBXCOR1 | 15 | 65873892 | 0.8342 | 0.1576 | −0.6305 | 0.4646 | 0.3667 | 0.451 |
| rs11847697 | PRKD1 | 14 | 29584863 | 1.22 | 0.3201 | 5.553 | 0.002041 | 2.6094 | 0.009877 |
| rs4771122 | MTIF, GTF3A | 13 | 26918180 | −0.05777 | 0.9246 | 2.139 | 0.02102 | 0.6115 | 0.2295 |
| rs10150332 | NRXN3 | 14 | 79006717 | −0.7973 | 0.1883 | 0.3959 | 0.6395 | 0.3922 | 0.4254 |
| rs13078807 | CADM2 | 3 | 85966840 | −0.4147 | 0.4005 | −0.2349 | 0.7358 | | |
| rs1514175 | TNNI3K | 1 | 74764232 | −0.4147 | 0.4005 | −0.2349 | 0.7358 | | |
| rs7138803 | FAIM2 | 12 | 48533735 | −0.1494 | 0.7614 | −1.144 | 0.1332 | 0.4429 | 0.2834 |
| rs10938397 | GNPDA2 | 4 | 44877284 | 0.484 | 0.325 | 2.172 | 0.2447 | | |
| rs571312 | MC4R | 18 | 55990749 | −0.3649 | 0.5281 | −0.1409 | 0.8599 | 0.2878 | 0.5387 |
| rs887912 | FANCL | 2 | 59156381 | | | −0.9561 | 0.2035 | | |
| rs13107325 | SLC39A8 | 4 | 103407732 | | | −1.233 | 0.3084 | | |
| rs543874 | SEC16B | 1 | 176156103 | 0.4599 | 0.444 | 0.453 | 0.5792 | | |
| rs987237 | TFAP2B | 6 | 50911009 | −0.1616 | 0.7928 | 1.557 | 0.07323 | 0.4139 | 0.4091 |
| rs2815752 | NEGR1 | 1 | 72585028 | −0.1446 | 0.7788 | −1.347 | 0.06805 | | |

TABLE 17

Association results for SNPs previously identified as associated with diabetes.

| SNP | Closest Genes | Chr | Position | GWAS Cohort Beta | GWAS Cohort P-value |
|---|---|---|---|---|---|
| rs10923931 | NOTCH2 | 1 | 120319482 | −1.509 | 0.0665 |
| rs780094 | GCKR | 2 | 27594741 | 0.364 | 0.4625 |
| rs7578597 | THADA | 2 | 43586327 | −0.7071 | 0.3725 |
| rs7593730 | RBMS1 | 2 | 160879700 | −0.3977 | 0.4931 |
| rs1801282 | PPARG | 3 | 12368125 | | |
| rs4607103 | ADAMTS9 | 3 | 64686944 | 0.2305 | 0.6702 |
| rs1470579 | IGF2BP2 | 3 | 187011774 | 0.4983 | 0.341 |
| rs10010131 | WFS1 | 4 | 6343816 | 0.4312 | 0.3969 |
| rs7754840 | CDKAL1 | 6 | 20769229 | 0.1054 | 0.843 |
| rs10244051 | DGKB-TMEM195 | 7 | 15030358 | 0.03538 | 0.9417 |
| rs864745 | JAZF1 | 7 | 28147081 | −0.2841 | 0.5611 |
| rs4607517 | GCK | 7 | 44202193 | −1.337 | 0.03861 |
| rs13266634 | SLC30A8 | 8 | 118253964 | 0.04158 | 0.9395 |
| rs10811661 | CDKN2A/B | 9 | 22124094 | | |
| rs12779790 | CDC123/CAMK1D | 10 | 12368016 | 1.256 | 0.04326 |
| rs5015480 | HHEX/IDE | 10 | 94455539 | −0.5655 | 0.2477 |
| rs7903146 | TCF7L2 | 10 | 114748339 | −0.05057 | 0.9243 |
| rs163184 | KCNQ1 | 11 | 2803645 | −0.7157 | 0.1421 |
| rs2237892 | KCNQ1 | 11 | 2796327 | 2.437 | 0.01667 |
| rs231362 | KCNQ1 | 11 | 2648047 | 0.169 | 0.7283 |
| rs5215 | KCNJ11 | 11 | 17365206 | −0.2529 | 0.6285 |
| rs1552224 | CENTD2 region | 11 | 72110746 | | |
| rs10830963 | MTNR1B | 11 | 92348358 | 0.9426 | 0.2734 |
| rs2943634 | IRS1 region | 11 | 226776324 | −0.291 | 0.5857 |
| rs7961581 | TSPAN8/LGR5 | 12 | 69949369 | −0.1602 | 0.7799 |
| rs7957197 | HNF1A | 12 | 119945069 | −0.2222 | 0.7284 |
| rs11642841 | FTO | 16 | 52402988 | −0.5849 | 0.2549 |
| rs4430796 | HNF1B | 17 | 33172153 | 0.1217 | 0.8362 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11236392B2). An electronic copy of the "Sequence Listing" will also be available from the USPTO upon request and payment of the fee set forth in 37 CFR 1.19(b)(3).

The invention claimed is:

1. A method of treating a human subject having a metabolic disorder, the method comprising:
   (a) obtaining a biological sample from the subject;
   (b) assaying the sample to detect for the presence of an A nucleotide or a G nucleotide at single nucleotide polymorphism (SNP) rs17702901 (SEQ ID NO: 829);
   (c) based on the assaying step, determining that the subject has a GG genotype at rs17702901; and
   (d) performing a Roux-en-Y gastric bypass (RYGB) procedure on the subject determined to have the GG genotype at rs17702901.

2. A method of treating a weight-related disorder in a subject comprising:
   (a) obtaining a sample comprising nucleic acids from the subject;
   (b) assaying the sample to detect the presence of an A nucleotide or a G nucleotide at single nucleotide polymorphism (SNP) rs17702901 (SEQ ID NO: 829);
   (c) based on the assaying step, determining that the subject has a GG genotype at rs17702901; and
   (d) performing a Roux-en-Y gastric bypass (RYGB) procedure on the subject determined to have GG genotype at rs17702901.

3. The method of claim 2, wherein the nucleic acids are deoxyribonucleic acids (DNA).

4. The method of claim 2, further comprising obtaining a clinical measurement in the subject prior to step (d).

5. The method of claim 4, wherein the clinical measurement is at least one of a pre-operative body mass index (BMI), a glucose tolerance, bile acid profile, and body composition/fat distribution of the subject.

6. The method of claim 5, wherein the clinical measurement is the BMI of the subject.

7. The method of claim 6, wherein the pre-operative BMI of the subject is greater than 23 kg/m$^2$.

8. The method of claim 1, wherein the presence of the GG genotype at single nucleotide polymorphism (SNP) rs17702901 (SEQ ID NO: 829) is associated with weight loss after RYGB surgery.

9. The method of claim 1, wherein step (b) further comprises assaying for at least one genetic indicator, wherein the at least one genetic indicator is a SNP, and wherein the SNP is selected from the group consisting of rs1108723 (SEQ ID NO: 229), rs2383289 (SEQ ID NO: 318), rs3734399 (SEQ ID NO: 358), rs4603757 (SEQ ID NO: 405), rs6737079 (SEQ ID NO: 485), rs6911751 (SEQ ID NO: 502), rs6925786 (SEQ ID NO: 504), and rs9474779 (SEQ ID NO: 612).

* * * * *